US006875852B1

(12) United States Patent
O'Donnell

(10) Patent No.: US 6,875,852 B1
(45) Date of Patent: Apr. 5, 2005

(54) DNA POLYMERASE III HOLOENZYME

(75) Inventor: Michael E. O'Donnell, Hastings on Hudson, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 224 days.

(21) Appl. No.: 08/828,323

(22) Filed: Mar. 28, 1997

Related U.S. Application Data

(63) Continuation of application No. 08/279,058, filed on Jul. 22, 1994, now Pat. No. 5,668,004, which is a continuation-in-part of application No. 07/826,926, filed on Jan. 24, 1992, now abandoned.

(51) Int. Cl.[7] .......................... C12N 9/12; C07H 21/04
(52) U.S. Cl. ..................... 536/23.2; 536/23.1; 435/194; 435/183; 435/320.1; 435/252.1; 530/350
(58) Field of Search ............................. 435/194, 183, 435/320.1, 252.3, 254.11, 325, 410; 530/350, 358; 536/23.2, 23.7, 23.1; 935/22

(56) References Cited

U.S. PATENT DOCUMENTS

| 4,394,143 A | 7/1983 | Weissman et al. ............. 435/6 |
| 5,668,004 A | * 9/1997 | O'Donnell ................... 435/194 |

OTHER PUBLICATIONS

Rudinger (Jun. 1976) Characteristics of the amino acids as components of a peptide hormone sequence. In: Peptide Hormones. Ed. J. A. Parsons. University Park Press, Baltimore, MD. pp. 1–7.*
Ngo et al. (Jan. 1994) Computational complexity, protein structure prediction, and the ILevinthal paradox. In: The Protein Folding Problem and Tertiary Structure Prediction. Eds. Merz et al. Birkhauser et al. Boston, MA. pp. 491–495.*
Thornton et al. (Aug. 1995) Protein Engineering: Editorial Overview. Current Opinion in Biotechnology 6(4): 367–369.*
Wallace (Apr. 1993) Understanding cytochrome c function: engineering protein structure by semisynthesis. The FASEB Journal 7: 505–515.*
Maki et al., "DNA Polymerase III Holoenzyme of *Esherichia coli*," *J. Biol. Chem.* 263:6555–6560 (1988).
O'Donnell, "Accessory Proteins Bind a Primed Template and Mediate Rapid Cycling of DNA Polymerase III Holoenzyme From *Escherichia coli*," *J. Biol. Chem.* 262:16558–16565 (1987).
Onrust et al., "Analysis of the ATPase Subassembly Which Initiates Processive DNA Synthesis by DNA Polymerase III Holoenzyme," *J. Biol. Chem.* 266:21681–21686 (1991).
Onrust et al., "DNA Polymerase III Accessory Proteins," *J. Biol. Chem.* 268:11766–11772 (1993).
Xiao et al., "DNA Polymerase III Accessory Proteins," *J. Biol. Chem.* 268:11773–11778 (1993).

Xiao et al., "DNA Polymerase III Accessory Proteins," *J. Biol. Chem.* 268:11779–11784 (1993).
Flower et al., "The Adjacent dnaZ and dnaX Genes of *Escherichia coli* are Contained Within One Continuous Open Reading Frame," *Nucleic Acids Research* 14:8091–8101 (1986).
Ohmori et al., "Structural Analysis of the dnaA and dnaN Genes of *Escherichia coli*," *Gene* 28:159–170 (1984).
Maki et al., "Structure and Expression of the dnaQ Mutator and the Rnase H Genes of *Escherichia coli*: Overlap of the Promoter Regions," *Proc. Natl. Acad. Sci. USA* 80:7137–7141 (1983).
Tomasiewicz et al., "Sequence Analysis of the *Escherichia coli* dnaE Gene," *J. Bacteriology* 169:5735–5744 (1987).
Shepard et al, "Determination of the Precise Location and Orientation of the *Escherichia coli* dnaE Gene," *J. Bacteriology* 158:455–459 (1984).
Studwell et al., "Replication of the Lagging Strand by DNA Polymerase III Holoenzyme," *Molecular Mechanisms in DNA Replication and Recombination* pp. 153–164 (1990).
Studwell–Vaughan et al., "DNA Polymerase III Accessory Proteins," *J. Biol. Chem.* 268:11785–11791 (1993).
Mike O'Donnell, "Accessory Protein Function in the DNA Polymerase III Holoenzyme from *E. coli*," *BioEssays*, 14:105–111 (1992).
McHenry et al., "DNA Polymerase III of *Escherichia coli*," *Journal of Biological Chemistry*, 254(5):1748–53 (1979).
Kornberg, "DNA Replication"; W.H. Freeman and Company, San Francisco, pp. 172–178 (1980).
Takake et al., *J. Bact.*, 169(12):5692–5699 (1987).
Yoshikawa et al., *Mol. Gen. Genet.*, 209:481–488 (1987).
Maki et al., *J. Biol. Chem.*, 263(14):6547–6554 (1988).
EBML database entry #ECXERB (Jul. 6, 1989).
Ecoseq database entry #YZPA ECOLI (Oct. 1, 1989).
Stirling et al., *EMBO Journal*, 8:1623–1627 (1989).
Studwell et al., "Processive Replication is Contigent on the Exonuclease Subunit of DNA Polymerase III Holoenzyme," *Journal of Biological Chemistry*, 265(2):1171–78 (1990).
O'Donnell et al., *J. Biol. Chem.*, 265(2):1179–1187 (1990).
Stukenberg et al., *Journal of Biological Chemistry*, 266(17):11328–34 (1991).
Kong et al., *Cell*, 69:425–37 (1992).
Carter et al., "Molecular Cloning, Sequencing, and Overexpression of the Structural Gene Encoding the Delta Subunit of *Escherichia coli* DNA Polymerase III Holoenzyme," *Journal of Bacteriology*, 174(21):7013–25 (1992).
EMBL database entry #FCDNAPDPS (Nov. 12, 1992).
EMBL database entry #ECHOLETTA (Nov. 12, 1992).

* cited by examiner

*Primary Examiner*—Richard Hutson
(74) *Attorney, Agent, or Firm*—Nixon Peabody LLP

(57) ABSTRACT

The present invention is directed toward the 5 previously unknown genes, for subunits δ, δ', χ, θ, and ψ, of the DNA polymerase III holoenzyme, and toward a unique man-made enzyme containing 5, preferably 6, protein subunits which shows the same activity as the naturally occurring 10 protein subunit DNA polymerase III holoenzyme.

19 Claims, 13 Drawing Sheets

DNA POLYMERASE III HOLOENZYME

Figure 1:
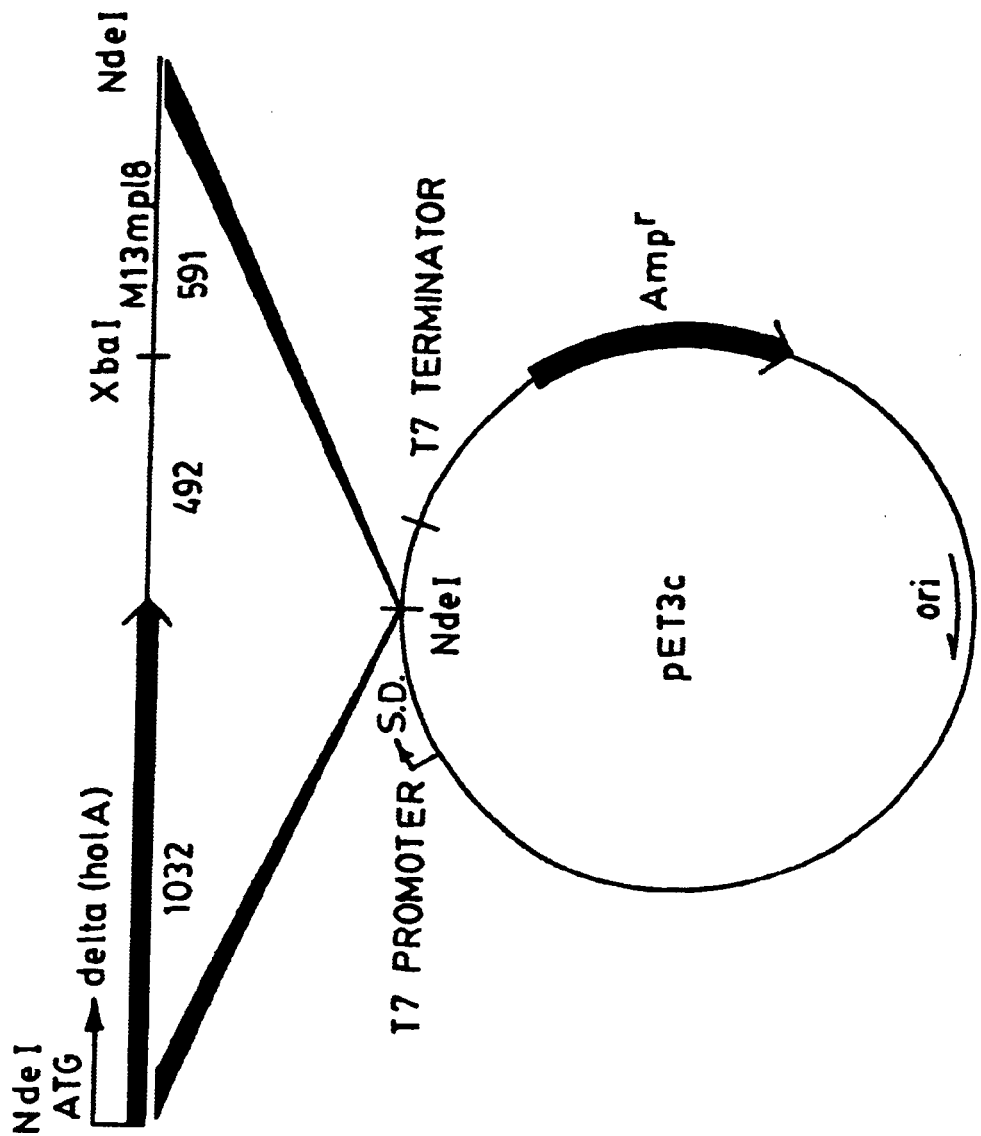

This is a continuation of application Ser. No. 08/279,058, filed on Jul. 22, 1994, now U.S. Pat. No. 5,668,004, which is a continuation-in-part of Ser. No. 07/826,926, filed on Jan. 24, 1992, now abandoned.

Research support which led to the making of the present invention was provided in part by funding from the National Institutes of Health under Grant No. GM-38839. Accordingly, the federal government has certain statutory rights to the invention described herein under 35 U.S.C. 200 et seq.

The present application for Letters Patent is a Continuation-in-Part of my earlier U.S. patent application Ser. No. 07/826,926, filed Jan. 24th 1992, said Continuation-in-Part having been filed as International Patent Application PCT US93/00627 on Jan. 22nd 1993.

In 1982, Arthur Kornberg was the first to purify DNA polymerase III holoenzyme (holoenzyme) and determine that it was the principal polymerase that replicates the *E. coli* chromosome.

In common with chromosomal replicases of phages T4 and T7, yeast, *Drosophila*, mammals and their viruses, the *E. coli* holoenzyme contains at least ten subunits in all ($\alpha$, $\epsilon$, $\theta$, $\tau$, $\chi$, $\delta$, $\delta'$, $\chi'$, $\psi$, $\beta$) [see J. Biol Chem, 257:11468 (1982)]. It has been proposed that chromosomal replicases may contain a dimeric polymerase in order to replicate both the leading and lagging strands concurrently. Indeed the 1 MDa size of the holoenzyme and apparent equal stoichiometry of its subunits (except $\beta$ which is twice the abundance of the others) is evidence that the holoenzyme has the following dimeric composition: $(\alpha\epsilon\theta)_2\tau_2(\gamma\delta\delta'\chi\psi)_2\beta_4$.

One of the features of the holoenzyme which distinguish it as a chromosomal replicase is its use of ATP to form a tight, gel filterable, "initiation complex" on primed DNA. The holoenzyme initiation complex completely replicates a uniquely primed bacteriophage single-strand DNA (ssDNA) genome coated with the ssDNA binding protein (SSB), at a speed of at least 500 nucleotides per second (at 30° C.) without dissociating from an 8.6 kb circular DNA even once. This remarkable processivity (nucleotides polymerized in one template binding event) and catalytic speed is in keeping with the rate of replication fork movement in *E. coli* (1 kb/second at 37° C.). In comparison, DNA polymerase I as well as the T4 polymerase, Taq polymerase, and T7 polymerase (sequence) are all very slow (10–20 nucleotides) and lack high processivity (10–12 nucleotides per binding event). With these distinctive features the polyIII holoenzyme has commercial application. However, there is a good reason it has not yet been applied commercially. Namely, there are only a few (10–20) molecules of polyIII holoenzyme per cell and thus it is difficult to purify; only a few tenths of a milligram can be obtained from 1000 liters of cells; and it can not be simply overproduced by genetic engineering because it is composed of 10 different subunits.

The subunits of DNA polymerase III holoenzyme are set forth in the following table:

| Gene | Subunit | Mass (kda) | Functions |
| --- | --- | --- | --- |
|  | $\alpha$ | 130 | DNA polymerase |
|  | $\epsilon$ | 27 | Proofreading 3'–5' exonuclease |
|  | $\theta$ | 10 |  |
|  | $\tau$ | 71 | Dimerizes core, DNA-dependent ATPase |
|  | $\gamma$ | 47 | Binds ATP |
| holA | $\delta$ | 35 | Interact with g to transfer $\beta$ to DNA |
| holB | $\delta'$ | 33 | DNA-dependent ATPase with g |
| holC | $\chi$ | 15 |  |
| holD | $\psi$ | 12 |  |
| holE | $\beta$ | 40 | Sliding clamp on DNA, binds core |

As discovered in making the present invention, the $\delta'$ is a mixture of two proteins, both encoded by the same holB gene, and therefore it may be regarded as two subunits of the holoenzyme, thus bringing the total number of subunits in the holoenzyme to eleven.

The genes for 5 of the holoenzyme's subunits have been identified [see Nucleic Acids Research 14(20): 8091 (1986); Gene 28:159 (1984); PNAS (USA) 80:7137 (1982); J. of Bacteriology 169(12): 5735(1987); and J. of Bacteriology 158:455 (1984)]. These 5 genes have been cloned and overproducing expression plasmids for these 5 subunits are commercially available. However, prior to the present invention, the identification for the remaining 5 subunits which make up the holoenzyme was not known.

The present invention describes, for the first time, the genetic and peptide sequences for the remaining five subunits of the polymerase III holoenzyme. In addition, to sequence these genes, very efficient operproducing plasmids for each of them have been constructed, and purification protocols for each have been devised. Whereas the low amount of holoenzyme in cells has allowed the subassemblies to be available in microgram quantities prior to the present invention (milligrams of pure $\alpha$, $\epsilon$, $\tau$, $\delta$ and $\beta$ subunits are available using molecular cloned genes in overproducing expression plasmids), utilizing techniques according to the present invention it has been possible to obtain approximately 100 mg of homogeneous subunit from 4 L of cells.

Prior to the identification of the remaining 5 genes of the holoenzyme, a few micrograms of each subunit was resolved from the holoenzyme. The sequence analysis of these resolved subunits eventually lead to the identification of their genetic sequences, and then to the genes per se. In addition, reconstitution studies were carried out to determine which subunits were essential to the speed and processivity of the holoenzyme. In addition, overproducing expression plasmids for these 5 subunits were produced.

Following these studies, it has now been determined, according to the present invention, that at least 5 subunits are required for the action of this enzyme ($\alpha$, $\epsilon$, $\beta$, $\delta$, and $\gamma$), and preferably 6 subunits are essential for the speed and processivity of the holoenzyme. These subunits, the combination of which are essential for the unique synthetic capabilities of the holoenzyme, according to the present invention, are: $\alpha$, $\epsilon$, $\beta$, $\delta$, $\delta'$, and $\gamma$.

The 5 subunits according to the present invention which have been identified, sequenced, cloned, provided in overproducing expression plasmids, expressed, and purified for the first time are subunits $\delta$, $\delta'$, $\chi$, $\theta$, and $\psi$.

Figure 2:
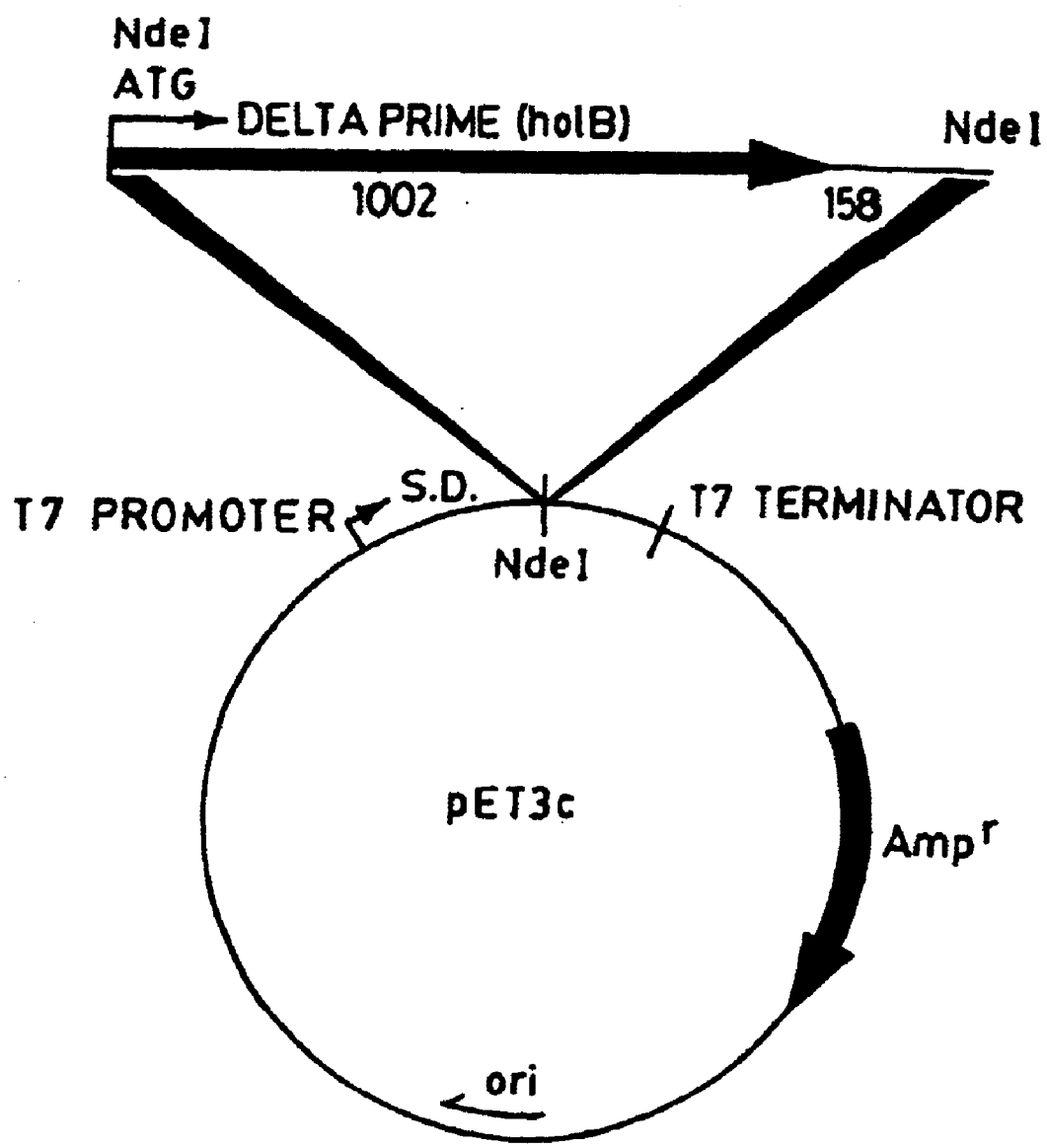
Figure 3A:
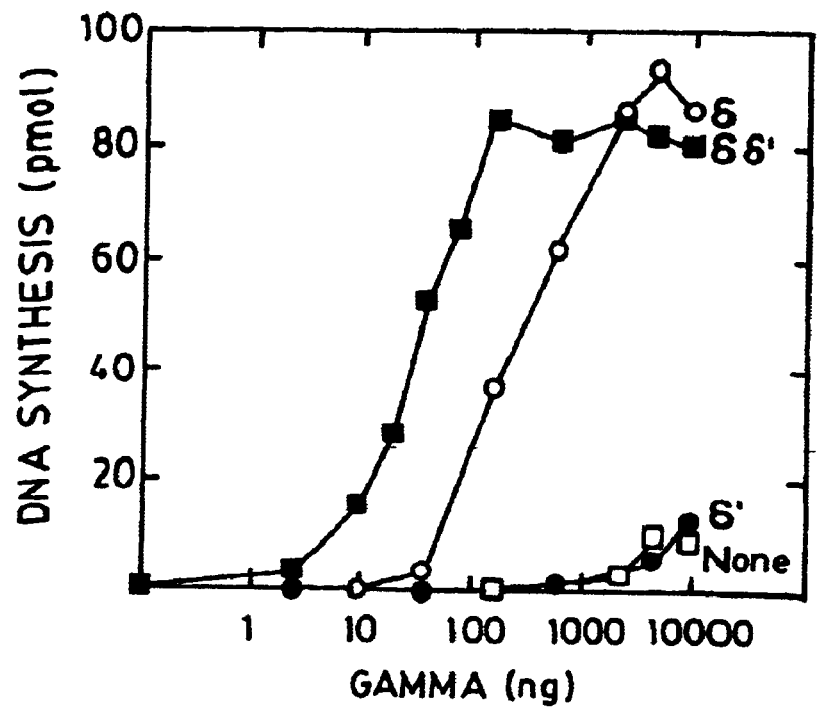
Figure 4A:
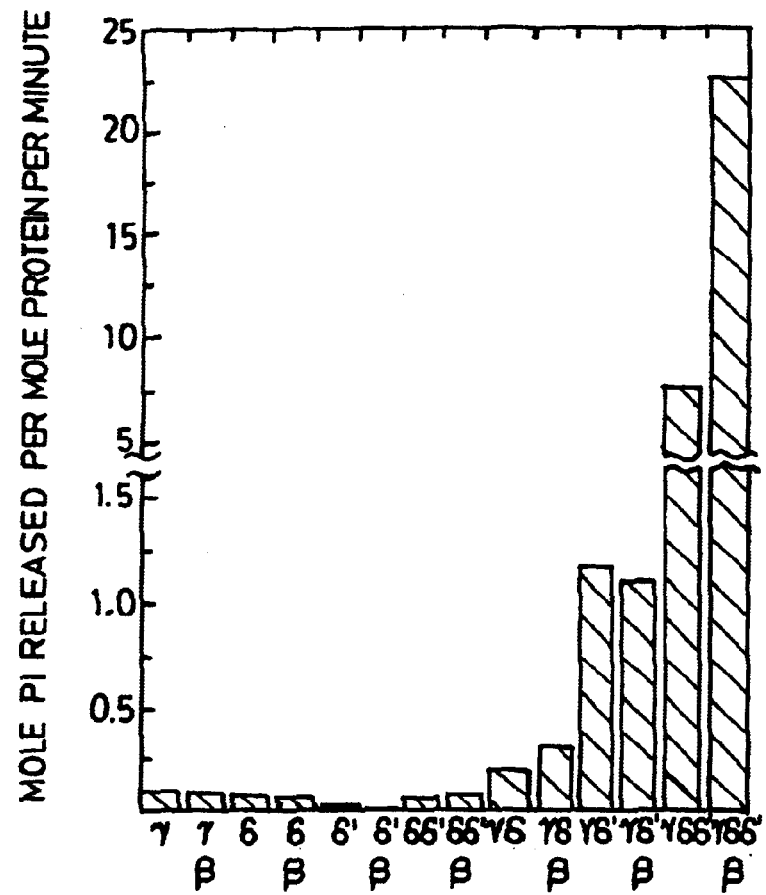
Figure 5:
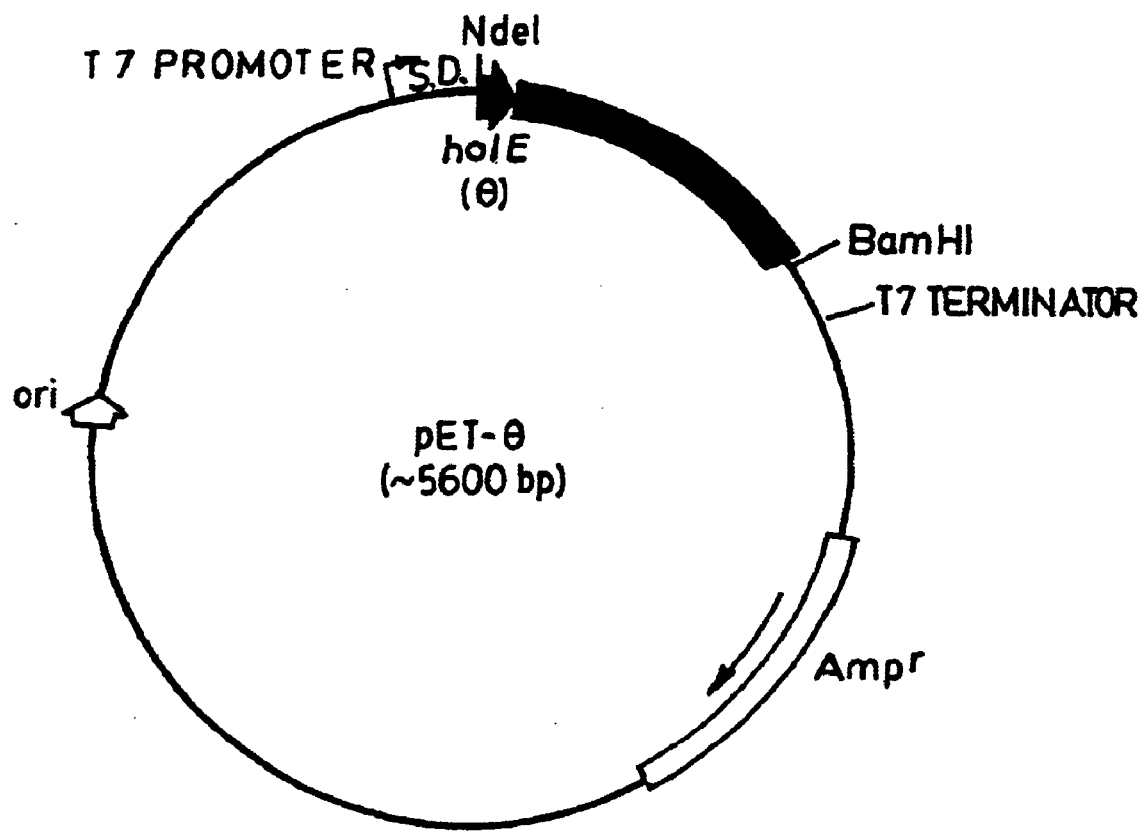
Figure 6A:
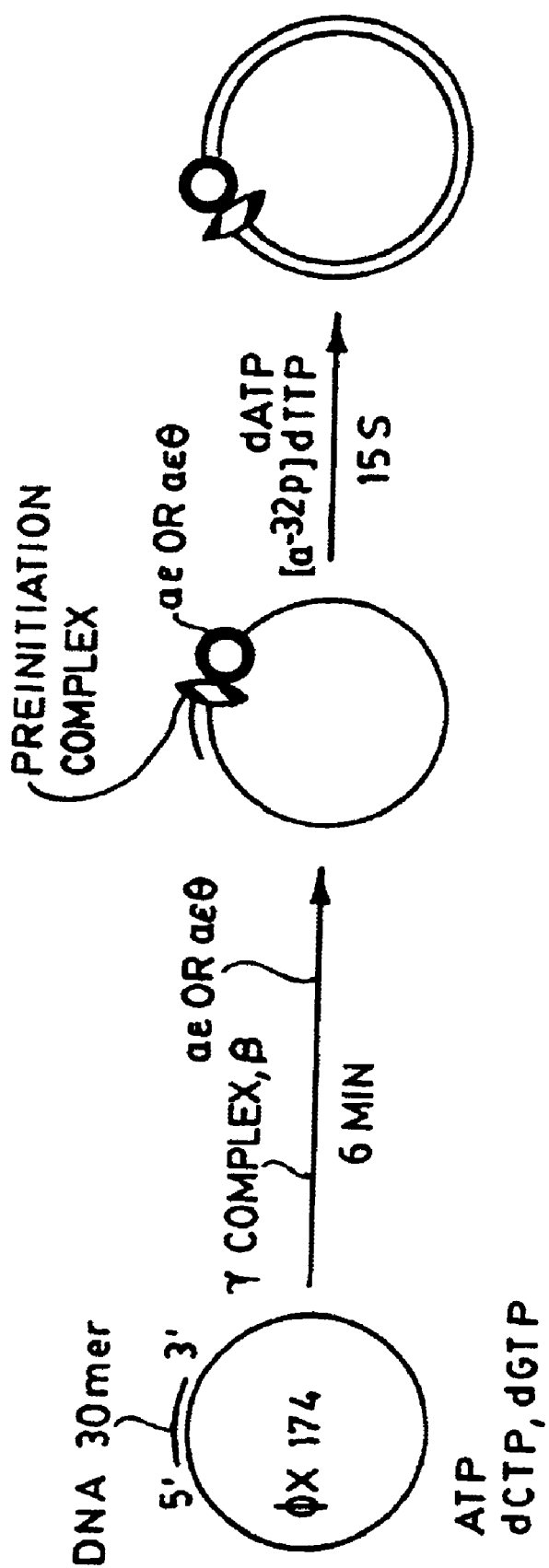
Figure 7:
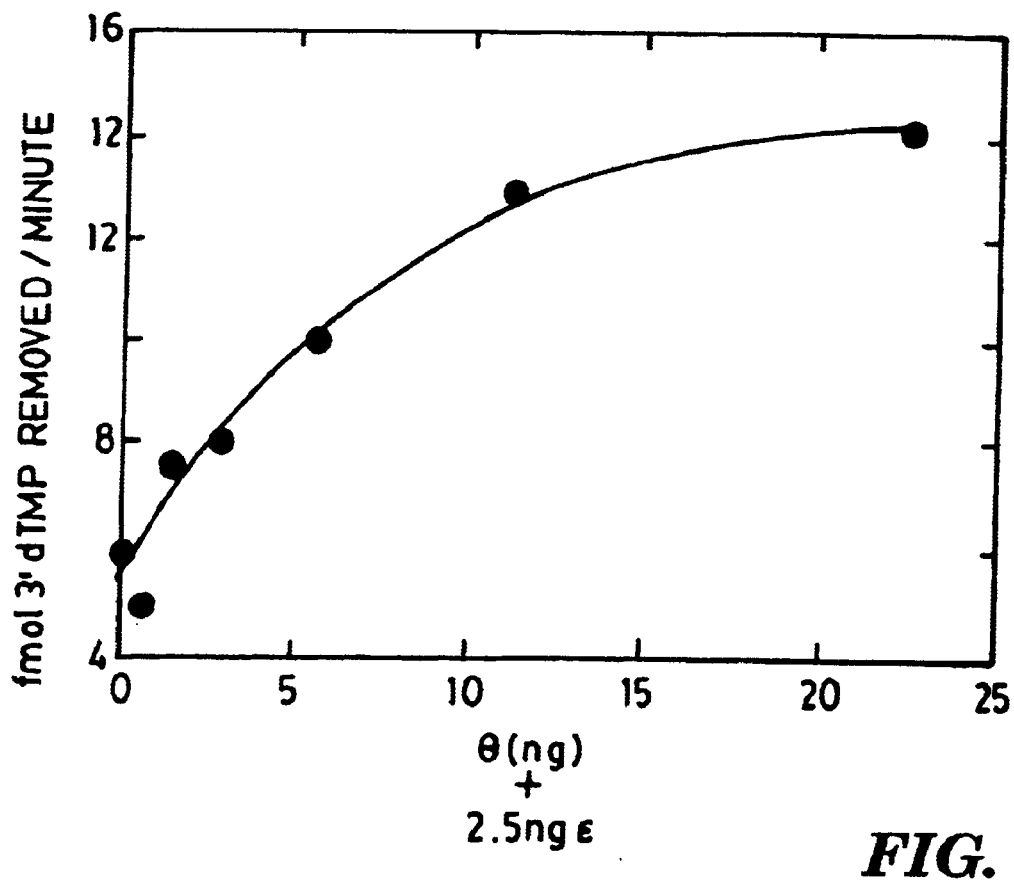
Figure 8A:
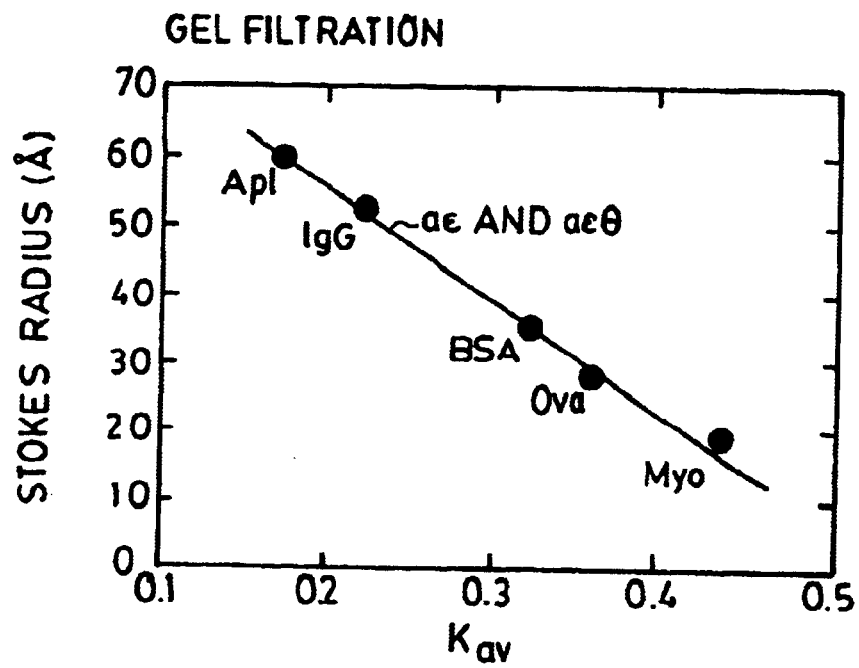
Figure 9:
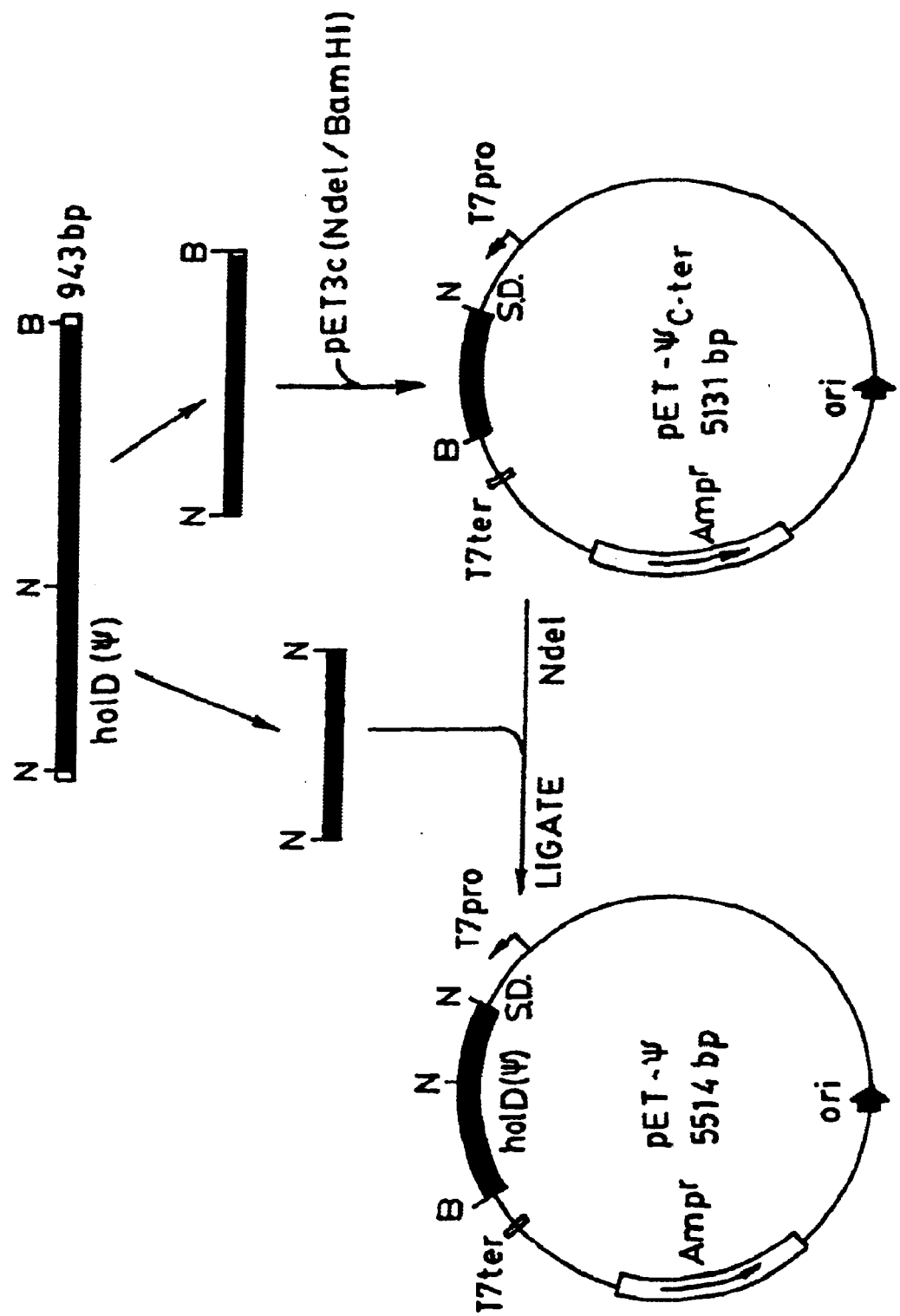
Figure 10A:
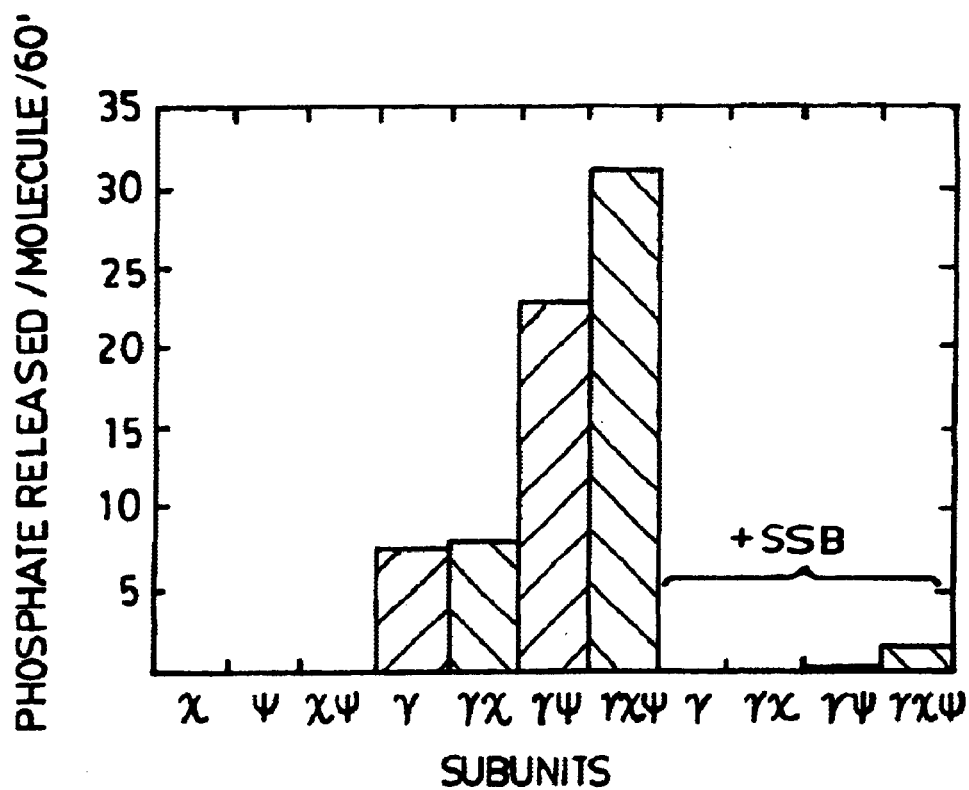
Figure 11:
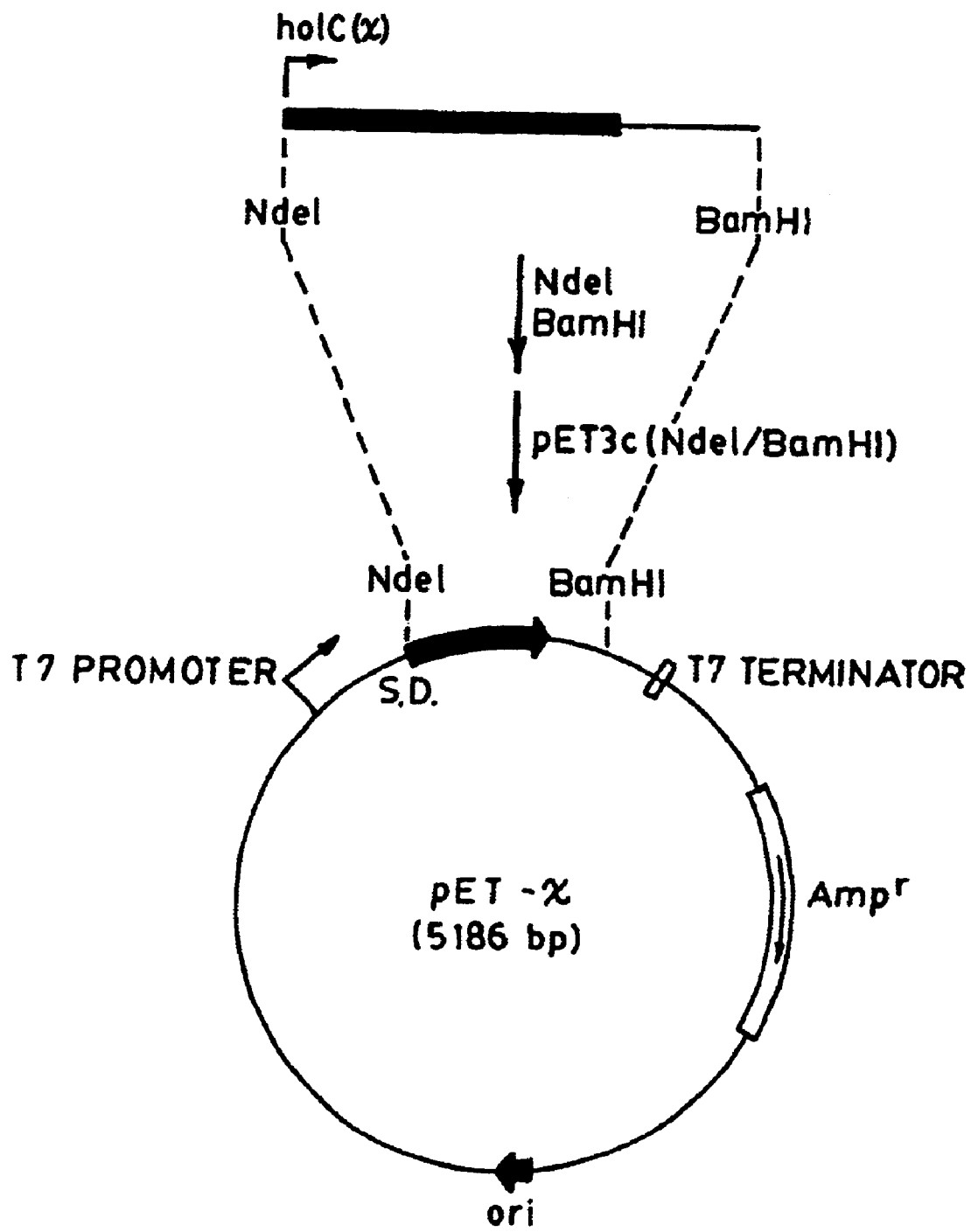
Figure 12A:
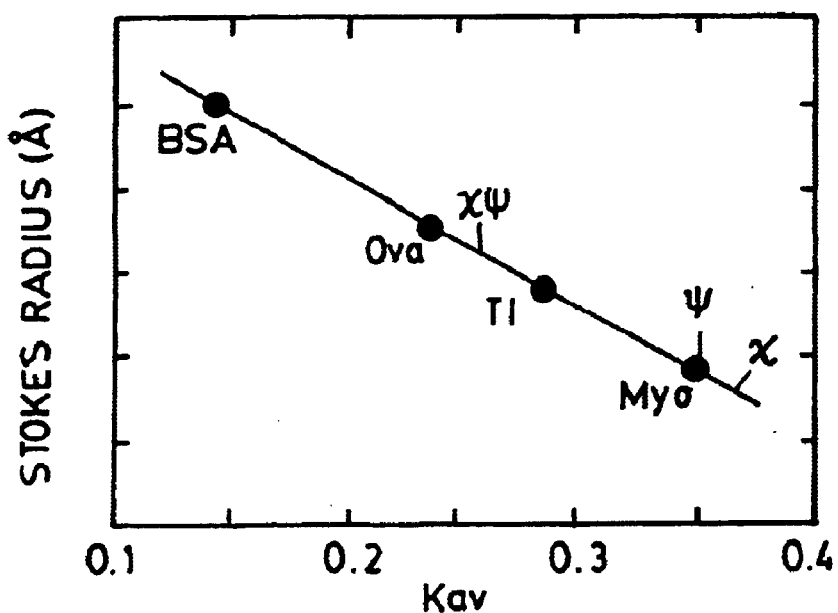

The following figures, detailed description and examples are provided in order to allow the reader to obtain a fuller and more complete understanding of the present invention. With regard to the figures, FIG. 1 depicts the pET-$\delta$ expression vector according to the present invention;

FIG. 2 depicts the pET-$\delta'$ expression vector according to the present invention;

FIG. 3A, B, and C depict the replication activity of δ, δ' and δδ' with γ and τ according to the present invention;

FIG. 4A and B depict the effect of δ' and δ on the ATPase activity of γ and τ according to the present invention;

FIG. 5 depicts the pET-θ expression plasmid according to the present invention;

FIG. 6A and B depict the reconstitution assay according to the present invention indicating that θ does not stimulate DNA synthesis;

FIG. 7 depicts that θ, according to the present invention stimulates ε in excision of an incorrect 3' TG base pair;

FIG. 8A and B depicts the native molecular weight of αε and polIII core according to the present invention;

FIG. 9 depicts the construction of the pET-ψ overproducing plasmid according to the present invention;

FIG. 10A and B depict the stimulation of the DNA dependent ATPase of γ and τ by ψ and χ, according to the present invention;

FIG. 11 depicts the construction of the pET-χ expression plasmid according to the present invention; and FIG. 12A and B depicts native molecular mass of χ, ψ and the χψ complex, according to the present invention.

More specifically with regard to FIG. 1, there is shown the expression vector for δ as prepared and described in the following examples. The holA gone excised from M13-δ-NdeI using NdeI is shown above the pET3c vector. The open reading frame encoding δ is inserted into the NdeI site of pET3c such that the initiating ATG is positioned downstream of the Shine-Dalgarno sequence and a T7 promoter. Downstream of the holA insert are 492 nucleotides of *E. coli* DNA and 591 nucleotides of M13mp18 DNA. The T7 RNA polymerase termination sequence is downstream of the holA insert.

More specifically with regard to FIG. 2, the holB fragment excised from M13-δ'-NdeI using NdeI is shown above the expression vector. The open reading frame encoding δ' is inserted into the NdeI site of pET3c such that the initiating ATG is positioned downstream of the Shine-Dalgarno sequence and a T7 promoter. The holB insert also contains 158 nucleotides of *E. coli* DNA downstream of the the holB stop codon to an NdeI site. The T7 polymerase termination sequence is downstream of the holB insert.

Figure 3B:
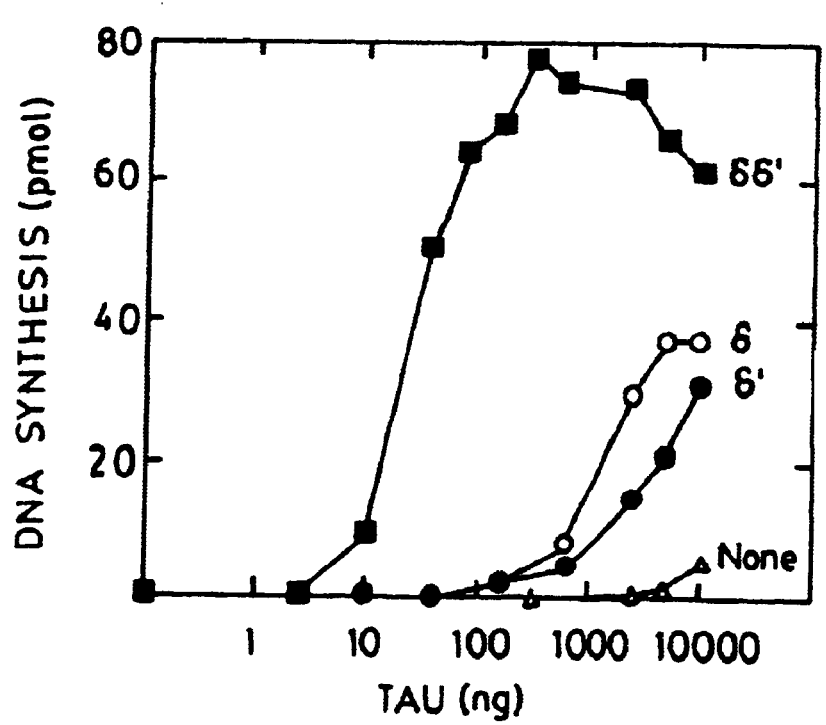
Figure 3C:
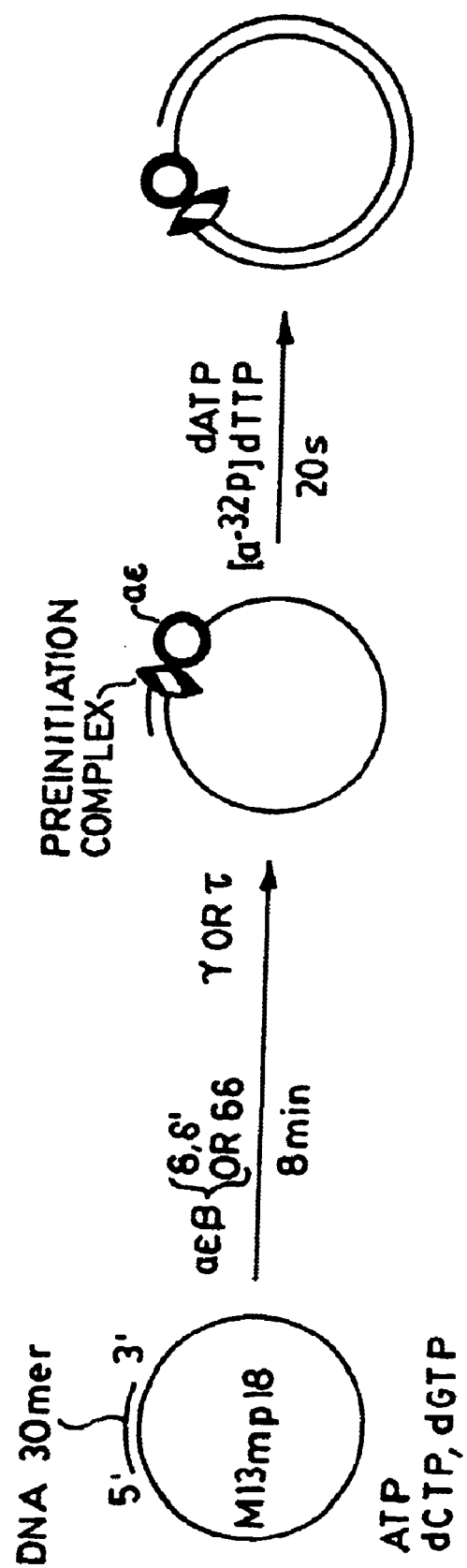

With regard to FIG. 3, replication assays were performed as described below. FIG. 3C summaries the replication assays. Either γ or τ was titrated into assays containing SSB "coated" primed M13mp18 ssDNA, ʃ, αε and either 2 ng δ, 2 ng δ' or an equal mixture (1 ng each) of δ and δ' (δδ'). The reaction mixture was preincubated for 8 minutes to allow reconstitution of the processive polymerase prior to initiating a 20 second pulse of DNA synthesis. FIG. 3A depicts the results of the γ subunit being titrated into the replication mixture either alone (open squares) or containing either δ' (closed circles), δ (open circles), or δδ' (closed squares). FIG. 3B depicts the results of the γ subunit being titrated into the replication mixture either alone (open triangles), or containing either δ' (closed circles), δ (open circles), or δδ' (closed squares).

Figure 4B:
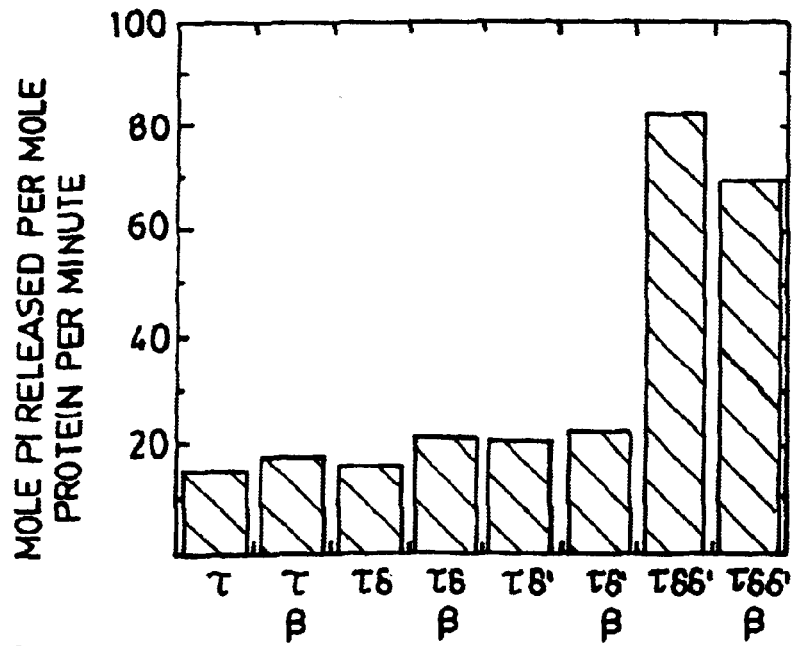

With regard to FIG. 4, ATPase assays were performed in the presence of M13mp18 ssDNA as described in detail below. The subunits in each assay are identified below the plot in the figure. FIG. 4A refers to the effect of δ, δ' and β on the γATPase; FIG. 4A refers to the effect of δ, δ' and β on the τATPase.

With regard to FIG. 5, the shaded NdeI-BamHI segment includes the holE gene (arrow). Transcription of the holE is driven by a T7 promoter. The T7 RNA polymerase termination sequence is downstream from the *E. coli* DNA insert. Translation of δ is aided by an upstream Shine-Dalgarno sequence.

With regard to FIG. 6, the replication reactions were performed as described below. FIG. 6A outlines the protocol summarizing the assay. Either the αε complex or reconstituted polIII core (αεθ) were titrated into the assay which contains β, γ complex and primed phage χ 174 ssDNA "coated" with SSB. Proteins and DNA were preincubated for 6 minutes to allow time for assembly of the processive polymerase. A 15 second round of synthesis was initiated upon addition of remaining deoxynucleoside triphosphates. Circles: titration of αε complex; triangles: titration of αεθ. The α subunit was limiting in these assays and therefore the amount of αε and αεθ added to the assay is taken as the amount of α added.

With regard to FIG. 7, there is depicted the results of a titration of θ into the assay containing ε and a mismatched 3' 32P-end-labelled T residue on a synthetic "hooked" primer template.

Figure 8B:
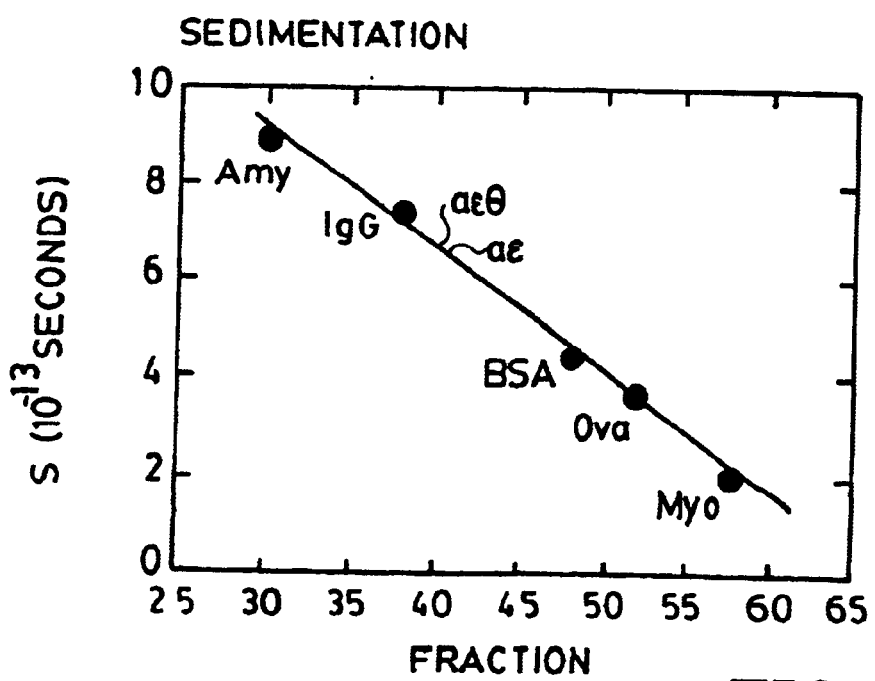

With regard to FIG. 8, the is shown a comparison of the migration of αε and polIII core relative to protein standards on gel filtration and in glycerol gradients. The position of polIII core reconstituted using either excess or substoichiometric θ was the same in both types of analysis. FIG. 8A depicts gel filtration analysis on Superose 12. The Stokes radius of protein standards was calculated from their known diffusion coefficients. FIG. 8B depicts glycerol gradient sedimentation analysis. Sedimentation coefficients of the standards are Amy, sweet potato β-amylase (152 kDa, 8.9 S); Apf, horse apoferritin (467 kDa, 59.5 Å); IgG; bovine immunoglobulin G (158 kDa, 52.3 Å, 7.4 S); USA, bovine serum albumin (67 kDa, 34.9 Å, 4.41 S); Ova, chicken ovalbumin (43.5 kDa, 27.5 Å, 3.6 S); Myo, horse myoglobin (17.5 kDa, 19.0 Å, 2.0 S). The positions of αε and polIII core relative to the protein standards are indicated in the plots. The Stokes radii and S values of αε and polIII were measured by comparison to the standards.

With regard to FIG. 9, the holD gene was amplified from genomic DNA using primers which form an NdeI site at the initiating ATG and downstream BamHI site. Due to an internal NdeI site within holD, insertion of the complete holD gene into the pET3c expression plasmid required the two steps shown below. Additional details appear in the following description.

Figure 10B:
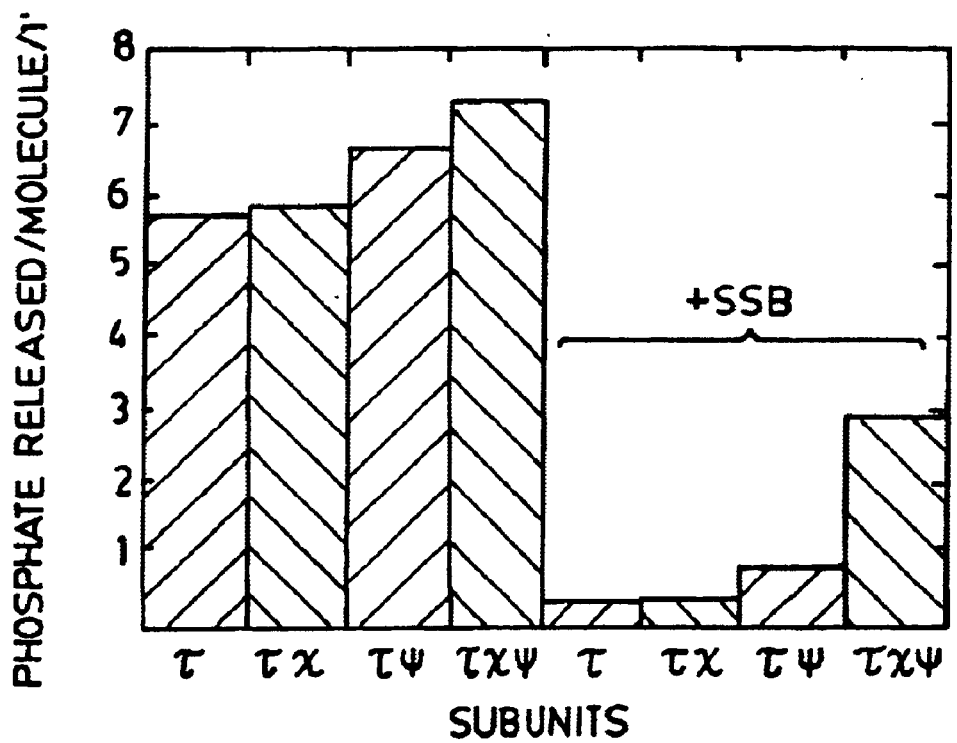

With regard to FIG. 10, ATPase assays were performed using a two-fold molar excess of χ and ψ (as monomers) over γ and τ (as dimers) and using M13mp18 ssDNA as an effector. FIG. 10A depicts ATPase assays of ψ, χ, γ and combination of these proteins; FIG. 10B depicts the effect of ψ and τ subunits on the ATPase of τ. Subunits in the assays are indicated below the plots, and assays performed in the presence of SSB are indicated.

With regard to FIG. 11, the holC gene was amplified from genomic DNA using primers which generate an NdeI site at the start codon of holC and a BamHI site 152 nucleotides downstream of holC as described below. The 604 bp amplified product was purified, digested with NdeI and BamHI, and ligated into the NdeI and BamHI sites of pET3c to yield pET-χ. The open reading frame encoding χ was inserted into the NdeI-BamHI sites of pET3c such that the initiating ATG is positioned downstream of the Shine-Dalgarno sequence and a T7 promoter. The T7 RNA polymerase termination sequence is downstream of the holC insert. The Amp$^r$ indicates the ampicillin resistance gene; the ori indicates the pB322 origin of replication.

Figure 12B:
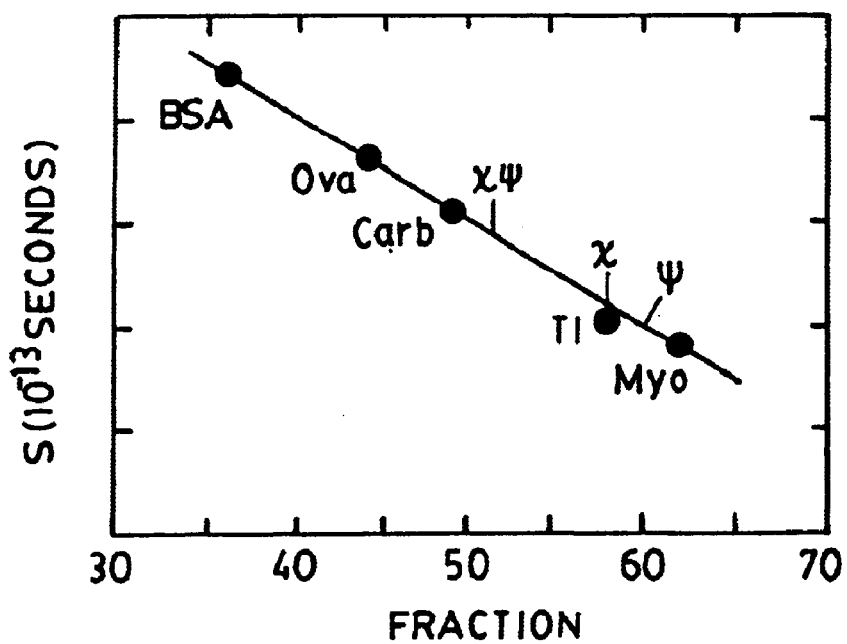

With regard to FIG. 12A, the Stokes radius of χ, ψ and χψ complex was determined by comparison with protein standards in gel filtration on Superdex 75. With regard to FIG. 12B, the S value of χ, ψ and χψ complex determined by comparison to protein standards in glycerol gradient analysis are given. The protein standards were: bovine serum albumin (BSA), 34.9 Å, 4.41 S; chicken ovalbumin (Ova) 27.5 Å, 3.6 S; soybean trypsin inhibitor (TI), 23.8 Å; bovine carbonic anhydrase II (Carb), 3.06 S; horse myoglobin (Myo), 19.0 Å, 2.0 S; and horse kidney metalothionin (Met), 1.75 S.

In general, the sequence for each of the genes for the five subunit peptides, according to the present invention, began with isolating, purifying and sequencing the individual peptides.

The δ, δ', χ, ψ subunits were purified by a combination of two published procedures. First the γ complex (γ, δ, δ', ψ, was purified from 1.5 Kg *E. coli* HB101 (pNT203-pSK100) as described by Maki [see J. Bio. Chem 263:6555(1988)]. Second, the complex was split into two fractions—"aγχψ" complex and a "δδ'" complex—as described by O'Donnell [see J. Bio. Chem 265:1179 (1990)]. The peptide sequences for δ and δ' were obtained from the δδ' fraction; whereas the peptide sequences of χ and ψ are obtained from the γψχ fraction. The θ subunit sequence was obtained from a side fraction off this procedure which contained nearly pure polymerase III (α, ε, θ) subunits.

For all 5 proteins, the amino acid sequences were obtained in the same manner, by the use of N-terminal analysis and tryptic analysis. N-terminal analysis was conducted using known techniques of SDS-PAG electrophoresis [see Nature 227:680(1970)] in a 15% gel, and subsequent electroelution onto PVDF membrane. The resolved peptides were removed from the membrane and sequenced. For tryptic analysis, either δδ' or γχψ comples was chromatographed in a 15% SDS-PAG gel to separate the individual subunits. However, for this procedure, the 100 pmol was eloctroblotted onto nitrocellulose. The nitrocellulose membrane was then digested with trypsin, and the peptides resolved by microbore HPLC. The resolved peptides were then sequenced.

The electroblotting procedure used in the tryptic analysis protocol is more fully described in the following general example:

EXAMPLE I

Electroblotting

SDS (Bio-Rad) was purified by crystallization from ethanol-water. SDS (100 g) was added to ethanol (450 g), stirred, and heated to 55° C. Additional hot water was added (50–75 ml) until all of the SDS dissolved. Activated charcoal (10 g) was added to the solution, and after 10 minutes the slurry was filtered through a Buchner funnel (Whatman No. 5 paper) to remove all the charcoal. The filtered solution was chilled, first a 4° C. for 24 hrs and then at −20° C. for an additional 24 hrs. Crystalline SDS was collected on a coarse-frit sintered-glass funnel and washed with 800 ml of ethanol chilled to −20° C. The partial purified SDS was then recrystallized using the above procedure but without the charcoal. 0.75 mm SDS-Laemmli gel was made using ultra-pure reagents. Prior to electrophoresis 10 mM Glutatnhione (to a final concentration of 0.05 mM) was added to the upper chamber buffer, and the system preelectrophoresed 2 hr at 3–5 mA (3 mA for mini-gel, 5 mA for normal). After 2 hrs, the upper chamber was emptied and standard trisglycine buffer was added. The samples to be run were denatured using Laemmli denaturaton solution made from the ultra-pure reagents (in the presence of 5 mM DTT). The gel was run under conditions such that separation was achieved in less than 2 hrs. After the gel run, the gel was soaked for 30 min in 10 mM CAPS pH 11, 5% methanol (% of methanol will vary depending on the size of the protein: in general, high molecular weight proteins transfer more efficiently in absence of methanol while low molecular weight proteins require methanol in the buffer). CAPS buffer was made by titrating a 10 mM solution with 10 N NaOH. For gel transfer, slices of immobilon were wet in 100% methanol and equilibrated 10 min in the CAPS transfer buffer, and the protein transferred using Bio-Rad mini blotter (transfer time will vary depending on protein size, methanol, etc.; ~70 kDa polypeptide will transfer in 90 min in the presence of 5% methanol at 15V). After transfer, immobilon was soaked in distilled water for 5 min, and the membrane was stained with 0.1% Commassie Blue R250 in 50% methanol for 1 min, and destained in 50% methanol and 10% aldehyde-free acetic acid. The membranes were soaked in distilled water for 10 min, and allowed to air dry. Protein bands of interest were cut from the membrane and stored in eppendorf tubes at −20° C. until sequenced.

The identification of the subunit gene of DNA polymerase III δ was accomplished by purifying the δ δ' proteins to apparent homogeneity through an ATP-agarose column from 1.3 kg of the δ/τ overproducing strain of *E. coli* [HB 101 (pNT 203, pSK 100)].

The δ δ' subunits were separated by electrophoresis in a 15% SDS-PAG (polyacrylamide gel), then electroblotted onto PVDF membrane (Whatman) for N-terminal sequencing (50 pmol each) [see J. Biol. Chem. 262:10035 (1987)], and onto nitrocellulose membrane (Schleicher and Schuell) for tryptic analysis (140 pmol each) [see PNAs USA 84:6970 (1987)]. Proteins were visualized by Ponceau S (Sigma). Protein sequences were determined using an Applied Biosystems 470A gas-phase microsequenator. Sequence results were as follows:

```
N-terminal sequence:
NH2-Met Leu Arg Leu Tyr Pro Glu Gln Leu Arg Ala Gln Leu Asn
                          5                    10

Glu Gly Leu Arg Ala Ala Tyr Leu Leu Leu Gly Asn Asp Pro;
 15                  20                   25 tryptic peptide δ-1:
NH2-Ala Ala Tyr Leu Leu Leu Gly Asn Asp Pro Leu Leu Leu Gln
                      5                     10

Glu Ser Gln Asp Ala Val Arg;
 15                 20 tryptic peptide δ-2:
```

```
                          -continued
NH2-Ala Gln Glu Asn Ala Ala Trp Phe Thr Ala Leu Ala Asn Arg
                    5                    10 tryptic peptide δ-3:
NH2-Val Glu Gln Ala Val Asn Asp Ala Ala His Phe Thr Pro Phe
                    5                    10

His Trp Val Asp Ala Leu Leu Met (Gly) (Lys).
 15                     20
```

Paranthesis in the above sequence indicate uncertainty in the amino acid assignment.

The DAN sequencing, construction of the overproducing vector, and DNA replication assays for this subunit were conducted according to the following example:

EXAMPLE II

DNA Sequencing:

The 3.2 kb KpnI/Bg1II (restriction enzymes, New England Biolabs) fragment containing δ was excised from λ169 (Kohara) and directionally ligated into pUC18 to yield pUCdelta. Both strands of DNA were sequenced by the chain termination method of Sanger using the United States Biochemicals sequenase kit, [α-$^{35}$S]dCTP (New England Nuclear), and synthetic DNA 17-mers (Oligos etc. Inc.). All sequence information presented here was determined on both strands using both dGTP and dITP in sequencing reactions.

Construction of the Overproducing Vector:

Approximately 1.7 kb of DNA upstream of δ was excised from pUCdelta using KpnI (polylinker site) and BstXI (the BstXI site is 13 base pairs upstream of the start codon of holA) followed by self-ligation of the plasmid. A 1.5 kb fragment containing the holA gene was then excised using EcoRI and XbaI (these sites are in the pUC polylinker on either side of the δ insert) followed by directional ligation into M13mp18 to yield M13delta. An NdeI site was generated at the start codon of holA by primer directed mutagenesis [see Methods Enzymol 154:367 (1987)] using a DNA 33-mer (5'→3'):

GTACAACCGA ATCATATGTT ACCCAGCGAG CTC 33 containing the NdeI site (underlined) at the start codon of holA to prime replication of M13delta viral ssDNA, and using DNA polymerase and SSB in place of Klenow polymerase to completely replicate the circle without strand displacement [see J. Biol. Chem. 260:12884 (1985)]. The NdeI site was verified by DNA sequencing. An NdeI fragment (2.1 kb) containing the δ gene was excised from the NdeI mutated M13 delta and ligated into pET-3c linearized using NdeI to yield pETdelta. The orientation of the holA gene in pETdelta was determined by sequencing.

DNA Replication Assays:

The replication assay contained 72 ng M13mp18 ssDNA (0.03 pmol as circles) uniquely primed with a DNA 30-mer [see J. Biol. Chem. 266:11328 (1991)], 980 ng SSB (13.6 pmol as tetramer), 22 ng β (0.29 pmol as dimer), 200 ng γ (2.1 pmol as tetramer), 55 ng αε complex in a final volume (after addition of proteins) of 25 μl 20 mM Tris-HCL (pH7.5), 8 mM MgCl$_2$, 5 mM DTT, 4% glycerol, 40 μg/ml BSA, 0.5 mM ATP, 60 μM each dCTP, dGTP, dATP and 20 μM [α-$^{32}$P]dTTP (New England Nuclear). Proteins used in the reconstitution assay were purified to apparent homogeneity and their concentration determined. Delta protein or column fraction containing δ, was diluted in buffer (20 mM Tris-HCL (pH7.5), 2 mM DTT, 0.5 mM EDTA, 20% glycerol, 60 mM NaCl and 50 μg/ml BSA) such that 1–10 ng of protein was added to the assay on ice, shifted to 37° C. for 5 minutes, then quenched upon spotting directly onto DE81 filter paper. DNA synthesis was quantitated as described.

Gel Filtration:

Gel filtration of δ, δ' and the δδ' complex was performed using an HR 10/30 Superdex 75 column equilibrated in 20 mM Tris-HCL (pH 7.5). 10% glycerol 2 mM DTT, 0.5 mM EDTA and 100 mM (buffer B). Either δ (30 μg, 0.78 nmol as monomer), δ' (30 μg, 0.81 nmol as monomer) or a mixture of δ and δ' (30 μg of each) were incubated for 30 minutes at 15° C. in 100 μl of buffer B then the entire 100 μl sample was injected onto the column. The column was developed with buffer B at a flow rate of 0.3 ml/minute and after the first 6 ml, fractions of 170 μl were collected. Fractions were analyzed by 13% SDS polyacrylamide gels (100 μl per lane) stained with Commassie Brilliant Blue. Densitometry of stained gels was performed using a Pharmacia-LKB Ultrascan XL laser densitometer.

Gel filtration of γ or γ mixed with either δ or δ' or both δ and δ' was performed using an HR 10/30 Superose 12 column equilabrated in buffer B. Protein mixtures were preincubated 30 minutes at 15° C. in 100 μl buffer B then injected onto the column and the column was developed and analyzed as described above. Replication activity assays of these column fractions were performed as described above with the following modifications. The γ subunit was omitted from the assay and each fraction was diluted 50-fold with 20 mM Tris-HCL (pH 7.5), 10% glycerol, 2 mM DTT, 0.5 MM EDTA and 50 μg/ml BSA. Then 2 μl of diluted fraction was withdrawn and added to the assay.

Protein standards were a mixture of proteins obtained from BioRad and from Sigma Chemical Co. and were brought to a concentration of approximately 50 μg each in 100 μl buffer B before analysis on either Superdex 75 or Superose 12 columns.

Glycerol Gradient Sedimentation:

Sedimentation analysis of δ, δ' and a mixture of δ and δ' were performed using 11.6 ml 10%–30% glycerol gradients in buffer B. Either δ (57 μg, 1.5 nmol as monomer), δ' (56 μg, 1.5 nmol as monomer) or a mixture of δ and δ' (57 μg and 56 μg, respectively) were incubated at 15° C. for 30 minutes in a final volume of 100 μl buffer B then each sample was layered onto a separate gradient. Protein standards (50 μg each in 100 μl buffer B) were layered onto another gradient and the gradients were centrifuged at 270,000×g for 60 hours at 4° C. Fractions of 170 μl were collected from the bottom of the tube and analyzed (100 μl/lane) in a 13% SDS polyacrylamide gel stained with Coomassie Blue.

Light Scattering:

The diffusion coefficient of δ, δ' and the δδ' complex was determined by dynamic light scattering at 780 nm in a fixed angle (90°) Biotage model dp-801 light scattering instrument (Oros Instruments). Samples of δ (200 μg, 5.2 nmol as monomer), and δ' (200 μg, 5.4 nmol as monomer) were in 400 μl of 20 mM Tris-HCL (pH 7.5), 100 mM NaCl and 1.2% glycerol. The mixture of δ and δ' (100 μg of each) was in 400 μl of 20 mM Tris-HCl (pH 7.5) and 100 mM NaCl. The observed diffusion coefficient of δ' in the presence of 1.2% glycerol was 0.6% higher than in the absence of glycerol. Hence, the 1.2% glycerol in the δ and δ' samples had little effect on the observed diffusion coefficient.

The purification of δ was preformed according to the following example:

EXAMPLE III

Purification of δ

BL21 (DE3) cells harboring pETdelta were grown at 37° C. in 12 liters of LB media containing 100 μg/ml of ampicillin. Upon growth to OD 1.5, the temperature was lowered to 25° C., and IPTG was added to 0.4 mM. After a further 3 hrs. of growth, the cells (50 g) were collected by centrifugation. Cells were lysed using lysozyme as described in prior publications, and the debris removed by centrifugation. The following purification steps were performed at 4° C. The assay for δ is as described above.

The clarified cell lysate (300 ml) was diluted 2-fold with 20 mM Tris-HCl (pH 7.5), 20% glycerol, 0.6 mM EDTA, 2 mM DTT (buffer A) to a conductivity equal to 112 mM NaCl, and then loaded (over 3 hrs.) onto a 60 ml Hexylamine Sepharose column equilibrated with buffer A plus 0.1 M NaCl. The Hexylamine column was washed with 60 ml buffer A plus 0.1 M NaCl, and then eluted (over 14 hrs) using a 600 ml linear gradient of 0.1 M NaCl to 0.5 M NaCl in buffer A. Eighty fractions were collected. Fractions 16–34 (125 mls) were dialyzed against 2 liters of buffer A plus 90 mM NaCl overnight, and then diluted 2-fold with buffer A to yield a conductivity equal to 65 mM NaCl just prior to loading (over 45 min) onto a 60 ml column of Heparin Sepharose equilibrated in buffer A plus 50 mM NaCl. The heparin column was washed with 120 ml buffer A plus 50 mM NaCl, and then eluted (over 14 hrs) using a 600 ml linear gradient of 0.05 M NaCl to 0.5 M NaCl in buffer A. Eighty fractions were collected. Fractions 24–34 were pooled and diluted 3-fold (final volume of 250 mls) with buffer A to a conductivity equal to 85 mM NaCl just prior to loading (over 50 min) onto a 50 ml Hi-Load 26/10 Q Sepharose fast flow FPLC column. The column was washed with 150 ml buffer A plus 50 mM NaCl, and then eluted using a 600 ml linear gradient of 0.05 M NaCl to 0.5 mM NaCl in buffer A. Eighty fractions were collected. Fractions 28–36 which contained pure δ were pooled (74 mls, 1.9 mg/ml); passed over a 1 ml ATP-agarose column (N-6 linked) to remove any possible γ complex contaminant, and then dialyzed versus two changes of 2 liters each of buffer A containing 0.1 M NaCl (the DTT was ommitted for the purpose of determining protein concentration spectrophotometrically) before storing at −70° C.

The following table gives the results obtained from measuring the protein levels obtained from the fractions taken in Example III.

| Fractions | | total protein (mg) | total units[1] | specific activity (units/mg) | fold purification | % yield |
|---|---|---|---|---|---|---|
| I | Lysate[2] | 2070 | 5.4 × 10⁹ | 2.6 × 10⁶ | 1.0 | 100 |
| II | Hexylamine | 446 | 2.5 × 10⁹ | 5.6 × 10⁶ | 2.2 | 46 |
| III | Heparin | 197 | 2.0 × 10⁹ | 10.2 × 10⁶ | 3.9 | 37 |
| IV | Q Sepharose | 141 | 1.5 × 10⁹ | 10.6 × 10⁶ | 4.1 | 28 |

[1]One unit is defined as pmol nucleotide incorporated per minute
[2]Ommission of gamma from the assay of the lysate resulted in a 200-fold reduction of specific activity (units/mg)

The δ gene was identified using amino acid sequence information from δ. The sequence of the N-terminal 28 amino acids of δ and the sequence of three internal tryptic peptides were determined. One of the tryptic peptides (tryptic peptide δ-1) overlapped 10 amino acids of the N-terminal sequence. A search of the GenBank revealed a sequence which predicted the exact amino acid sequence of the 21 amino acid tryptic peptide δ-1 which overlapped the N-terminal sequence. The matching sequence occurred just downstream of the r1pB gene at 15.2 minutes of the E. coli chromosome. The match of the published DNA sequence to the N-terminal sequence of δ was imperfect due to a few errors in the published sequence of this region. The published sequence of r1pB accounted for approximately 22% of the δ gene and did not encode either of the other two tryptic fragments. The Kohara lamda phage 169 contains 19 kb of DNA surrounding the δ gene. The 3.2 kb KphI/BglII fragment containing δ was excised from λ169, cloned into pUC18 and the δ gene was sequenced. The DNA sequence predicts the correct N-terminal sequence of δ (except the Ile instead of Leu at position 2) and encodes the other two internal tryptic peptides of δ in the same reading frame, and predicts a 343 amino acid protein of 38.7 kda consistent with the mobility of the δ in SDS-PAGE (35 kDa).

The full nucleic acid sequence for the δ gene according to the present invention was determined to be:

```
ATG ATT CGG TTG TAC CCG GAA CAA CTC CGC GCG CAG CTC      39

AAT GAA GGG CTG CGC GCG GCG TAT CTT TTA CTT GGT AAC      78

GAT CCT CTG TTA TTG CAG GAA AGC CAG GAC GCT GTT CGT     117

CAG GTA GCT GCG GCA CAA GGA TTC GAA GAA CAC CAC ACT     156

TTT TCC ATT GAT CCC AAC ACT GAC TGG AAT GCG ATC TTT     195
```

```
TCG TTA TGC CAG GCT ATG AGT CTG TTT GCC AGT CGA CAA      234

ACG CTA TTG CTG TTG TTA CCA GAA AAC GGA CCG AAT GCG      273

GCG ATC AAT GAG CAA CTT CTC ACA CTC ACC GGA CTT CTG      312

CAT GAC GAC CTG CTG TTG ATC GTC CGC GGT AAT AAA TTA      351

AGC AAA GCG CAA GAA AAT GCC GCC TGG TTT ACT GCG CTT      390

GCG AAT CGC AGC GTG CAG GTG ACC TGT CAG ACA CCG GAG      429

CAG GCT CAG CTT CCC CGC TGG GTT GCT GCG CGC GCA AAA      468

CAG CTC AAC TTA GAA CTG GAT GAC GCG GCA AAT CAG GTG      507

CTC TGC TAC TGT TAT GAA GGT AAC CTG CTG GCG CTG GCT      546

CAG GCA CTG GAG CGT TTA TCG CTG CTC TGG CCA GAC GGC      585

AAA TTG ACA TTA CCG CGC GTT GAA CAG GCG GTG AAT GAT      624

GCC GCG CAT TTC ACC CCT TTT CAT TGG GTT GAT GCT TTG      663

TTG ATG GGA AAA AGT AAG CGC GCA TTG CAT ATT CTT CAG      702

CAA CTG CGT CTG GAA GGC AGC GAA CCG GTT ATT TTG TTG      741

CGC ACA TTA CAA CGT GAA CTG TTG TTA CTG GTT AAC CTG      780

AAA CGC CAG TCT GCC CAT ACG CCA CTG CGT GCG TTG TTT      819

GAT AAG CAT CGG GTA TGG CAG AAC CGC CGG GGC ATG ATG      858

GGC GAG GCG TTA AAT CGC TTA AGT CAG ACG CAG TTA CGT      897

CAG GCC GTG CAA CTC CTG ACA CGA ACG GAA CTC ACC CTC      936

AAA CAA GAT TAC GGT CAG TCA GTG TGG GCA GAG CTG GAA      975

GGG TTA TCT CTT CTG TTG TGC CAT AAA CCC CTG GCG GAC     1014

GTA TTT ATC GAC GGT TGA                                 1032
```

The underlined portions of this sequence refer to subunits which are δ-1 (55–117), δ-2 (358–399), and δ-3 (604–672). In addition, the upstream sequence:

```
CCGAACAGCT GATTCGTAAG CTGCCAAGCA TCCGTGCTGC GGATATTCGT    50

TCCGACGAAG AACAGACGTC GACCACAACG GATACTCCGG CAACGCCTGC   100

ACGCGTCTCC ACCACGCTGG GTAACTG                            127
``` wherein the last underlined TG denotes two-thirds of r1pB stop codon; in addition, the positive RNA polymerase promoter signals (TCGCCA and GATATT) and the Shine-Dalgarno sequence (ACGCT) are underlined.

In addition, the downstream nucleic acid sequence for holA is as follows:

```
TGA ATGAAATCT TTACAGGCTC TGTTTGGCGG CACCTTTGAT CCGGTGCACT      52

ATGGTCATCT AAAACCCGTT GGAAGCGTGG CCGAAGTTTT GATTGGTCTG AC     104
```

The holA gene translates into the amino acid sequence:

```
Met Ile Arg Leu Tyr Pro Glu Gln Leu Arg Ala Gln Leu Asn Glu
                5                   10                  15

Gly Leu Arg Ala Ala Tyr Leu Leu Leu Gly Asn Asp Pro Leu Leu
                20                  25                  30

Leu Gln Glu Ser Gln Asp Ala Val Arg Gln Val Ala Ala Ala Gln
                35                  40                  45

Gly Phe Glu Glu His His Thr Phe Ser Ile Asp Pro Asn Thr Asp
                50                  55                  60

Trp Asn Ala Ile Phe Ser Leu Cys Gln Ala Met Ser Leu Phe Ala
                65                  70                  75

Ser Arg Gln Thr Leu Leu Leu Leu Pro Glu Asn Gly Pro Asn
                80                  85                  90

Ala Ala Ile Asn Glu Gln Leu Leu Thr Leu Thr Gly Leu Leu His
                95                  100                 105

Asp Asp Leu Leu Leu Ile Val Arg Gly Asn Lys Leu Ser Lys Ala
                110                 115                 120

Gln Glu Asn Ala Ala Trp Phe Thr Ala Leu Ala Asn Arg Ser Val
                125                 130                 135

Gln Val Thr Cys Gln Thr Pro Glu Gln Ala Gln Leu Pro Arg Trp
                140                 145                 150

Val Ala Ala Arg Ala Lys Gln Leu Asn Leu Glu Leu Asp Asp Ala
                155                 160                 165

Ala Asn Gln Val Leu Cys Tyr Cys Tyr Glu Gly Asn Leu Leu Asn
                170                 175                 180

Leu Ala Gln Ala Leu Glu Arg Leu Ser Leu Leu Trp Pro Asp Gly
                185                 190                 195

Lys Leu Thr Leu Pro Arg Val Glu Gln Ala Val Asn Asp Ala Ala
                200                 205                 210

His Phe Thr Pro Phe His Trp Val Asp Ala Leu Leu Met Gly Lys
                215                 220                 225

Ser Lys Arg Ala Leu His Ile Leu Gln Gln Leu Arg Leu Gly Gly
                230                 235                 240

Ser Glu Pro Val Ile Leu Leu Arg Thr Leu Gln Arg Glu Leu Leu
                245                 250                 255

Leu Leu Val Asn Leu Lys Arg Gln Ser Ala His Thr Pro Leu Arg
                260                 265                 270

Ala Leu Phe Asp Lys His Arg Val Trp Gln Asn Arg Arg Gly Met
                275                 280                 285

Met Gly Glu Ala Leu Asn Arg Leu Ser Gln Thr Gln Leu Arg Gln
                290                 295                 300

Ala Val Gln Leu Leu Thr Arg Thr Glu Leu Thr Leu Lys Gln Asp
                305                 310                 315

Tyr Gly Gln Ser Val Trp Ala Glu Leu Gly Leu Ser Leu Leu
                320                 325                 330

Leu Cys His Lys Pro Leu Ala Asp Val Phe Ile Asp Gly
                335                 340             343
```

The holA gene is located in an area of the chromosome containing several membrane protein genes. They are all transcribed in the same direction. The mrdA and mrdB genes encode proteins responsible for the rod shape of *E. coli* and the rlpA and rlpB genes encode rare lipoproteins which are speculated to be important to cell duplication. The position of the δ gene within a cluster of membrane proteins may be coincidental or may be related to the putative attachment of the replisome to the membrane.

As noted, the termination codon of the rlpB protein overlaps one nucleotide with the initiating ATG of holA leaving a gap of only 2 nucleotides between these genes. holA may be an operon with rlpB or there may be a promoter within rlpB. The neatest possible initiation signals for transcription (the putative RNA polymerase signals) and translation (Shine-Dalgarno) are underlined in the sequence given above; the match to their respective consensus sequences is not strong suggesting a low utilization efficiency. Inefficient transcription and/or translation may be expected for a gene encoding a subunit of a holoenzyme present at only 10–20 copies/cell. The δ gene uses several rare codons [CCC(Pro), ACA(Thr), GGA(Gly), AGT(Ser), AAT(Asn), TTA, TTG, CTC(all Leu)] 2–5 times more frequently than average which may decrease translation efficiency. ATP binding to δ within the holenzyme has been detected previously by UV crosslinking. The DNA sequence of the δ shows a near match to the ATP binding site consensus motif (i.e. $AX_3GKS$ for δ at residues 219–225 compared to the published consensus $G/AX_4GKS/T$, $G/AXGKS/T$ or $G/AX_2GXGKS/T$ [see Nuc. Acids Res 17:8413 (1989)]. Whether δ binds with ATP specifically at this site remains to be determined. Of the 33 arginine and lysine residues in δ, 16 of them (50%) are within amino acids 225–307. This same region contains only 5 (14%) of the 35 glutamic and aspartic acid residues. Whether this concentration of basic residues is significant to function is unknown. There are no strong matches to consensus sequences to motifs encoding: zinc fingers or helix-loop-helix DNA binding domains.

The holA gene was cloned into M13mp18 and an NdeI site was created at the initiating methionine by the site directed mutagenesis technique in order to study the overproduction of this gene. The δ gene was then excised from M13delta and inserted into the NdeI site of the pET-3c expression vector [see Methods Enzymol 185:60 (1990)] which places δ under control of a strong T7 RNA polymerase promotor, see FIG. 3-1. Upon transformation into BL21(DE3) cells and induction of T7 RNA polymerase with IPTG, the δ protein was expressed to 27% total cell protein. For reasons unknown, δ was not produced in BL21(DE3) cells containing the pLysS plasmid. Induction at 25° C. yielded approximately 2-fold more δ and increased the solubility of the overproduced δ relative to induction at 37° C. Twelve liters of induced cells were lysed using lysozyme and 141 mg of pure δ was obtained in 28% overall yield upon column fractionation using Hexylamine Sepharose, Heparin Agarose, and Q Sepharose. Delta protein tended to precipitate upon standing in low salt (<70 mM), especially during dialysis. Therefore, low salt was avoided except for short periods of time and column fractions containing δ were sometimes diluted in preparation for the next column rather than dialyzed overnight. The δ subunit was assayed by its ability to reconstitute efficient replication of a singly primed M13mp18 ssDNA "coated" with SSB in the presence of α, ε, β, and γ subunits. Cell lysate prepared from induced cells containing pETdelta were more active in the replication assay than cell lysate prepared from induced cells containing the pET-3c vector.

The expressed δ protein comigrated with the authentic δ subunit contained within the γ complex of the holoenzyme. The N-terminal sequence analysis of the pure cloned δ was identical to that predicted from the holA sequence according to the present invention provided that the protein encoded by the gene had been purified. Furthermore, the overproduced δ subunit was active with only the α, ε, γ and β subunits of the holenzyme (FIG. 5-1). In the presence of a sixth subunit, δ', activity was enhanced. The amount of the cloned δ required to reconstitute the efficient DNA synthesis characteristic of the holoenzyme using the 5 or 6 subunit combination according to the present invention is in the range shown previously for the naturally purified δ resolved from the γ complex. As shown below, addition of more γ to the replication assay brings the amount of δ down even further to about 1 ng for a stoichiometry of about 1–2 δ monomers per DNA circle replicated.

Electrospray mass spectrometry of the cloned δ protein yielded a molecular mass of 38,704 da. This mass is within 0.0015 of the mass predicted from the gene; well within the 0.01% error of the mass spectrometry technique. This is evidence that the DNA sequence above according to the present invention contains no errors and indicates the overproduced δ is not modified during or after translation. The $\epsilon_{280}$ calculated from the amino acid composition of δ is 46,230 $M^{-1}cm^{-1}$. The measured absorbance of δ in 6M guanidine hydrochloride is only 0.2% higher than in buffer A. Hence, the $\epsilon_{280}$ of native δ is 46,137 $M^{-1}cm^{-1}$.

Further understanding of the individual subunits the present invention also determines whether δ and δ' are monomeric, dimeric or higher order structures. The δ and δ' subunits were also each analyzed in a gel filtration column, and they migrated in essentially the same position as one another (fractions 30–32). As discussed below the δ' appears as two proteins, $\delta'_L$ and $\delta'_S$, which differ by approximately 0.5 kda. Comparison with protein standards of known Stokes radius yielded a Stokes radius of 26.5 Å for δ and 25.8 Å for δ', slightly smaller than the 27.5 Å radius of the 43.5 kDa ovalbumin standard indicating both δ and δ' are both monomeric (their gene sequences predict: δ, 38.7 kDa δ', 36.9 kDa). In a glycerol gradient sedimentation analysis both δ and δ' migrated in the same position as one another with an S value of 3.0 relative to protein standards, a slightly lower sedimentation value than the 43.5 kda ovalbumin standard, again indicating a monomeric state for the δ and δ'. Besides protein mass, the protein shape is also a determinant of both the Stokes radius and the S value obtained by these techniques. The shape however, causes opposite behavior in these two techniques, a protein with an asymmetric shape behaves in gel filtration as a larger protein than if it were spherical (elutes early) and behaves in sedimentation like a smaller protein than if it were spherical (sediments slower). The Stokes radius and S value can be combined in the equation of Siegel and Monty whereupon the protein shape factor cancels. Therefore, the native mass of the protein obtained from such treatment is more accurate than calculating the mass from only the S value or the Stokes radius and assuming a spherical shape. This calculation yielded a native mass of 34.7 kDa for δ and 33.8 kDa for δ'; values similar to the monomer molecular mass predicted from the gene sequences of δ and δ', further evidence they are monomers. Their frictional coefficients are each significantly greater than 1.0 indicating they are not spherical but have some asymmetry to their shape. One can also conclude from this work that the two δ' subunits are a mixture of $\delta'_L$ and $\delta'_S$ rather than a complex of $\delta'_L$ and $\delta'_S$.

In initial studies using the cloned δ, δ forms only a weak complex with γ but, together with δ' a stable γδδ' complex can be reconstituted which remains intact in gel filtration and ion exchange chromatography. Likewise, δ' forms only a weak complex with γ, and requires the δ subunit to bind γ tightly. Both δ and δ' appear monomeric and bind to each other to form a δδ' heterodimer.

Availability of the δ subunit in large quantity will allow detailed studies of the mechanism of the γ complex in β clamp formation. Further, identification of the δ gene will provide for genetic analysis (essentiality) of δ in E. coli replication and possibly other roles of δ in DNA metabolism.

The second subunit according to the present invention, that of δ', was also identified from the δ' fraction in like manner. The N-terminal sequence, comprising the first 18 amino acids in the peptide, and the tryptic peptide sequence were obtained. The amino acid sequence determined from the initial sequence studies for the δ' peptide is:

```
Met Arg Trp Tyr Pro Trp Leu Arg Pro Asp Phe Glu Lys Leu Val
                 5               10              15
Ala Ser Tyr Gln Ala Gly Arg Gly His His Ala Leu Leu Ile Gln
                20              25              30
Ala Leu Pro Gly Met Gly Asp Asp Ala Leu Ile Tyr Ala Leu Ser
                35              40              45
Arg Tyr Leu Leu Cys Gln Gln Pro Gln Gly His lys Ser Cys Gly
                50              55              60
His Cys Arg Gly Cys Gln Leu Met Gln Ala Gly Thr His Pro Asp
                65              70              75
Tyr Tyr Thr Leu Ala Pro Glu Lys Gly Lys Asn Thr Leu Gly Val
                80              85              90
Asp Ala Val Arg Glu Val Thr Glu Lys Leu Asn Glu His Ala Arg
                95              100             105
Leu Gly Gly Ala Lys Val Val Trp Val Thr Asp Ala Ala Leu Leu
                110             115             120
Thr Asp Ala Ala Ala Asn Ala Leu Leu Lys Thr Leu Glu Glu Pro
                125             130             135
Pro Ala Glu Thr Trp Phe Phe Leu Ala Thr Arg Glu Pro Glu Arg
                140             145             150
Leu Leu Ala Thr Leu Arg Ser Arg Cys Arg Leu His Tyr Leu Ala
                155             160             165
Pro Pro Pro Glu Gln Tyr Ala Val Thr Trp Leu Ser Arg Glu Val
                170             175             180
Thr Met Ser Gln Asp Ala Leu Leu Ala Ala Leu Arg Leu Ser Ala
                185             190             195
Gly Ser Pro Gly Ala Ala Leu Ala Leu Phe Gln Gly Asp Asn Trp
                200             205             210
Gln Ala Arg Glu Thr Leu Cys Gln Ala Leu Ala Tyr Ser Val Pro
                215             220             225
Ser Gly Asp Trp Tyr Ser Leu Leu Ala Ala Leu Asn His Glu Gln
                230             235             240
Ala Pro Ala Arg Leu His Trp Leu Ala Thr Leu Leu Met Asp Ala
                245             250             255
Leu Lys Arg His His Gly Ala Ala Gln Val Thr Asn Val Asp Val
                260             265             270
Pro Gly Leu Val Ala Glu Leu Ala Asn His Leu Ser Pro Ser Arg
                275             280             285
Leu Gln Ala Ile Leu Gly Asp Val Cys His Ile Arg Glu Gln Leu
                290             295             300
Met Ser Val Thr Gly Ile Asn Arg Glu Leu Leu Ile Thr Asp Leu
                305             310             315
Leu Leu Arg Ile Glu His Tyr Leu Gln Pro Gly Val Val Leu Pro
                320             325             330
Val Pro His Leu
         334
```

From these sequences, two DNA oligonucleotide probes were made and used (after end-labelling with $^{32}$P for use in Southern blot analysis) to probe a Southern blot of *E. coli* DNA which was grown, isolated and restricted as above. The sequences of the two probes were:

```
probe 1:
ACT CTG GAA GAA CCG CCG GCT GAA ACT TGG TTT TTT CTG GCT    42

ACT CGT GAA CCG GAA                                         57; and probe 2:
GCT GGT TCT CCG GGT GCT GCT CTG GCT CTG TTT CAG GGT GAT    42

GAC TGG CAG GCT                                             54.
```

Of the two Southern blots analyzed (one with the 57-mer probe and the other with the 54-mer probe), the patterns from the blots had one set of bands in common, and these were sized by comparison with size standards in the same gel following recognized techniques. The size of these 8 common "band" or DNA fragments produced by digestion with 8 restriction enzymes were used to scan, by eye, the restriction map of the *E. coli* genome [see Cell 50:495 (1987)]. One unique location on the genome was located which was compatable with all 8 restriction fragment sizes.

Phage $\lambda_{236}$ was selected as a phage containing the "unique location" in the *E. coli* genome. The δ' gene was excised from the $\lambda_{236}$ phage using restriction enzymes EcoRV and KpnI to yield a 2.3 kb fragment of DNA. This fragment was then ligated into pUC18 and sequenced using a sequenase kit (US Biochemicals) in accordance with the manufacturer's instructions. The fragment was also ligated into a M13mp18 vector for making a site specific mutation, as described above, at the ATG start codon (i.e., changing the CGCATG to CATATG; thereby allowing NdeI to cleave the nucleotide at CATATG, whereas it could not cleave the nucleotide using the normal CGCATG sequence).

The nucleic acid sequence obtained from these studies predicted the amino acid sequence determined for δ' peptide in frame, and thus the selected sequence was that for the δ' gene. The nucleic acid sequence, according to the present invention, for this second subunit, δ', is:

```
ATG AGA TGG TAT CCA TGG TTA CGA CCT GAT TTC GAA AAA         39

CTG GTA GCC AGC TAT CAG GCC GGA AGA GGT CAC CAT GCG         78

CTA CTC ATT CAG GCG TTA CCG GGC ATG GGC GAT GAT GCT        117

TTA ATC TAC GCC CTG AGC CGT TAT TTA CTC TGC CAA CAA        156

CCG CAG GGC CAC AAA AGT TGC GGT CAC TGT CGT GGA TGT        195

CAG TTG ATG CAG GCT GGC ACG CAT CCC GAT TAC TAC ACC        234

CTG GCT CCC GAA AAA GGA AAA AAT ACG CTG GGC GTT GAT        273

GCG GTA CGT GAG GTC ACC GAA AAG CTG AAT GAG CAC GCA        312

CGC TTA GGT GGT GCG AAA GTC GTT TGG GTA ACC GAT GCT        351

GCC TTA CTA ACC GAC GCC GCG GCT AAC GCA TTG CTG AAA        390

ACG CTT GAA GAG CCA CCA GCA GAA ACT TGG TTT TTC CTG        429

GCT ACC CGC GAG CCT GAA CGT TTA CTG GCA ACA TTA CGT        468

AGT CGT TGT CGG TTA CAT TAC CTT GCG CCG CCG CCG GAA        507

CAG TAC GCC GTG ACC TGG CTT TCA CGC GAA GTG ACA ATG        546

TCA CAG GAT GCA TTA CTT GCC GCA TTG CGC TTA AGC GCC        585

GGT TCG CCT GGC GCG GCA CTG GCG TTG TTT CAG GGA GAT        624

AAC TGG CAG GCT CGT GAA ACA TTG TGT CAG GCG TTG GCA        663

TAT AGC GTG CCA TCG GGC GAT TGG TAT TCG CTG CTA GCG        702

GCC CTT AAT CAT GAA CAA GTC CCG GCG CGT TTA CAC TGG        741

CTG GCA ACG TTG CTG ATG GAT GCG CTA AAA CGC CAT CAT        780

GGT GCT GCG CAG GTG ACC AAT GTT GAT GTG CCG GGC CTG        819

GTC GCC GAA CTG GCA AAC CAT CTT TCT CCC TCG CGC CTG        858

CAG GCT ATA CTG GGG GAT GTT TGC CAC ATT CGT GAA CAG        897

TTA ATG TCT GTT ACA GGC ATC AAC CGC GAG CTT CTC ATC        936
```

```
                                           -continued
ACC GAT CTT TTA CTG CGT ATT GAG CAT TAC CTG CAA CCG          975

GGC GTT GTG CTA CCG GTT CCT CAT CTT                          1002
```

The underlined portions of this sequence refer to subunits which are δ'-1 (283–315), δ'-2 (316–327), δ'-3 (328–390), δ'-4 (391–462), δ'-5 (481–534), and δ'-6 (577–639). In addition, the upstream sequence:

```
AAGAATCTTT CGATTTCTTT AATCGCACCC GCGCCCGCTA TCTGGAACTG    50

GCAGCACAAG ATAAAAGCAT TCATACCATT GATGCCACCC AGCCGCTGGA   100

GGCCGTGATG GATGCAATCC GCACTACCGT GACCCACTGG GTGAAGGAGT   150

TGGACGC                                                  157
``` contains an underlined putative translational signal: Shine-Dalgarno.

In addition, the downstream nucleic acid sequence for δ' begins with a stop codon:

```
TTA GAGAGACATC ATGTTTTTAG TGGACTCACA CTGCCATCTC             43

GATGGTCTGG ATTATGAATC TTTGCATAAG GACGTGGATG ACGTTCTGGC      93

GAAAGCCGCC GCACGCGATG TGAAATTTTG TCTGGCAGTC GCCACAACAT     143
```

The δ' gene (holB) was then subcloned into M13mp18, and a NdeI site was created at the initiating codon as described above. The δ' gene was then excised from M13 using NdeI restriction enzyme and a second enzyme which cut downstream of δ', and the excised gene was subcloned into the pET-3c overexpression plasmid using the same techniques described above. Following overexpression of the δ' protein, the protein was purified using a Fast flow Q-Heparin-Hexylamine technique as described herein. Ninety mg of δ' protein was obtained from 4 liters of cells.

Further studies on the δ' gene were conducted to make certain that the gene sequence obtained from these research was actually the δ' gene and not some artifact. These studies showed that the gene sequence according to the present invention predicted all the peptide sequence information, that the cloned δ' gene comigrates with the naturally occurring gene on a 13% SDS-PAG gel, that the cloned δ' gene stimulates the 5 protein system as does the naturally occurring δ', and that δ' forms a δ'δ complex with δ in a similar manner to that which occurs with the naturally occurring δ' and δ.

With specific regard to the isolation and characterization of δ' and holB according to the present invention, the amino acid sequencing was conducted using δ and δ' subunits purified to apparent homogenicity through the ATP-agarose column step [see J. Biol. Chem. 265:1179 (1990)] from 1.3 kg of the γ/τ overproducing strain of E. coli: HB101 (pNT203, pSK100), [see J. Biol. Chem. 263:6555 (1988)]. The δ and δ' subunits were separated on a 13% SDS polyacrylamide gel whereupon the δ' resolved into two bands. The slower and faster migrating δ' bands are referred to as $δ'_L$ (large) and $δ'_S$ (small), respectively; $δ'_S$ was approximately 2 times the abundance of $δ'_L$. Both $δ'_L$ and $δ'_S$ were electroblotted onto PVDF membrane (Whatman) [see J. Biol. Chem. 262:10035 (1987)] for N-terminal sequencing (50 pmol each of $δ'_L$ and $δ'_S$), and onto nitrocellulose membrane (Schleicher and Schuell) [see Proc. Natl. Acad. Sci. USA 84:6970 (1987)] for tryptic analysis (90 pmol of $δ'_L$ and 180 pmol of $δ'_S$). Proteins were visualized by Ponceau S stain (Sigma).

Analysis of the more abundant $δ'_S$ was as follows: the N-terminal sequence was:

```
NH2-Met Arg Trp Tyr Pro Pro Leu (Arg)(Pro) Asp Phe
                    5                          10
Glu Lys Leu Val Ala
                15
``` and the tryptic peptides were:

```
δ'-1:
NH2-Glu Val Thr Glu Lys Leu Asn Glu His Ala Arg;
                   5                    10

δ'-3:
NH2-Val Val Trp Val Thr Asp Ala Ala Leu Leu Thr Asp
                    5                        10

Ala Ala Ala Asn Ala Leu Leu Lys
              15               20;

δ'-4:
NH2-Thr Leu Glu Glu Pro Pro Ala Glu Thr Trp Phe Phe Leu Ala
```

-continued

```
Thr Arg Glu Pro (Glu) (Arg) Leu Leu Ala Thr(Leu);
 15                  20

δ'-5:
NH₂-Leu His Tyr Leu Ala Pro Pro (Pro) Glu Gln Tyr Ala Val
                  5                      10

Thr (Trp) Leu Ser Arg; and
           15

δ'-6:
NH₂-Leu Ser Ala Gly Ser Pro Gly Ala Ala Leu Ala Leu Phe Gln
                  5                      10

Gly Asp Asn Trp Gln Ala Arg.
 15              20
```

Sequence analysis of tryptic peptides of the less abundant δ'L were:

```
δ'-2:
NH₂-Leu Gly Gly Ala Lys; and
                  5

δ'-7 (same as δ'-3):
NH₂-Val Val Trp Val Thr Asp Ala Ala Leu Leu Thr Asp
                  5                      10

Ala Ala Ala Asn Ala Leu Leu Lys
         15              20;
```

Parenthesis in the above sequences indicate uncertain assignments.

Two synthetic oligonucleotide probes (DNA oligonucleotides, Oligos etc. Inc.) were designed from the sequence of two of the tryptic peptides and the codon usage of E. coli with allowance for a T-G mispair at the wobble position. A synthetic DNA 57-mer probe was based on the sequence of δ'-4 (amino acids 131–149):

```
Ala Cys Thr Cys Thr Gly Gly Ala Ala Gly Ala Ala Cys Cys Gly
                  5                      10              15

Cys Cys Gly Gly Cys Thr Thr Gly Ala Ala Ala Cys Thr Thr Gly
                 10                      25              30

Gly Thr Thr Thr Thr Thr Thr Cys Thr Gly Gly Cys Thr Ala Cys
                 35                      40              45

Thr Cys Gly Thr Gly Ala Ala Cys Cys Gly Gly Ala Ala
                 50                      55
```

(after identification and sequencing of holB this probe was incorrect at 11 positions). A DNA 54-mer probe was based on the sequence of δ'-6 (amino acids 195–212):

```
Gly Cys Thr Gly Gly Thr Thr Cys Thr Cys Cys Gly Gly Gly Thr
                  5                      10              15

Gly Cys Thr Gly Cys Thr Cys Thr Gly Gly Cys Thr Cys Thr Gly
                 20                      25              30

Thr Thr Thr Cys Ala Gly Gly Thr Gly Ala Thr Ala Ala Cys
                 35                      40              45

Thr Gly Gly Cys Ala Gly Gly Cys Thr
                 50
```

(after identification and sequencing of holB the probe was incorrect at 9 positions. These probes (100 pmol each) were 5' end-labelled with 1 μM [γ³²P]ATP (radionucleotides, Dupont-New England Nuclear) and polynucleotide kinase. E. coli genomic DNA (strain C600) was extracted [see J. Mol. Bio. 3:208 (1961)] and restricted with either BamHI, HindIII, EcoRI, EcoRV, BglI, KpnI, PstI or PvuII (DNA modification enzymes, New England Biolabs) and then each digest was electrophoresed in a 0.8% native agarose gel followed by depurination (0.25 M HCl), denaturation (0.5 M NaCl) and then neutralized (1 M Tris, 2 M NaCl, pH %.0) prior to transfer to Gene Screen Plus (DuPont-New England Nuclear) for Southern analysis using a Vacugene apparatus (Pharmacia) in the presence of 2×SSC (0.3 M NaCl, 0.3M sodium acetate, pH 7.0). Conditions for hybridization and washing using these oligonucleotide probes were determined empirically and the desired results were obtained using a hybridization temperature of 42° C. then washing with 2×SSC and 0.2% SDS at successively higher temperature until evaluation by autoradiography showed a single band in each lane for the 57-mer, and two bands in each lane for the 54-mer (this occurred at 53° C. for both probes).

Although the 54-mer showed two bands in each lane, one band always matched the position of the band probed with the 57-mer.

The 2.1 kb KpnI/EcoRV fragment containing holB was excised from λ E9G1(236) [see Cell 50:495(1987)] and directionally ligated into PUC18 (KpnI/HincII) to yield pUC-δ'. Both strands of DNA were sequenced by the chain termination method of Sanger using the United States Biochemicals sequenase kit, [α-$^{35}$S]dATP, and synthetic DNA 18-mers.

A 2.1 kb KpnI/HindIII fragment containing the holB gene was excised from pUC-δ' and directionally ligated into M13mp18 to yield M13-δ'. An NdeI site was generated at the start codon of holB by oligonucleotide site directed mutagenesis [see Methods Enzymol 154:367 (1987)] using a DNA 33-mer:

```
Gly Gly Thr Gly Ala Ala Gly Gly Ala Gly Thr Thr Gly Gly Ala
            5                   10                  15
Cys Ala Thr Ala Thr Gly Ala Gly Ala Thr Gly Gly Thr Ala Thr
            20                  25                  30
Cys Cys Ala
``` containing the NdeI site (underlined) at the start codon of holB to prime replication of M13-δ' viral ssDNA and using SSB and DNA polymerase III holoenzyme (in place of DNA polymerase I) to replicate the circular template without strand displacement. The M13 chimera is called M13-δ'-NdeI. And NdeI fragment (1160 bp) containing the holB gene was excised from M13-δ'-NdeI and ligated into pET3c, linearized using NdeI, to yield pET-δ'. The orientation of the holB gene in pET-δ' was determined by sequencing.

Reconstitution assays contained 108 ng M13mp18 ssDNA (0.05 pmol as circles) uniquely primed with a DNA 30-mer [see J. Biol. Chem 266:11328 (1991)], 1.5 μg SSB (21 pmol as tetramer), 30 ng β (0.39 pmol as dimer), 22.5 ng αε complex (0.14 pmol), 20 ng γ (0.12 pmol as dimer), 2 ng δ (0.5 pmol as monomer) and the indicated amount of δ' (or 1–5 ng of column fraction during purification) in 20 mM Tris-HCl (pH 7.5), 8 mM MgCl$_2$, 5 mM DTT, 4% glycerol, 40 μg/ml BSA, 0.5 mM ATP, 60 μM dGTP, and 0.1 mM EDTA in a final volume of 25 μl (after the addition of the remaining proteins). Assays of γ or τ activity with either δ, δ' or δδ', contained either 2 ng δ (0.05 pmol as monomer), 2 ng δ' (0.05 pmol as monomer), or 1 ng (0.025 pmol) each of δ and δ', and the indicated amount of γ or τ. All proteins were added to the assay on ice and then shifted to 37° C. for 8 minutes to allow reconstitution of the pocessive polymerase on the primed ssDNA. DNA synthesis was initiated upon rapid addition of 60 μM dATP and 20 μM [a$^{32}$P]TTP, then quenced after 20 seconds and quantitated using DE81 paper. When needed, proteins were diluted in 20 mM Tris-HCl (pH 7.5), 2 mM DTT, 0.5 mM EDTA, 20% glycerol, and 50 μg/ml BSA. Proteins used in the reconstitution assays were purified [see J. Biol. Chem 266:9833 (1991). The concentration of β and δ were determined by absorbance using an ε$_{280}$ value if 17,900 M$^{-1}$cm$^{-1}$, and 46,137 M$^{-1}$cm$^{-1}$, respectively. Concentrations of α, ε, γ, τ and SSB were then determined [see Anal. Biochem 72:248 (1976)] using BSA as a standard. The concentration of δ' was determined by absorbance using an ε$_{280}$ value of 60,136 M$^{-1}$cm$^{-1}$.

ATPase assays were performed in a final volume of 20 μl containing 20 mM Tris-HCl (pH 7.5), 8 mM MgCl$_2$ and contained 285 ng M13mp18 ssDNA. ATPase assays of γ, δ, δ' δδ', γδ and γδ' with and without β contained 100 μM [(γ-$^{32}$P] ATP and when present 376 ng γ (4 pmol as dimer), 304 ng δ (7 pmol as monomer), 296 ng δ' (8.0 pmol as monomer), and 320 ng β (4.2 pmol as dimer). Proteins were added on ice, shifted to 37° C. for 30 minutes, then 0.5 ml was spotted on a plastic backed thin layer of chromatography (TLC) sheet coated with Cel-300 polyethyleneimine (Brinkman Instruments Co.). To assay the more active ATPase activity of γδδ' and τ, 300 μM ATP was used, less total protein and less time at 37° C. in order to assess the initial rate of reaction. Therefore, ATPase assays of γδδ, τ, τδ, τδ' and τδδ' with and without β contained 300 mM [γ-$^{32}$P] ATP and when present, 47 ng γ (0.5 pmol as dimer), 71 ng τ (0.5 pmol as dimer), 38 ng δ (1 pmol as monomer), 37 ng δ' (1 pmol as monomer) and 40 ng β (0.5 pmol as dimer. Proteins were added on ice, shifted to 37° C. for 10 minutes, then analyzed by TLC as described above.

TLC sheets were developed in 0.5 M lithium chloride, 1 M formic acid. An autoradiogram of the TLC chromatogram was used to visualize the free phosphate at the solvent front and ATP at the origin which were then cut from the TLC sheet and quantitated by liquid scintillation. The amount of ATP hydrolyzed was calculated as the percent of total radioactivity located at the solvent front (P$_i$) times the total moles of ATP added to the reaction.

The results of the δ' studies appear below:

The naturally purified δ' (resolved from the γ complex) appears in a 13% SDS polyacrylamide gel as two bands of approximately 37 kDa that differ in size by about 1 kDa. The larger protein (δ'$_L$) is approximately one half the abundance of the smaller one (δ'$_S$). Both δ'$_L$ and δ'$_S$ are believed encoded by the same gene as there was no noticeable difference in their HPLC profiles upon digestion with trypsin. In support of this, peptides from δ'$_S$ and δ'$_L$ that had the same retention time on HLPC analysis also had identical amino acid sequences (peptide δ'-7 from δ'$_S$ and δ'-3 from δ'$_L$ were identical). The N-terminus of δ'$_S$ and live tryptic peptides of δ'$_S$ and two tryptic peptides of δ'$_L$ were sequenced.

A search of the GenBank revealed no match to the N-terminal sequence or to any of the tryptic peptides from either δ'$_L$ or δ'$_S$. Two best-guess oligonucleotide probes (a 57-mer and a 54-mer) were designed from tryptic peptides δ'-4 and δ'-6 based on the codon usage frequency in E. coli [see PNAS USA 80:687 (1983)]. The oligonucleotide probes were used in a Southern analysis of E. coli genomic DNA digested with each of the eight Kohara restriction map enzymes. Imposing the restraint that the eight restriction fragments from the Southern analysis must overlap the holB gene, the Kohara map of the E. coli chromosome was searched and only one position of overlap at 24.3 minutes (1.174 kb on the E. coli chromosome starting from thrA) was found which satisfied the fragment sizes. The fragment sizes in the Kohara map and from the Southern analysis are given in the following table which depicts the correspondence of the observed size of genomic DNA restriction fragments with the Kohara restriction map of the E. coli chromosome in the region of 24 minutes. E. coli genomic DNA was digested with the restriction enzymes indicated. The size of the restriction fragments that were in common for both the 57-mer and 54-mer probes in the Southern analysis and also the corresponding sizes of the restriction fragments on the Kohara restriction map of the *E. coli* chromosome at 24.5 minutes are listed below.

| | Restriction | Size of restriction fragment (kb) |
|---|---|---|
| enzyme | Southern | Kohara map |
| PstI | 1.7 | 1.9 |
| BglI | 4.25 | 4.2 |
| KpnI | 6.6 | 6.4 |
| EcoRV | 7.0 | 6.8 |
| PvuII | 6.2 | 6.2 |
| EcoRI | >15 | 16.2 |
| HindIII | >20 | 30 |
| BamHI | >25 | 38 |

The Kohara λ phage E9G1(236) contains 16.2 kb of DNA surrounding the putative holB gene. A 2.1 KpnI/EcoRV fragment containing holB was excised from λ E9G1(236), cloned into pUC18 and sequenced. The sequence of the KpnI/EcoRV fragment revealed an open reading frame of 1002 nucleotides which predicts a 334 amino acid protein of 36.9 kDa (predicted pI of 7.04), consistent with the mobility of δ' in a SDS polyacrylamide gel. The open reading frame encodes the N-terminal sequence and all six tryptic peptide sequences obtained from $δ'_L$ and $δ'_S$.

Analysis of the DNA sequence upstream of the open reading frame revealed a putative translation initiation signal (Shine-Dalgarno sequence) 8 nucleotides upstream of the ATG initiating codon. No obvious transcription initiation signals were detected upstream of the initiation codon leaving open the possibility that holB is in an operon with an upstream gene(s). Alternatively, the transcription initiation signals may poorly match the consensus signals and thereby be unrecognizable, as a low level of transcription would not be unexpected for a gene encoding a subunit of the holoenzyme present at only 10–20 copies/cell. The holB, gene uses several rare codons [TTA (Leu), ACA (Thr), GGA (Gly), AGC, TCG (Ser)] 2–4 times more frequently than average which may decrease translation efficiency.

The holB sequence contains a helix-turn-helix consensus motif (Ala/GlyX$_3$GlyX$_5$Ile/Val) at Ala$_{80}$Gly$_{84}$Val$_{90}$ although ability of δ' to bind DNA has yet to be examined. There is also a possible leucine zipper (Leu$_7$X$_6$Leu$_{14}$X$_6$Gly$_{21}$X$_6$Leu$_{28}$) in the N-terminus although Gly interrupts the Leu pattern. The holB sequence does not contain consensus sequences for motifs encoding an ATP-binding site or a zinc finger. The molar extinction coefficient of δ' calculated from its 8 Trp and 11 Tyr residues is 59,600 $M^{-1}cm^{-1}$ which is only 0.9% lower than that observed in the presence of 6M guanidine hydrochloride for a native extinction coefficient of 60,136 $M^{-1}cm^{-1}$.

To obtain the δ' subunit in large quantity, an expression plasmid was constructed. The holB gene was first cloned into M13mp18 followed by site directed mutagenesis to create an NdeI site at the initiating methionine to allow precise subcloning of holB into the pET3c expression vector. The holB gene was excised from the M13-δ'-NdeI mutant using NdeI followed by insertion into the NdeI site of the pET3c expression vector [see Methods Enzymol 185:60 (1990)] which places holB under the control of the T7 RNA polymerase promotor of T7 gene and the efficient Shine-Dalgarno sequence of gene 10. The pET-δ' construct was transformed into BL21(DE3)plysS cells which harbor a λ lysogen containing the T7 RNA polymerase gene controlled by the lac UV5 promoter. Upon induction of T7 RNA polymerase with IPTG, the δ' protein was expressed to 50% of total cell protein. Cell lysate prepared from the induced cells containing pET-δ' was 5600-fold more active in the replication assays than cell lysate prepared from induced cells containing the pET3c vector as described below.

Three hundred liters of BL21(DE3)plysS cells harboring pET-δ' were grown at 37° C. in LB media supplemented with 5 mg/ml glucose, 10 μg/ml thiamine, 50 μg/ml thymine containing 100 μg/ml ampicillin and 25 μg/ml chloramphenicol. Upon growth to an $OD_{600}$ of 0.6, IPTG was added to 0.2 mM. After further growth for two hours the cells (940 g) were collected by centrifugation, resuspended in an equal weight of 50 mM Tris-HCl (pH 7.5), 10% sucrose (Tris-Sucrose) and stored at −70° C. 100 g of cells (30 liters of cell culture) were thawed whereupon they lysed (due to lysozyme produced by plysS) and to this was added 250 ml Tris-Sucrose, DTT to 2 mM and 40 ml of 10×heat lysis buffer (50 mM, Tris-HCl (pH 7.5), 10% sucrose, 0.3M spermidine, 1M NaCl). The cell debris was removed by centrifugation to yield the cell lysate (Fraction I, 4.41 g in 325 ml). The purification steps that followed were performed at 4° C. The reconstitution activity assay for δ' is as described previously. Ammonium sulphate (0.21 g/ml) was dissolved in the clarified cell lysate and stirred for 90 minutes. The precipitated protein containing δ' was pelleted (Fraction II, 1.58 g) and redissolved in 660 ml of 30 mM Hepes-NaOH (pH 7.2), 10% glycerol, 0.5 mM EDTA, 2 mM DTT (buffer A) and dialyzed against two successive changes of 2 liters each of buffer A to a conductivity equal to 40 mM NaCl. The Fraction II was loaded onto a 300 ml heparin agarose column (BioRad) equilibrated with buffer A. The heparin column was washed with 450 ml buffer A plus 20 mM NaCl, then eluted over a period of 14 hours using a 2.5 liter linear gradient of 20 mM NaCl to 300 mM NaCl in buffer A. One hundred fractions were collected. Fractions 36–53 were pooled (Fraction III, 550 ml, 990 mg) and dialyzed twice against 2 liters of 20 mM Tris-HCl (pH 7.5), 10% glycerol, 0.5 mM EDTA, 2 mM DTT (buffer B) to a conductivity equal to 60 mM NaCl. The Fraction III was loaded onto a 100 ml Q sepharose column (Pharmacia) equilabrated with buffer B. The loaded Q sepharose column was washed with 150 ml of buffer B plus 20 mM NaCl then eluted over a period of 12 hours using a 2 liter linear gradient of 20 mM NaCl to 300 mM NaCl in buffer B. Eighty fractions were collected. Fractions 34–56 were pooled (Fraction IV, 781 mg in 370 ml) and dialyzed twice against 2 liters each of buffer B to a conductivity equal to 60 mM NaCl just prior to loading onto a 60 ml EAH sepharose column (Pharmacia) that was equilabrated with buffer B. The loaded EAH sepharose column was washed with 60 ml of buffer B plus 40 mM NaCl then eluted over a period of 10 hours using a 720 ml linear gradient of 40 mM NaCl to 500 mM NaCl in buffer B. Eighty fractions were collected. Fractions 18–30 (Fraction V, 732 mg in 130 ml), which contained homogeneous δ' were pooled and dialyzed against 2 L buffer B (lacking DTT to allow an absorbance measurement, see below) to conductivity of 40 mM NaCl. Fraction V was passed over a 5 ml ATP-agarose column (Pharmacia, Type II, N-6 linked) to remove any γ complex contaminant followed by addition of DTT to 2 mM and then was aliquoted and stored at −70° C. Protein concentration was determined using BSA as a standard except at the last step in which concentration was determined by absorbance using $ε_{280}$=60,136 $M^{-1}cm^{-1}$.

| Step | | total protein | total units[1] (mg) | specific activity | fold purification (units/mg) | % yield |
|---|---|---|---|---|---|---|
| I | Lysate[2,3] | 4414 | $3.0 \times 10^1$ | $7 \times 10^6$ | 1.0 | 100 |
| II | Ammonium Sulfate | 1584 | $2.5 \times 10^{10}$ | $16 \times 10^6$ | 2.3 | 83 |
| III | Heparin | 990 | $2.6 \times 10^{10}$ | $26 \times 10^6$ | 3.7 | 87 |
| IV | Q Sepharose | 781 | $2.6 \times 10^{10}$ | $33 \times 10^6$ | 4.7 | 87 |
| V | EAH-Sepharose[4] | 732 | $2.5 \times 10^{10}$ | $34 \times 10^6$ | 4.9 | 83 |

[1] One unit is defined as pmol nucleotide incorporated in 20 seconds
[2] Lysate of BL21(DE3)plysS cells harboring the pET3c vector yielded a specific activity of 1252 units/mg.
[3] Omission of γ and δ from the assay of the lysate resulted in a 7650-fold reduction of specific activity (915 units/mg).
[4] Using pure δ', omission of γ from the assay gave no detectable synthesis under the conditions of the assay.

The purified overproduced δ' stimulated γδ 30-fold in its action in reconstituting the processive holoenzyme from the αε polymerase and the β clamp accessory protein. In this assay the δ' is titrated into a reaction containing a low concentration of γ and δ and also contains the β subunit, αε polymerase and M13mp18 ssDNA primed with a synthetic olignucleotide and coated with SSB. The proteins were preincubated with the DNA for 8 minutes to allow time for the accessory proteins to form the preinitiation complex which contains the β clamp and for αε to bind the preinitiation complex. DNA synthesis is initiated upon addition of deoxyribonucleoside triphosphates and the reaction is stopped after 20 seconds which is sufficient time for the processive reconstituted polymerase to complete the circular DNA. Although a processive polymerase can be reconstituted without the δ' subunit, under the conditions used in the present invention in which γ and δ are at low concentration, the δ' subunit stimulates the reaction greatly (30-fold). The δ' subunit saturated this assay at a level of approximately one molecule of δ' to one molecule of δ.

Figure 6B:
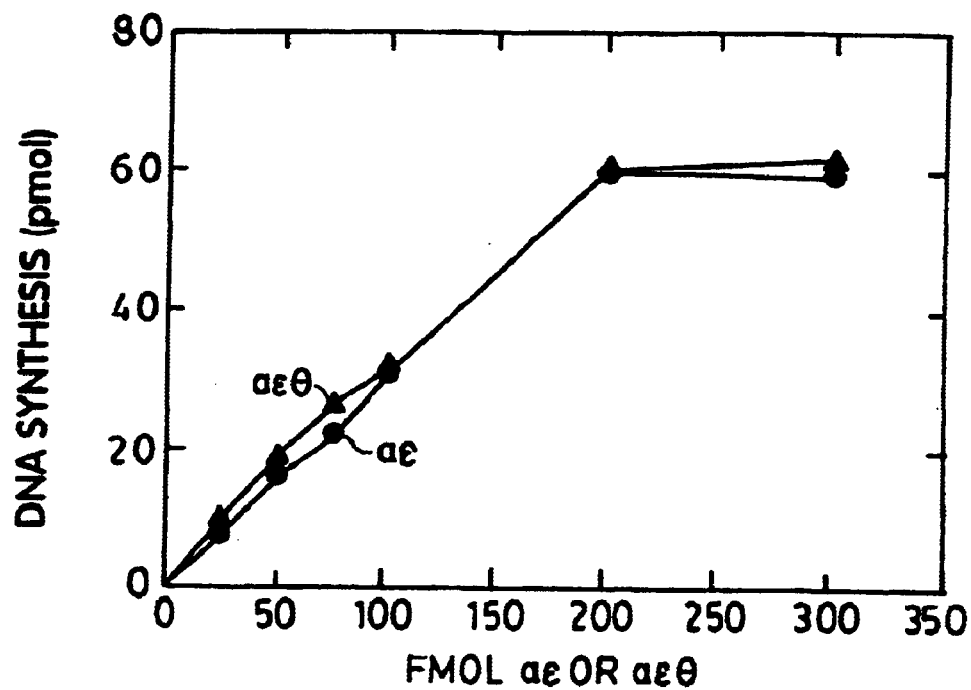

Both the τ and γ subunits of the holoenzyme are encoded by the same gene (dnaX). The γ subunit is formed as a result of a −1 frameshift during translation with the result that γ is only ⅔ the length of τ due to an earlier translational stop codon (within 2 codons) in the −1 reading frame. The activity of the γ and τ proteins in reconstituting the processive polymerase was compared using either the δ, δ' or both δδ' subunits in the presence of αε complex and β subunit (FIG. 6A and 6B). In the absence of δ and δ', the γ subunit alone displays insignificant activity in the reconstitution assay although when a large amount of γ was present it had very little, but detectable, activity (FIG. 6A). The δ subunit provides γ with activity in the reconstitution assay, but δ' does not provide γ with activity. However, the cloned δ' subunit, when present with δ, markedly stimulated the activity of the γ and δ mixture such that maximal activity was achieved at much lower concentrations of added γ.

The τ subunit alone, like γ, was also essentially inactive in the reconstitution assay, although at very high amounts of τ a slight, but reproducible amount of activity was observed. τ is active with δ in this assay although more τ (50-fold) than γ is needed for comparable activity. Previously it was observed that τ was unlike γ in that τ was active with δ' in the reconstitution assay in the absence of any δ subunit (only τ, δ' and α, ε, β were needed). Consistent with these previous results, the δ' subunit is active with τ in the absence of δ (similar to the activity of τ and δ in the absence of δ'). With both δ and δ' present, only a small amount of τ subunit is required for maximal activity in the reconstitution assay. The activity of τδδ' parallels that of γδδ' and requires 500-fold less τ for maximal activity than either τδ or τδ'. Hence, both the γ subunit and the τ subunit are highly active in this reconstitution assay when both δ and δ' are present.

The effect of the δ, δ' and β subunits on the DNA dependent ATPase activity of τ was quite different from their effect on γ, the close relative of the τ subunit. The τ subunit, by itself, is a much more active DNA dependent ATPase than γ and, in fact turns over two times more ATP than the γδδ' complex. Unlike the γ ATPase, the τ ATPase was essentially unaffected, by δ or by δ with or without β or by δ' with or without β. However, like the γ ATPase, the presence of both δ and δ' stimulated the τ ATPase, although the effect was only 4-fold compared to the 30-fold stimulation of γ by δδ'. Whereas β stimulated the γδδ' ATPase 3-fold, the β subunit did not stimulate the γδδ' ATPase at all, in fact β sightly inhibited it, yet the τδδ' complex is as active as γδδ' in reconstituting a processive polymerase with β and αε.

The cloned δ' preparation appears as a doublet in a 13% SDS polyacrylamide gel and the two polypeptides are of the same size and molar ratio (2:1, lower band-to-upper band) as the δ' doublet purified from the γ complex. Electrospray mass spectometry revealed that the smaller polypeptide (δ'$_S$) was the size predicted from the gene sequence and the larger polypeptide (δ'$_L$) was increased in size by 521 Da. The nature of the larger polypeptide is presently under investigation. Possibilities include mRNA splicing, use of an upstream translational start signal, readthrough of the stop codon, translational frameshifting, and posttranslational modification. Whatever the mechanism which produces δ'$_L$ it must be efficient since the highly overproduced δ' still produces the same level of δ'$_L$ relative to the δ'$_S$ and δ'$_L$ within the holoenzyme. Irrespective of how δ'$_L$ is synthesized, the fact remains that δ'$_L$ and δ'$_S$ are different. Presumably they also have functional differences as in the case of the related γ and τ subunits. Whereas τ and γ both appear to be within each holoenzyme molecule, it remains to be shown whether the δ'$_L$ and δ'$_S$ subunits are on one or on different holoenzyme molecules.

Sequence analysis of δ'$_L$ and δ'$_S$ show they have identical N-termini proving δ'$_L$ is not derived from an alternate upstream ATG start site. Translational readthrough of the stop codon was considered as an explanation which would produce a protein containing 19 additional amino acids before the next stop codon in the open reading frame, but this would increase the site of δ' by 2130 Da, much larger than the observed mass of δ'$_L$. Treatment of δ' with calf intestinal and bacterial alkaline phosphatases did not effect the mobility of either δ'$_S$ or δ'$_L$ suggesting that serine and threonine phosphorylation is not involved in the formation of δ'$_L$; attachment of other groups remains a possibility. Hence, translational frameshifting (or jumping), covalent modification (other than phosphate on Ser or Thr) and mRNA splicing remain possible.

It seems most pertinent to consider translational frameshifting as a source of δ'$_L$ since such a mechanism has precedent in holoenzyme structure. The dnaX gene encoding the τ subunit of the holoenzyme generates the γ subunit by a translational frameshift into the −1 reading frame. If δ'$_L$ is produced by a −1 frameshift, the frameshift would have to occur upstream of the holB stop codon but not so far upstream that a −1 frameshift would produce a truncated protein due to running into an early −1 frame stop codon. Thus the −1 frameshift would have to occur at or after the last −1 frame stop codon near Glu$_{320}$ after which translation would proceed past the normal stop codon in the open reading frame to produce a protein which is 7 amino acids larger than that predicted by the open reading frame of holB.

The γ complex expends ATP energy to clamp the β subunit onto a primer and it is this β dimer clamp that tethers the αε polymerase to the template for rapid and highly processive DNA synthesis by the αε polymerase which is only efficient after the β subunit has been clamped onto the DNA by γ complex action. A mixture of the γ and δ subunits is sufficient in this assay to clamp β onto DNA, however much more γ and δ is needed relative to the amount of γ complex. The δ' subunit stimulates γ and δ in this assay such that the amounts of γ, δ and δ' are nearly comparable with the amount of γ complex that is required (the λ and ψ subunits give another 3–8 fold stimulation of activity at low concentrations of γδδ', as described in the accompanying report. Likewise, neither δ or δ' have a large effect on the ATPase activity of γ but addition of both δ and δ' to γ gives a 30-fold stimulation of the γATPase activity. The requirement of both δ and δ' for efficient replication activity and for maximal ATPase activity of γ correlates with the physical studies in the accompanying report which show that δ and δ' form a complex and the δδ' complex binds tightly to γ, whereas when δ and δ' are added separately with γ they do not form a strong γδ or γδ' complex.

The τ subunit contains the sequence of the γ subunit (γ is produced from τ) plus, an extra domain of 212 amino acids which binds to α and to DNA.

A homology search of the translated GenBank indicated that the most homologous protein to δ' of the present invention was another *E. coli* protein, the γ/τ subunit(s) of DNA polymerase III holoenzyme. There is 27% identity and 44% similarity including conservative substitutions over the entire length of δ' and γ/τ. One particular region in δ' of 50 amino acids (amino acids 110–159) is strikingly similar to γ/τ (amino acids 121–170) having 49% identity. A putative helix-turn-helix motif in γ/τ ($Ala_{114}X_3Gly_{118}X_5Leu_{124}$) is positioned just 19 residues downstream of the helix-turn-helix motif in δ'.

The extent of sequence homology between δ' and the γ/τ subunitr is above the level required to speculate that they have similar three dimensional structures; when both $δ'_S$ and $δ'_L$ are taken into account, four of the eleven subunits within the holoenzyme, according to the present invention, may have similar structures.

The interactions between δ and δ' were also studied as part of the present invention.

Equal amounts of δ and δ' were incubated together for 30 minutes at 15° C. and then analyzed by gel filtration and glycerol gradient sedimentation. Gel filtration analysis showed δ and δ' subunits comigrate and elute approximately six-to-eight fractions earlier than either δ or δ' alone indicating that they form a δδ' complex. Comparison with protein standards yields a Stokes radius of 31.1 Å. The δ and δ' also comigrated during glycerol gradient analysis and sedimented faster than either δ or δ' alone, again consistent with formation of a δδ' complex with an S value of 3.9S. Combining the S value and Stokes radius yields a native mass of 53 kDa for the δδ' complex, most consistent with the mass of a 1:1 complex of $δ_1δ'_1$ (75.6 kDa) then of a higher order aggregate of δδ'. Both $δ'_L$ and $δ'_S$ are visible in the δδ' complex indicating they are present as a mixture of $δδ'_L$ and $δ'_S$. Formation of a trimeric $δδ'_Lδ'_S$ complex is unlikely as the combined mass would be 113 kDa, twice the observed mass. However, if free δ and δ' were in a rapid equilibrium with the δδ' complex then the observed mass of the δδ' complex would be a weighted average of the amount of complex and amount of free subunits and therefore the possibility of a higher order aggregate such as a $δδ'_Lδ'_S$ complex can not be rigorously excluded.

Densitometry analysis of the Coomassie Blue stained gel yielded a molar ratio of δ:δ' of 1.1:1.0, respectively (the two δ' bands were considered together as one δ') further supporting the $δ_1δ'_1$ composition. Different proteins may take up different amounts of Coomassie Blue stain and therefore molar rates determined by densitometry must be regarded as tentative. A dynamic light scattering analysis of δ, δ' and δδ' complex is also presented in the table below.

The Stokes radius and sedimentation coefficient of δ, δ' and δδ' complex were determined from the gel filtration and glycerol gradient sedimentation analyses; and the native molecular mass and the frictional coefficient were calculated from the Stokes radius and S value. These calculations require the partial specific volume of δ and δ'; these volumes were calculated by summation of the partial specific volumes of the individual amino acids for each δ and δ'. Molecular weights of δ, δ' and the δδ' complex (assuming a composition of $δ_1δ'_1$) were calculated from the gene sequences of δ and δ'.

|  | δ | δ' | δδ' |
|---|---|---|---|
| Stokes radius | 26.5 | 25.8 | 31.1 |
| Sedimentation coefficient | 3.0 | 3.0 | 3.9 |
| Partial specific volume | 0.74 | 0.74 | 0.71 |
| Native mass (radius and S value) | 34,708 | 33,791 | 52,952 |
| Native mass (gene sequence) | 38,704 | 36,934 | 75,630 |
| Frictional coefficient | 1.22 | 1.20 | 1.25 |
| Diffusion coefficient (light scattering) | 7.60 | 8.16 | 6.61 |
| Radius calculated (D) | 28.2 | 26.3 | 32.5 |

The diffusion coefficient obtained from the light scattering analysis can be used to calculate the Stokes radius and these values were within 6% of the Stokes radius of δ, δ' and δδ' complex determined in gel filtration.

In the γ complex, the γ, δ and δ' subunits are bound together along with the χ and ψ subunits. The activity analysis described herein indicates that γ and δ interact since both are necessary and sufficient to assemble the β clamp onto DNA. Further, the δ' subunit stimulates the DNA dependent ATPase activity of γ indicating that γ and δ' interact.

The physical interaction between δ, δ' and γ were examined using the gel filtration technique which detects tightly bound protein-protein complexex, but since components are not at equilibrium during gel filtration, weak protein complexes will dissociate. The γ subunit (47 kda) is larger than δ and δ', and is at least a dimer in its native state with a large Stokes radius and quite an asymmetric shape (γ runs as a trimer or tetramer in gel filtration and as a dimer in a glycerol gradient. The γ was mixed with a 4-fold molar excess of δ and δ' then gel filtered. A complex of γδδ' was formed as indicated by the comigration of both the δ and δ' subunits with γ. The excess δδ' complex eluted much later (fraction 40–46). Since δ binds δ', it is possible that only one, for example δ, binds γ and the other (eg. δ') is part of the complex by virtue of binding δ instead of directly interacting with γ. To determine which subunit, δ or δ', binds directly to γ, the γ subunit was mixed with either δ or δ' then gel filtered. The mixture of γ and δ showed that γ and δ did not form a gel filterable γδ complex as indicated by the absence of δ in fractions 24–32 containing γ. The mixture of γ and δ' showed that δ' did not form a complex with γ either as indicated by the absence of δ' in fractions containing γ. Therefore both δ and δ' must be present to form a gel filterable complex with γ. Using pure cloned δ no γδ complex in gel filtration (or in glycerol gradient analysis) was seen.

The gel filtration column fractions of the γδδ' complex were analyzed for their activity in assembly of the β clamp on primed DNA. Fractions containing the γδδ' complex were quite active. The δδ' complex, even at high concentration, is not active in assembly of the β clamp and therefore the slight amount of activity in following fractions wag probably due to a slight amount of γ which trailed into the peak of the δδ' complex thus giving activity in the assay. The column fractions of the γδ and γδ' mixtures were inactive except for the peak fraction of γ in the γδ' analysis which supported weak activity. There was a slight, barely detectable amount of δ' (but not δ), in the fractions containing γ as though a slight amount of γδ' complex was formed and survived the column.

Following these studies with δ and δ', the present invention has found that δ behaved as a monomer in gel filtration and glycerol gradient sedimentation. The δ' subunit also appeared monomeric. Neither δ or δ', when separate, formed a gel filterable complex with the γ subunit. Yet they most likely bind to γ (at least weakly) as indicated by activity assays in which γδ is active (without δ') in assembly of the β clamp, and δ' (without δ) stimulates the DNA dependent ATPase activity of γ. The δ and δ' subunits bound each other to form a gel filterable 1:1 $δ_1δ'_1$ complex and when mixed with γ they efficiently formed a tight gel filterable γδδ' complex. Hence, the binding of δ and δ' to γ is cooperative.

The δ' subunit is a mixture of two related proteins, $δ'_L$ and $δ'_S$ which are encoded by the same gene; $δ'_L$ is 521 da larger than the gene sequence predicts. The functional and structural difference between them is presently unknown. In these binding studies, both $δ'_S$ and $δ'_L$ bound to δ and they both assembled into the γδδ' and τδδ' complexes, consistent with the fact that both $δ'_L$ and $δ'_S$ are observed within polIII and the γ complex.

No single subunit of the γ complex is active in assembling the β clamp on DNA. Presumably this reaction is to complicated for just one protein. A mixture of γ and δ is capable of assembling β onto DNA although they are inefficient and require δ' for efficient activity. Perhaps δ' increases the efficiency of γδ by physically bringing γ and δ together in the γδδ' complex, although it is also possible that δ' participates directly in the chemistry of the reaction. The γ subunit has a low level of DNA dependent ATPase activity, and described above, δ binds the β subunit. These two facts allow speculation that γ binds the primed template and δ brings in the β subunit, then ATP hydrolysis is coupled to assemble the ring shaped β dimer around the DNA.

Since γ is known to bind ATP and has a low level of DNA dependent ATPase activity, it is an obvious candidate as the subunit which interacts with the ATP in the β clamp assembly reaction. Two molecules of ATP are hydrolyzed in the initiation reaction in which the holoenzyme becomes clamped onto a primed template to form the initiation complex. This initiation reaction has its basis in the assembly of the β clamp on DNA. The stoichiometry of two ATP hydrolyzed in formation of one initiation complex suggests two proteins hydrolyze ATP. These two proteins may be the two halves of a γ dither. However it is also possible that δ interacts with ATP. The sequence of δ shows a very close match to the consensus for an ATP binding site and UV induced cross-linking studies suggest that δ binds ATP. The availability of δ in quantity should now make possible a full description of the mechanism by which ATP is coupled to assemble the ring shaped β dimer around DNA.

The third subunit according to the present invention, that of θ, was also identified, purified, cloned and sequenced. N-terminal analysis of the θ peptide yielded the following sequence of 40 amino acids:

```
Met Leu Lys Asn Leu Ala Lys Leu Asp Gln Thr Glu Met Asp Lys
              5                    10                    15

Val Asn Val Asp Leu Ala Ala Ala Gly Val Ala Phe Lys Glu Arg
             20                    25                    30

Tyr Asn Met Pro Val Ile Ala Glu Ala Val
             35                    40
```

Based upon this sequence, two DNA probes were fashioned. These probes had the sequences of:

```
ATG CTG AAA AAC CTG GCT AAA CTG GAT CAG ACT GAA ATG GAT AAA    45

GTT AAC GTT GAT                                                57; and

CTG GCT GCT GCT GGT GTT GCT TTT AAG GAA CGT TAT AAC ATG CCG    45

GTT ATT GCT GAA                                                57.
```

These two probes were also end-labelled with $^{32}P$ for use with Southern blot procedures.

For Southern blot analysis, E. coli DNA was cut with the 8 Kohara map enzymes [see Cell 50:495 (1987)]. The two probes described above were used to probe two Southern blots of E. coli DNA. The bands (DNA fragments) in common with the two blots were noted, as was their size. At least 3 positions on the Kohara map of the E. coli chromosome were consistent with the Southern blot fragmentation pattern.

Thus, based upon these findings, E. coli Dna digested with either EcoRV or PvuII following DNA extraction [see J.M.B. 3:208 (1961)] was run out in an agarose gel, and all the DNA in the size region of the gel corresponding to the fragment size containing θ for that enzyme (PvuII or EcoRV) from the Southern blot analysis, was extracted from the gel and cloned into M13mp18 and M3mp19 using conventional techniques. The M13 transformant DNAs were analyzed by Southern blot and probed using the two probes described above. One M13 DNA was obtained with the θ sequence. When this M13 θ was sequenced, however, not all the theta gene was present; the gene extended beyond the PvuII restriction sits. The M13 θ was then used as a reagent to obtain the complete θ gene.

A Kohara λ phage (λ₃₃₆) was grown and the θ gene in *E. coli* was excised using an EcoRV cut 2.7 kb fragment. Next, a filter containing all the Kohara λ phage was probed using the partial θ gene as the probe. Thus, it was possible to identify the λ phage containing the full θ gene.

The holE gene was then cloned from the λ phage into pUC18 and subsequently sequenced. The full genetic sequence for the θ gene was thus determined to be:

```
ATG CTG AAG AAT CTG GCT AAA CTG GAT CAA ACA GAA ATG    39

GAT AAA GTG AAT GTC GAT TTG GCG GCG GCC GGG GTG GCA    78

TTT AAA GAA CGC TAC AAT ATG CCG GTG ATC GCT GAA GCG    117

GTT GAA CGT GAA CAG CCT GAA CAT TTG CGC AGC TGG TTT    156

CGC GAG CGG CTT ATT GCC CAC CGT TTG GCT TCG GTC AAT    195

CTG TCA CGT TTA CCT TAC GAG CCC AAA CTT AAA            228
```

The open reading frame above predicts that θ is a 76 amino acid protein of 8,629 Da. The underlined nucleotide sequence exactly matches the corresponding N-terminal sequence of θ. In addition, the upstream sequence contains two putative RNA polymerase promoter signals and a Shine-Dalgarno sequence. This upstream sequence is:

Using site-directed mutagenesis, the initial Met codon (AGA ATG) was mutated to CAT ATG (NdeI site) using an oligonucleotide with 15 bases on either side of the mutation. This was then used to obtain the overproduction of the θ gene in which the mp19θ (a 2700 bp insert) was grown in strain CJ236 cells in the presence of uridine. The purified single stranded DNA from these cells was purified and hybridized with the NdeI mutation and replicated with the holoenzyme in vitro. XLI-Blue cells were transformed with the double stranded DNA product and ten plaques were selected for miniprep sequencing; all 10 plaques contained the mutation. The θ sequence was excised from the DNA with HindIII, NdeI, and the resulting 1 kbp fragment was inserted into pET-3C [see Methods in Enzymology 185:60 (1990)]. The resulting pET-3Cθ was used to transform competent cells [BL21(DE3)]. Single colonies of the trans-

```
AG GCGTAGCGAA GGGAGCGTGC AGTTGAAGCC ATATTATCTA TTCCTTTTTG    52

TAATAACTTT TTTACAGACG ATAACCTTGT CTAATGTCTG AGTCGAGGAT        102

CATCAATTCC GGCTTGCCAT CCTGGCTCAC TCTTAGTAAC TTTTGCCCGC        152

GAATGATGAG GAGATTAAGA                                         172
```

The downstream sequence begin with a stop codon:

```
TAA AACTTATAC AGAGTTACAC TTTCTTACAT AACGCCTGCT AAATTATGAG     52

TATTTTCTAA ACCGCACTCA TAATTTGCAG TCATTTTGAA AAGGAAGTCA        102

TTATG                                                          107
```

This translated into the peptide sequence:

```
Met Leu Lys Asn Leu Ala Lys Leu Asp Gln Thr Glu Met Asp Lys
                 5                  10                      15

Val Asn Val Asp Leu Ala Ala Ala Gly Val Ala Phe Lys Glu Arg
                20                  25                      30

Tyr Asn Met Pro Val Ile Ala Glu Ala Val Glu Arg Glu Pro
                35                  40                      45

Glu His Leu Arg Ser Trp Phe Arg Glu Arg Leu Ile Ala His Arg
                50                  55                      60

Leu Ala Ser Val Asn Leu Ser Arg Leu Pro Tyr Glu Pro Lys Leu
                65                  70                      75

Lys
76
``` formed cells were grown in liquid media at 37° C. to an OD of about 0.6, induced with IPTG generally as described previously and harvested post induction. Successful overexpression of the θ peptide was obtained using this system.

The N-terminal sequence analysis of θ was examined as follows: PolIII was purified [see J. Biol. Chem. 263:6570 (1988)] except that the last step using Seperose 6 was replaced with an ATP-agarose column (Pharmacia, type II) which was eluted with a linear salt gradient. After the δδ' eluted from the ATP agarose column, a mixture of pure polIII' and γχψ complex eluted together. This mixture was separated by column chromatography on MonoQ using a linear gradient of 0–0.4 M NaCl in buffer A. The polIII' which was eluted after the γχψ complex was used as the source of θ subunit. The subunit was separated from α, τ and ε subunits of polIII' by electrophoresis in a 15% SDS polyacrylamide gel, and was electroblotted (110 pmol) onto PVDF membrane. The θ subunit was visualized by Ponceau S stain, and the N-terminal sequence was determined to be:

```
NH2-Met Leu Lys Asn Leu Ala Lys Leu Asp Gln Thr Glu Met Asp Lys
              5                   10                  15

Val Asn Val Asp Leu Ala Ala Ala Gly Val Ala Phe Lys Glu Ala Tyr
              20                  25                  30

Asn Met Pro Val Ile Ala Glu (Ala) (Val)
              35
``` in which the parenthesis indicate uncertain amino acid assignments.

The θ was isolated using *E. coli* genomic DNA isolated from strain C600 [see J. Mol. Biol. 3:208 (1961)], cut with the Kohara panel of restriction enzymes (BamHI, HindIII, EcoRI, EcoRV, BglI, KpnI, PstI and PvuII), and separated in a 0.8% native agarose gel. The gel was depurinated (0.25 M HCl), denatured (0.5 M NaOH, 1.5 M NaCl) and neutralized (1 M Tris, 2 M NaCl, pH 5.0) prior to transfer of the DNA to Genescreen plus (DuPont New England Nuclear) using a Vacugene (Pharmacia) apparatus in the presence of 2×SSC (0.3 M NaCl, 0.3 M sodium citrate, pH 7.0). The membrane was air dried prior to hybridization. Two synthetic oligonucleotide DNA 57-mer probes were designed based on the N-terminal sequence of θ assuming the highest frequency of codon usage and favoring T over C in the wobble position. The two probes (5'→3') were:

```
Theta 1 (codons 1-19):
ATG CTG AAA AAC CTG GCT AAA CTG GAT CAG ACT GAA ATG GAT    42

AAA GTT AAC GTT GAT                                        57; and

Theta 2 (codons 20-38):
CTG GCT GCT GCT GGT GTT GCT TTT AAA GAA CGT TAT AAC ATG    42

CCG GTT ATT GCT GAA                                        57.
```

The DNA 57-mers (100 pmol each) were 5' end-labelled using 1 μM [γ-$^{32}$P] ATP and T4 polynucleotide kinase, and then used to probe Southern blot of the restricted *E. coli* genomic DNA. Two Southern blots were hybridized individually using one or the other of the 57-mer probes overnight in the same buffer as above except with an additional 200 μg/ml of denatured salmon sperm DNA. The Southerns were washed in 2×SDS at room temperature for 30 minutes, then 3 hours at 42° C. (changing the buffer each hour), then exposed to X-ray film. The Theta 1 probe showed a single band in 7 of the 8 restriction digests; the Theta 2 probe consistently showed many bands in each lane which were eliminated equally as the hybridization and washing conditions were gradually increased in stringency, suggesting that Theta 2 did not match the true sequence of the holE gene. After holE was cloned and sequenced, it was found that 7 nucleotides of Theta 1 and 12 nucleotides of Theta 2 did match the holE sequence.

To clone the holE gene, 100 μg of *E. coli* DNA was digested with PvuII, and the small population of DNA fragments migrating in the 400 to 600 bp range (the Southern blot using Theta 1 probe indicated holE was on a 500 bp PvuII fragment) was extracted from the agarose gel, blunt-end ligated into M13mp18 digested with HincII, and transformed into competent XL1-Blue cells. Presence of the holE gene was determined by Southern blot analysis of minilysate DNA prepared from recombinant colonies using the 5' end-labelled Theta 1 as a probe. One positive clone was obtained and sequenced; it contained approximately one-half of the holE gene (a PvuII site lies in the middle of holE). This fragment of holE was uniformly labelled using the random primer labelling method, and used to screen the complete Kohara ordered lambda phage library of *E. coli* chromosomal DNA transferred onto a nylon membrane. Prehybridization and hybridization were conducted as described above except that the temperature was increased to 65° C. and the wash steps were more stringent (2×SSC, 0.2% SDS, next 1×SSC, and then 0.5×SSC at 65° C.). A single phage clone λ 19H3 (336 of the miniset) [see Cekk 50:495 (1987)] hybridized with both the genomic fragment and the Theta 1 probe.

The phage and a 2.7 kb EcoRV fragment containing the θ gene was excised, purified from a native agarose gel, and blunt-end ligated into the HincIII site of M13mp19 to yield M13mp19-θ. The 2.7 kb EcoR1-HindIII fragment from M13mp19-θ was excised, gel purified, and directionally ligated into the corresponding sites of pUC18 to generate pUC-θ. Both strands of the holE gene in pUC-θ were sequenced using the sequenase kit [α-$^{35}$S]dATP, and synthetic DNA 20-mers. This time the entire holE gene was present.

An NdeI site was generated at the start codon of the holE gene by the oligonucleotide site directed mutagenesis using a DNA 33-mer:

ATGATGAGGA GATTA<u>CATAT</u>G CTGAAGAAT CTG
33 containing an NdeI site (underlined) at the start codon of holE to prime replication of M13mp19-θ viral ssDNA and using SSB and DNA polymerase III holoenzyme in place of DNA polymerase I. The NdeI site in the resultant phage (M13mp19-θ-NdeI) was verified by DNA sequencing. An approximately 1 kb NdeI-HindIII fragment was excised from M13mp19-θ-NdeI and directionally ligated into the corresponding sites of pUC18 to yield pUC-θ-NdeI. A 1 kb NdeI/BamHI fragment from pUC-θ-NdeI was then subcloned directionally into pET3c digested with both NdeI and BamHI to generate the overproducing plasmid, pET-θ.

Reconstitution assays contained 72 ng phage χ 174 ssDNA (0.04 pmol as circles) uniquely primed with a DNA 30-mer, 0.98 SSB (13.6 pmol as tetramer) 10 ng β (0.13 pmol as dimer), and 4 ng γ complex (0.02 pmol) in 20 mM Tris-HCl (pH 7.5), 8 mM $MgCl_2$, 5 mM DTT, 4% glycerol, 40 μg/ml BSA, 0.5 mM ATP, 60 μM dGTP, and 0.1 mM EDTA in a final volume of 25 μl (after addition of αε or αεθ). The αε and αεθ complexes were each preformed upon mixing 38 pmol each of α and ε, and when present, 152 pmol of θ in 12.5 μl of 25 mM Tris-HCl (pH 7.5), 2 mM DTT, 1 mM EDTA, 10% glycerol followed by incubation for 1 hour at 15° C. These protein complexes were diluted 30-fold in the same buffer just prior to addition to the assay on ice, then the assay tube was shifted to 37° C. for 6 minutes to allow reconstitution of the processive polymerase on the primed ssDNA. DNA synthesis was initiated upon rapid addition of 60 μM dATP and 20 μM [α-$^{32}$p]TTP, then quenched after 15 seconds and quantitated using de81 paper. Proteins used in the resconstruction assays were purified, and their concentrations determined using BSA as a standard.

A synthetic DNA 56-mer was designed as a hooked primer template to assay 3'→5' exonuclease activity:

A DNA 56-mer (75 pmol as 56-mer) was 3' end-labelled with 75 pmol of [α-$^{32}$P] dTTP (3000 Ci/mmol) using 200 units of terminal transferase under conditions specified by the manufacturer (Boehrnger) in a total volume of 100 μl followed by spin dialysis to remove remaining free nucleotide.

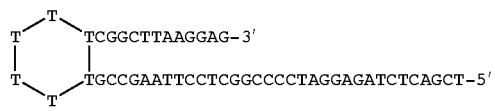

Prior to adding proteins to the assay, θ was titrated into ε upon incubating 2 μg ε (70 pmol as monomer) with θ (0–10 μg, 0–1.16 nmol as monomer) in a total volume of 10 μl buffer A containing 50 μg/ml BSA at 15° C. for 1 hour. The εθ mixture was then diluted 100-fold using buffer A containing 50 μg/ml BSA. A 2.5 μl sample of diluted complex was added to 200 nmol 3'-$^{32}$P-end-labelled mispaired hook DNA in 12.5 μl of 25 mM Tris-HCl (pH 7.5), 4% sucrose, 5 mM $MgCl_2$, 8 mM DTT, and 50 μg/ml BSA followed by a 3 minute incubation at 15° C. The reaction was quenched upon spotting 13 μl of the mixture onto a DE81 filter. The amount of mispaired nucleotide remaining was quantitated, and subtracted from the total mispaired template added to obtain the amount of 3' mispaired nucleotide released.

Gel filtration was performed using HR 10/30 fast protein liquid chromatography columns, Superdex 75 and Superose 12, in buffer C. Samples containing either θ, ε or α alone, and mixtures of these subunits were incubated at 15° C. for 1 hour. The entire sample was then injected onto the column and after collection the first 5.6 ml (Superose 75) or 6.0 ml (superose 12), fractions of 160 Ml were collected and analyzed in 15% SDS polyacrylamide gels. Protein standards were a mixture of proteins of known Stokes radius and were also analyzed. Densitometry of stained gels was performed using a laser densitometer, Ultrascan XL (Pharmacia-LKB).

Subunits (α, θ, ε) alone and mixtures of these subunits were incubated 1 hour at 15° C. (with 5% glycerol), then mixed with protein standards of known S value (50 μg of each protein standard) and immediately layered onto 12.3 ml linear 10%–30% glycerol gradients in 25 mM Tris-HCl (pH 7.5), 0.1 M NaCl, 1 mM EDTA. The gradients were centrifuged at 270,000×g for 44 hours (ε, θ, and εθ complex) or 26 hours (αε and αεθ) at 4° C. Fractions of 150 μl were collected from the bottom of the tube and, analyzed in a 15% SDS-polyacrylamide gel stained with Coomassie Blue.

In summary, the sequence of the N-terminal 40 amino acids of θ were obtained from the θ subunit within the polIII' subassembly (αεθτ) of holoenzyme. This sequence did not match any previously identified in GenBank, and therefore the invention attempted to identify the holE gene using the Kohara restriction map of the E. coli chromosome. Two 57-mer DNA probes were made based on the N-terminal amino acid sequence of θ and were used in a Southern analysis of E. coli genomic DNA digested with the eight Kohara restriction map enzymes. One of the 57-mer probes hybridized to a single band in 7 of 8 bands obtained upon Southern analysis, indicating that these 7 fragments must overlap in the holE gene. The Kohara restriction map was searched, and four near matches were located. Since which of these positions could not be distinguished in the Kohara map as the true holE gene, the small 500 bp PvuII fragment from genomic DNA was directly cloned into M13mp18. The DNA sequence of this PvuII fragment predicted an amino acid sequence which matched exactly to the 40 residue N-terminal sequence of θ. However, this was only a partial clone of holE due to an internal PvuII site. The PvuII fragment and one of the synthetic 57-mers were subsequently used to probe the entire Kohara library of overlapping λ phage on one membrane which identified the location of holE within λ 19H3 (No. 336 of the miniset).

The Kohara restriction map of the chromosome in the vicinity of λ 19H3 shows a close match to the fragment sizes obtained from the Southern analysis. The overlapping fragments identify the position of holE at 40.4 minutes on the E. coli chromosome. DNA analysis showed two BglI sites separated by 122 bp that span the Theta 1 57-mer probe, thus explaining the absence of a BglI fragment in the Southern analysis in which a small fragment would have run off the end of the gel. This small fragment would also have been missed in the procedure used by Kohara, accounting for the single BglI site shown on the map.

A 2.7 kb EcoRV fragment was subcloned from λ 19H3 into M13mp18 and the holE gene was sequenced. The DNA predicts θ is a 76 amino acid protein of 8,647 Da, slightly smaller than the 10 kDa estimated from the mobility of θ in a SDS-polyacrylamide gel. The pI of θ based on the amino acid composition is 9.79, suggesting it is basic, consistent with its ability to bind to phosphocellulose, but not to Q Sepharose. The molar extinction coefficient of θ at 280 nm calculated from its single Trp and the two Tyr residues is 8,250 $M^{-1}cm^{-1}$.

Site directed mutagenesis was performed on the holE gene cloned into M13mp18 to create an NdeI site at the initiator methionine. The holE gene was excised from the site mutated M13mp18, inserted into pUC18 (in order to use a convenient BamHI site), then a 1 kb NdeI-BamHI fragment containing holE was ligated directionally into the NdeI and BamHI sites of pET3c to yield the pET-θ overproducing plasmid in which holE expression is driven by T7 RNA polymerase. The pET-θ was introduced into BL21(DE3) cells and upon induction of T7 RNA polymerase by IPTG, θ was expressed to 63% of total cell protein. The induced subunit was freely soluble upon cell lysis and its purification was relatively straight-forward. Four liters of cells were lysed and 300 mg of pure θ was obtained in 78% overall yield after column chromatography on Q sepharose, hoparin agarose, and phosphocellulose.

Specifically, the purification of θ was carried out by utilizing four liters of BL21(DE3) cells harboring the pET-θ expression plasmid were grown in 4 L of LB Media containing 50 μl.ml carbenicillin. Upon growth to an $OD_{600}$ of 0.6, IPTG was added to 0.4 mM and the cells were incubated at 37° C. for 2 hours further before they were harvested by centrifugation (8.4 g wet weight) at 4° C., resuspended in 15 ml of cold 50 mM Tris-HCl (pH 7.5) and 10% sucrose, and stored at −70° C. The cells were thawed and lysed by heat lysis. The cell lysate (Fraction I, 20 ml, 880 mg) was dialyzed (all procedures were performed at 4° C.) for 2 hours against 2 L of buffer A, and then diluted 2-fold with buffer A to a conductivity equal to 50 mM NaCl. The lysate was then applied to a 55 ml Q sepharose fast flow column equilibrated in buffer A. The θ flowed through the column as analyzed by a Coomassie Blue stained 15% SDS polyacrylamide gel and confirmed by the stimulation of the ε exonuclease activity assay developed for θ. The Q sepharose flow through fraction (Fraction II, 81 ml, 543 mg) was then applied to a 50 ml column of heparin agarose (BioRad) which was equilibrated in buffer A containing 50 mM NaCl. The flow through fraction containing θ was approximately 95% pure θ (Fraction III, 110, 464 mg), and was dialyzed overnight against 2 L buffer B, then applied to a 40 ml phosphocellulose column (P11, Whatman) equilibrated in buffer B. The column was washed with buffer B and θ was eluted using a 400 ml linear gradient of 10 mM to 200 mM sodium phosphate (pH 6.5) in buffer B. Eighty fractions were collected and analyzed for θ. Fractions 42–56 were pooled (Fraction IV, 68 ml, 300 mg) and dialyzed against 2 L buffer A prior to aliquoting and storage at −70° C. The protein concentration was determined using BSA as a standard. Concentration of pure θ determined by absorbance at 280 nm using E280 at 8,250 $M^{-1}cm^{-1}$ was 90% of the protein concentration.

| Step | | total protein (mg) | total units[1] | specific activity (units/mg) | fold purification | % yield |
|---|---|---|---|---|---|---|
| I | Cell Lysate | 880 | $2.7 \times 10^6$ | $3.1 \times 10^3$ | 1.0 | 100 |
| II | Q Sepharose | 543 | $2.3 \times 10^6$ | $4.2 \times 10^3$ | 1.4 | 85 |
| III | Heparin Agarose | 464 | $2.6 \times 10^6$ | $5.6 \times 10^3$ | 1.8 | 96 |
| IV | Phospho-Cellulose | 300 | $2.1 \times 10^6$ | $7.0 \times 10^3$ | 2.3 | 78 |

[1]One unit is defined as the increase in fmol nucleotide released per minute relative to the same reaction with no θ added (ε alone).

Throughout this description of the present invention, buffer A was 20 mM Tris-HCl (pH 7.5), 10% glycerol, 0.5 mM EDTA, and 2 mM DTT; Buffer B was 10 mM $NaPO_4$ (pH 6.5), 10% glycerol, 0.5 mM EDTA, and 2 mM DTT; and Buffer C was 25 mM Tris-HCl (pH 7.5), 10% glycerol, 1 mM EDTA and 100 mM NaCl.

Studies of the purified cloned θ showed it had the same amino terminal sequence as predicted by holE (and θ within polIII' used for electroblotting), proving that the it was indeed the purified protein encoded by the cloned gene. The activity of θ (stimulation of ε) co-purified with θ throughout the preparation.

In searching for activity, the subunit was tested for polymerase activity and for endonuclease, 3'→3' exonuclease and 5'→3' exonuclease activities on ssDNA and dsDNA. However, no such activities were observed.

Since θ is one of the subunits of polIII core, it was examined for any effect it might exert on the DNA polymerase and 3'→5' exonuclease activities of α and ε. Previous work compared the ability of αε and polIII core to form the rapid and processive polymerase with holoenzyme accessory proteins, but there was no significant difference between αε and the polIII core (αεθ) suggesting θ had no role in the speed and processivity of synthesis. With pure θ, assays could be performed by either adding θ to αε or omitting θ. In a comparison of the efficiency of αε complex and αεθ complex in their ability to reconstitute the rapid processive polymerase with accessory proteins, the αε (or αεθ) was mixed with the γ complex and β subunit in the presence of ATP and phage X174 ssDNA primed with a synthetic oligonucleotide and "coated" with SSB. The mixture was preincubated for 6 minutes at 37° C. to allow the γ complex time to transfer the β ring to DNA forming the preinitiation complex clamp and time for the polymerase to associate with the preinitiation complex. The rapid processive polymerase can fully replicate this template (5.4 kb) within 12 seconds. Replication was then initiated by the addition of dATP and [α-$^{32}$P]TTP, which were omitted from the preincubation, and the reaction was terminated after 15 seconds. In this assay, the effect of θ on the amount of DNA synthesis will be a reflection of either the speed or processivity of the polymerase or the binding efficiency of the polymerase to the preinitiation complex. Based on a previous comparison of αε and core, θ was not expected to influence the speed or processivity of DNA synthesis. However, in the prior study, the relative affinity of αε and polIII core for the preinitiation complex was not examined.

The αε and αεθ were titrated into this reconstitution assay and the results indicate that θ had little influence in the assay. Therefore, θ does not significantly increase the affinity of αε for the preinitiation complex. These results are also consistent with prior conclusions. The accessory protein preinitiation complex greatly stimulates the activity of the α subunit (without ε) in the reconstitution assay. However, this "α holoenzyme" was half as fast as the "αε holoenzyme" and is only processive for 1–3 kb. The ability of θ to stimulate this "α holoenzyme" was tested in the absence of ε, but the θ subunit had no effect indicating that it did not increase the speed or processivity of the "α holoenzyme" either.

θ was next examined for an effect on the 3'→5' exonuclease activity of ε using a synthetic "hooked" primer template with a 3' terminal G-T mispair. A slight (3-fold), but reproducible stimulation of θ on excision of the 3' mismatched T residue by ε was observed. In the absence of ε, addition of up to 1.0 μg of θ released no 3' terminal nucleotide. These results are compatible with an earlier study comparing 3' excision rates of polIII core and αε complex in which the polIII core was approximately 3-fold faster than αε. Although a 3-fold effect is not dramatic and may not be the true intracellular role of θ, it is large enough to follow θ through the purification procedure. The stimulation of ε exonuclease activity co-purified with θ throughout the purification procedure and the overall activity was recovered in high yield.

The polIII core subassembly of the holoenzyme consists of three subunits: θ, α (polymerase), and ε (3'→5"

exonuclease). Gel filtration wads used to analyze the ability of these individual subunits according to the present invention to assemble into the polIII core assembly. α and θ were mixed together and gel filtered; however, θ did not comigrate with α. Upon mixing ε and θ, a stable εθ complex was formed. The results of these studies are quite consistent with the activity analysis presented above in which θ had no effect on the polymerase but a noticeable effect on the activity of ε.

It has been reported that a concentrated preparation of polIII core (18 μM) was dimeric containing two molecules of polIII core which were presumed to be dimerized through interaction between their θ subunits since a concentrated solution of αε complex contained only one α and one ε. However, in the gel filtration experiments of the present invention, the reconstituted polIII core migrates only slightly larger than the α subunit indicating that θ did not act as an agent of polIII core dimerization.

In gel filtration experiments performed at a concentration of 73 μM α and 73 μM ε in either the absence of θ (αε only), the presence of a substoichiometric amount of θ (molar ratio α:ε:θ of 1:1:0.5), or with excess θ (molar ratio 1:1:3), showed that the presence of θ did not increase the aggregation state (i.e., monomer to dimer). Thus, it may be considered that the αε complex by itself is a dimer. However, comparison of αε and polIII core with size standards in the gel filtration analysis show that they elute near the 158 kDa IgG standard indicating that they are monomeric, i.e., one of each in the complex. They have a Stokes radius of 49 Å which is substantially the radius determined for the αε complex (50 Å), and similar to the 54 Å Stokes radius determined in studies of the dilute monomeric polIII core.

To increase confidence in the aggregation state of these reconstituted complexes, the study of the αε complex and reconstituted polIII core was extended to an analysis of their sedimentation behavior in glycerol gradients using the same concentration and ratio of subunits as in the gel studies.

Again the αε and αεθ essentially co-sedimented regardless of whether θ was present. The αε complex and polIII core each sedimented with an S value close to that of the 150 kDa IgG size standard further indicating they are monomeric subassemblies.

The native molecular weights of θ, ε and of the ετ complex were also determined using gel filtration and glycerol gradient sedimentation. The θ and ε subunits were first analyzed separately: θ, by itself, elutes after myoglobin which is 17.5 kDa, indicating θ is a monomer (8.6 kDa) rather than a dimer of 17.2 kDa; ε migrated just after an ovalbumin standard (43.5 kDa) consistent with ε as a 28.5 monomer rather than a 57 kDa dimer.

To asses the native molecular masses of θ, ε and the εθ complex, the analysis was extended to sedimentation in glycerol gradients. The Stokes radius and S values of θ, ε and εθ complex were determined by comparison to protein standards and their observed mass was calculated. The observed masses of θ, ε and εθ are 11.6 kDa, 32.7 kDa and 35.5 kDa, respectively, values most consistent with θ as a 8.6 kDa monomer, ε as a 28.5 kDa monomer, and the εθ complex having a composition of $\varepsilon_1\theta_1$ (37.1 kDa); densitometric analysis of the εθ complex yielded a molar ration of 1 mol of ε to 0.8 mol θ, consistent with this composition.

The fourth subunit according to the present invention, that of ψ, was also identified, purified, cloned and sequenced. N-terminal analysis of the ψ peptide yielded a protein which, when translated to its genetic sequence was found to be identical to a portion of a much larger sequence described by Yoshikawa [see Mol. Gen. Genet. 209:481 (1987)]. However, Yoshikawa's description was for a rimI sequence from E. coli responsible for encoding an enzyme catalyzing acetylation of the N-terminal portion of ribosomal protein S-18; his upstream sequencing from this gene's reading frame was purely accidental and he does not indicate any appreciation of the gene as a coding sequence for the ψ peptide.

The amino acid sequence obtained from the ψ peptide is:

```
Met Thr Ser Arg Arg Asp Trp Gln Leu Gln Leu Gly Ile Thr
            5               10              15
Gln Trp Ser Leu Arg Arg Pro Gly Ala Leu Gln Gly Glu Ile Ala
            20              25              30
Ile Ala Ile Pro Ala His Val Arg Leu Val Met Val Ala Asn Asp
            35              40              45
Leu Pro Ala Leu Thr Asp Pro Leu Val Ser Asp Val Leu arg Ala
            50              55              60
Leu Thr Val Ser Pro Asp Gln Val Leu Gln Leu Thr Pro Glu Lys
            65              70              75
Ile Ala Met Leu Pro Gln Gly Ser His Cys Asn Ser Trp Arg Leu
            80              85              90
Gly Thr Asp Glu Pro Leu Ser Leu Glu Gly Ala Gln Val Ala Ser
            95              100             105
Pro Ala Leu Thr Asp Leu Arg Ala Asn Pro Thr Ala Arg Ala Ala
            110             115             120
Leu Trp Gln Gln Ile Cys Thr Thr Glu His Asp Phe Phe Pro Gly
            125             130             135
Asn Asp
137
```

Using the information above, the sequence was translated into the genomic structure which is:

```
ATG ACA TCC CGA CGA GAC TGG CAG TTA CAG CAA CTG GGC        39

ATT ACC CAG TGG TCG CTG CGT CGC CCT GGC GCG TTG CAG        78

GGC GAG ATT GCC ATT GCG ATC CCG GCA CAC GTC CGT CTG       117

GTG ATG GTG GCA AAC GAT CTT CCC GCC CTG ACT GAT CCT       156

TTA GTG AGC GAT GTT CTG CGC GCA TTA ACC GTC AGC CCC       195

GAC CAG GTG CTG CAA CTG ACG CCA GAA AAA ATC GCG ATG       234

CTG CCG CAA GGC AGT CAC TGC AAC AGT TGG CGG TTG GGT       273

ACT GAC GAA CCG CTA TCA CTG GAA GGC GCT CAG GTG GCA       312

TCA CCG GCG CTC ACC GAT TTA CGG GCA AAC CCA ACG GCA       351

CGC GCC GCG TTA TGG CAA CAA ATT TGC ACA TAT GAA CAC       390
                                        ‾‾‾‾‾‾‾‾‾‾
GAT TTC TTC CCT GGA AAC GAC                              411
```

In addition to the normal sequence for the genomic material, the gene also contains an internal NdeI site.

The sequence above is preceded by an upstream sequence containing two underlined RNA polymerase promoter signals (TTGGCG and TATATT), and a Shine Dalgarno (AGGAG) sequence. The complete upstream sequence is:

GGCGATTATA GCCATATGTT GGCGCGGTA CGAC-GAATTT GCTATATTTG 50
CGCCCCTGAC AACAGGAGCG ATTCGCT 77.

In addition, the open reading frame is followed by a downstream sequence beginning with a stop codon:

TGA TTTACCGGCA GCTTACCACA TTGAACAACG CGCCCACGCC TTTCCGTGGA 53
GTGAAAAAAC GTTTGCCAGC AACCAGGGCG AGCGTTATCT CAACTTTCAG 103.

The ψ gene was then produced by PCR using *E. coli* genomic DNA and the following (5'→3') primers:
primer 1 (Psi-N):
GATTCCATAT GACATCCCGA CGAGACT 27; and
primer 2 (Psi-C):
GACTGGATCC CTGCAGGCOG GTGAATGAGT 30

As can be seen, primer 1 contains a NdeI site, and primer 2 contains a BamHI site which have been underlined above.

The PCR-produced DNA was used to clone the ψ gene into pET-3c expression plasmid using a two-step cloning procedure necessitated by the internal NdeI site in the nucleic acid sequence. Briefly this procedure involved cutting the PCR product with NdeI restriction enzyme into two portions of 379 (NdeI to NdeI) and 543 (from NdeI to BamHI) bp. The 543 bp portion was ligated into plasmid pET-3c (4638 bp) to form an intermediate pET-3ca (5217 bp). The pET-3ca was then linearized, and the 379 bp portion inserted to form the desired pET-3c plasmid containing the complete PCR product insert.

The overexpression vector containing the complete insert was then inserted into *E. coli* and induced with IPTG as described herein, and overexpression (an increase to over 20% of total bacterial protein) of the ψ protein was seen.

The ψ protein was purified by first dissolving the cell membrane debris in 6 M urea followed by passing the resulting solutions through a hydroxylapetite column, which had been equilibrate previously with a 6 M urea buffer (180 g urea, 12.5 ml 1 M Tris at pH 7.5, 5 ml of 0.5 M EDTA, and 1 ml of 1 M DTT), wherein the ψ peptide will flow through while almost everything else in solution will be held within the column. The The ψ peptide outflow of the hydroxylapetite column was then bound to a DEAE column, rinsed with buffer, and eluted with a gradient of NaCl. Fractions containing the ψ peptide were pooled, dialyzed twice against 1 liter of buffer, and loaded onto a hexylamine column for final purification. Fractions from the hexylamine column containing the ψ peptide were eluted with a NaCl gradient (0.0 to 0.5 M), pooled and saved as pure ψ subunit peptide.

Studies were also conducted to determine that the ψ gene according to the present invention encodes ψ subunit peptide. These studied determined that the N-terminal analysis of native ψ peptide is predicted by the ψ gene sequence according to the present invention; native ψ peptide was obtained and digested with trypsin and a few of the resulting peptides synthesized—the sequenced peptides were encoded by the gene sequence according to the present invention; the cloned/overproduced/pure ψ peptide made in accordance with the present invention comigrated with the ψ subunit peptide within the naturally occurring holoenzyme; and the ψ peptide produced from the sequence according to the present invention formed a γχψ complex when mixed with γ and χ as would occur with natural components.

The γχψ complex was purified [see J. Bio Chem. 265:1179 (1990)] from 1.3 kg of the γ/τ overproducing strain (HB101 (pNT203, pSK100). The ψ subunit was prepared from γ and χ by electrophoresis in a 15% SDS-polyacrylamide gel, then ψ was electroblotted onto PVDF membrane for N-terminal sequencing (220 pmol), and onto nitrocellulose membrane for tryptic digestion (300 pmol) followed by sequence analysis of tryptic peptides. Proteins were visualized by Ponceau S stain. The N-terminal analysis was determined to be: $NH_2$TSRRDDQLQQLGIT. Two internal tryptic peptides were determined to be:

ψ-1:
NH$_2$-Leu Gly Thr Asp Glu Pro Leu Ser Leu Glu Glu Ala Gln Val Ala
                      5                  10                15

Ser Pro; and

ψ-2:
NH$_2$-Ala Ala Leu Trp Gln Gln Ile Cys Thr Thr Glu His Asp Phe Phe
                      5                  10                15

Pro Ala

A 3.2 kb PstI/BamHI (DNA modification enzymes, New Endland Biolabs) fragment containing holD was excised from λ5CI and ligated directionally into the polylinker of Blue Script (Stratagene). The 1.5 kb AccI fragment (one site is in the vector and one is in the insert) containing holD was excised, the ends filled in using Klenow polymerase, then ligated into pUC18 (cut with AccI and the end filled with Klenow) to yield pUC-ψ. Both strands of DNA were sequenced by the chain termination method of Sanger using the sequenase kit [α-$^{32}$P] dATP (radiochemicals, New England Nuclear), and synthetic DNA 17-mer (Oligos etc. Inc.).

A 922 bp fragment was amplified from genomic DNA (strain C600) using Vent DNA polymerase and two synthetic primers, an upstream 32-mer (CAACAGGAGCGATTC<u>CATATGA</u>-CATCCCGACG), and a downstream 30-mer (GATTC<u>GGATCC</u>CTGCAGGCCG-GTGAATGAGT). The first two nucleotides in the NdeI site (underlined) of the upstream 32-mer and the first 11 nucleotides of the downstream 30-mer (including the underlined BamHI sequence) are not complimentary to the genomic DNA. Amplification was performed using a thermocycler in a volume of 100 μl containing 1 ng genomic DNA, 1 μM each primer, and 2.5 units of Vent polymerase in 10 mM Tris-HCl (pH 8.3), 2 mM MgSO$_4$, 200 μM each dATP, dCTP, dGTP and TTP. Twenty five cycles were performed: 1 minute at 94° C., 1 minute at 42° C., 2 minutes at 72° C. Amplified DNA was phenol extracted, ethanol precipitated, then digested with 50 units NdeI in 100 μl 20 mM Tris-acetate, 10 mM magnesium acetate, 1 mM DTT and 50 mM potassium acetate (final pH 7.9), overnight at 37° C. After confirming the NdeI digestion by agarose gel, 50 units of BamHI was added and digestion was continued for 2 hours. The NdeI/NdeI fragment which contained most of the holD gene, and the NdeI/BamHI fragment were separated in an agarose gel, electroeluted, phenol/chloroform extracted, ethanol precipitated and dissolved in 10 mM Tris-HCl (pH 7.5), 1 mM EDTA. The holD gene was cloned into pET3c in two steps. First the NdeI/BamI fragment encoding the C-terminus of ψ was ligated into pET3c digested with NdeI and BamHI to generate pET$_{ψc-ter}$ (linearized with NdeI and dephosphorylated) to yield the pET-ψ overproducer. DNA sequencing of the pET-ψ confirmed the correct orientation of the NdeI/NdeI fragment.

The 25 μl assay contained 72 ng M13mp18 ssDNA (0.03 pmol as circles) primed with a synthetic DNA 30-mer, 0.98 μg SSB (13.6 pmol as tetramer), 82 ng α ε (0.52 pmol), and 33 ng β (0.29 pmol as dimer) in 20 mM Tris-HCl (pH 7.5), 8 mM MgCl$_2$, 40 mM NaCl, 5 mM DTT, 0.1 mM EDTA, 40 μg/ml BSA, 0.5 mM ATP, and 60 μM each dCTP and dGTP. Addition of χ, ψ and γδδ' complex to the assay was as follows. The γδδ' complex, χ and ψ (ψ was initially in 4 M urea) subunits were preincubated before addition to the assay for 30 minutes at 4° C. at concentrations of 2.4 μg/ml γδδ' complex (14.2 nM), 0–0.75 μg/ml χ (45 nM), and 0–0.75 μg/ml ψ (0–48 nM) in 25 mM Tris-HCl (pH 7.5), 2 mM DTT, 0.5 mM EDTA, 50 μg/ml BSA, 20% glycerol (buffer B) (the concentration of urea in the preincubation was 8.5 mM or less). One-half μl of this protein mixture was added to the assay (urea was 0.17 mM or less in the assay after addition of ψ) then the assay was shifted to 37° C. for 5 minutes to allow polymerase assembly before initiating DNA synthesis upon addition of dATP and [α-$^{32}$P] dTTP to 60 μM and 20 μM, respectively. After 20 seconds, DNA synthesis was quenched and quantitated as described in the accompanying report. Assays to quantitate θ in purification were performed likewise except the protein preincubation contained 2.4 μg/ml γδδ' (14.2 nM), 0.75 μg/ml χ (45 nM) and up to 0.25 μg/ml of protein fraction containing θ. After the 30 minute preincubation, 0.5 μl was added to the assay reaction. The SSB, α, ε, β, γ, and τ subunits used in these studies were purified, and the ψ, δ and δ' subunits were prepared from their respective overproducing strains. Concentrations of β, δ, δ', χ and ψ were determined from their absorbance at 280 nm using their molar extinction coefficients: β, 17,900 M$^{-1}$cm$^{-1}$; δ, 46,137 M$^{-1}$cm$^{-1}$; δ', 60,136 M$^{-1}$cm$^{-1}$; χ, 29,160 M$^{-1}$cm$^{-1}$; and ψ, 24,040 M$^{-1}$cm$^{-1}$.

The μl assay contained 140 ng M13mp18 ssDNA in 25 mM Tris-HCl (pH 7.5), and 8 mM MgCl$_2$, 50 μM [γ$^{32}$-P] ATP, 5.45 μmol γ or τ (as dimers), 10.9 pmol χ and/or ψ (as monomers) (unless indicated otherwise) and 1.4 μg SSB (19.4 pmol as tetramer) (when present). Mixtures of proteins (ψ was initially 2 mg/ml (0.13 mM) in 4 M urea) were preincubated 30 minutes on ice at 3.8 μM of each subunit (as monomer) in 30 μl of 25 mM Tris-HCl (pH 7.5), 0.5 mM EDTA, 20% glycerol (0.1 M urea final concentration) before addition to the assay (15 mM urea final concentration). Assays were incubated at 37° C. for 60 minutes 5 minutes for assays containing τ) then quenched upon spotting 0.5 μl on polyethyleneimine thin layer plates (Brinkman Instruments Co.). After chromatography in 0.5 M LiCl, 1 M formic acid, the free phosphate at the solvent front and ATP remaining near the origin were quantitated by liquid scintillation.

Samples of ψ (45 μg, 3 nmol as monomer (initially in 4 M urea)), or a mixture of ψ (45 μg, 3 nmol as monomer) with either γ (65 μg, 0.7 nmol as dimer) or τ (98 μg, 0.7 nmol as dimer) were incubated in 200 μl 25 mM Tris-HCl (pH 7.5), 0.1 M NaCl, 1 mM EDTA, 10% glycerol (0.5 M urea was present after addition of ψ) for 30 minutes at 15° C. The 200 μl sample was injected onto a Pharmacia HR 10/30 gel filtration column of either Superdex 75 or Superose 12 at a flow rate of 0.35 ml/mn in 25 mM Tris-HCl (pH 7.5), 0.1 M NaCl, 1 mM EDTA, 10% glycerol. After the first 5.6 ml, fractions of 170 μl were collected and analyzed in a 15% SDS polyacrylamide gel and the value of Kav was calculated.

A sample of ψ (45 μg, 3 nmol as monomer, initially in 4 M urea) in 200 μl 25 mM Tris-HCl (ph 7.5), 0.1 M NaCl, 1 mM EDTA, 5% glycerol (0.5 M urea final concentration after addition of ψ) was layered onto a 12.3 ml gradient of 10%–30% glycerol in 25 mM Tris-HCl (pH 7.5), 0.1 M NaCl, 1 mM EDTA. Protein standards in 200 μl of the same buffer were loaded in another tube and the gradients were centrifuged at 270,000×g for 44 hours at 4° C. Fractions of 150 μl were collected and analyzed in a 15% SDS polyacrylamide gel stained with Coomassie Blue.

The γδδ' complex was formed upon incubation of 60 μg δ (1.55 nmol as monomer) and 60 μg δ' (1.62 nmol as monomer) with an excess of γ (600 μg, 6.4 nmol as dimer) for 30 minutes at 15° C. in 1 ml of 25 mM Tris-HCl (pH 7.5), 2 mM DTT, 0.5 mM EDTA, 20% glycerol (buffer A). The mixture was chromatographed on a 1 ml HR 5/5 MonoQ column, and eluted with 30 ml linear gradient of 0 M–0.4 M NaCl in buffer A. The γδδ' complex eluted at an unique position, after the elution of free δ', δ and γ (in that order) and was well resolved from the excess γ. The pure γδδ' complex was dialyzed against buffer A to remove salt. Protein concentration was determined using BSA as a standard. Molarity of γδδ' was calculated from protein concentration assuming the 170 kDa mass of a complex with subunit composition $\gamma_2\delta_1\delta'_1$, the composition expected from stoichiometry of subunits in the γ complex.

The γχψ complex was prepared from 1.3 kg of *E. coli* and the ψ subunit was resolved from the γ and χ subunits in a SDS-polyacrylamide gel, then electroblotted onto PVDF membrane for analysis of the amino acid sequence of the amino terminus of ψ. The ψ was also electroblotted onto nitrocellulose followed by tryptic digestion, HPLC purification of peptides and sequence analysis of two tryptic peptides. Search of the GenBank for DNA sequences encoding these peptides identified a sequence which was published in a study of the rimI gene [see Mol Gen Genet 209:481 (1987)]. In order to define the operon structure of this DNA, the DNA upstream of rimI was sequenced. All three peptide sequences of ψ were in one reading frame located immediately upstream of rimI at 99.3 minutes on the *E. coli* chromosome which putatively encodes ψ and referred to as holD.

The promoter for holD underlined in the sequence has been identified previously as the promoter for the rimI gene, encoding the acetylase of ribosomal protein S18, which initiates 29 nucleotides inside of holD. Hence, holD is in an operon of rimI. Production of ψ was inefficient relative to pψd protein as judged by the maxicell technique which detected rimI protein but not ψ. The promoter measured by Northern analysis was strong [see Mol Gen Genet 209:481 (1987)] and the Shine-Dalgarno sequence is a good match to the consensus sequence, as is the spacing from the ATG needed for sufficient translation. Although the cellular abundance of ψ is not known, if one assumes all the ψ sequestered within the holoenzyme, then it is present in very small amounts, there being only 10–20 copies of the holoenzyme in a cell. Perhaps the 3–11 fold more frequent use of some rare codons may contribute to inefficient translation (Leu (UUA), Ser (UCA and AGU), Pro (CCU and CCC), Thr (ACA), Arg (CGA and CGG)).

The open reading frame of holD encodes a 137 amino acid protein of 15,174 Da. Amino terminal analysis of the ψ protein within the γχψ complex showed it was missing the initiating methionine. The molar extinction coefficient of ψ calculated from its 4 Trp and 1 Tyr is 24,040 $M^{-1}cm^{-1}$. There is a potential for a leucine zipper at amino acid residues 25–53, although three prolines fall within the possible leucine zipper. There is also a helix-turn-helix motif ($A/GX_3GX_5I/V$) at $G_{22}G_{26}I_{33}$, but again prolines may preclude helix formation. There is no apparent nucleotide binding site or zinc finger motif.

The polymerase chain reaction was used to amplify holD from genomic DNA. The synthetic DNA oligonucleotides used as primers were designed such that an NdeI site was formed at the initiating ATG of holD and a BamHI site was formed downstream of holD. The amplified hold gene was inserted into the NdeI/BamHI sites of pET3c in two steps to yield pET-ψ in which holD is under control of a strong T7 promoter and is in a favorable context for translation. The sequence of holD in pET-ψ was found to be identical to that depicted in the sequence, and transformation into BL21(DE) plysS cells and subsequent induction of T7 RNA polymerase with IPTG, the ψ protein was expressed to approximately 20% of total cell protein.

The ψ protein was completely insoluble and resisted attempts to obtain even detectable amounts of soluble ψ (lower temperature during induction, shorter induction time, and extraction of the cell lysate with 1 M NaCl were tested); it was necessary to resort to solubilization of the induced cell debris with 6 M urea followed by column chromatography in urea. The ψ was approximately 40% of total protein in the solubilized cell debris and was purified to apparent homogeneity upon flowing it through hydroxyapatite, followed by column chromatography on DEAE sepharose and heparin agarose. By this procedure, 22 mg of pure ψ was obtained from 1 liter of cell culture in 61% yield. The pure ψ remained in solution upon complete removal of the urea by dialysis as described in greater detail below.

Four liters of *E. coli* cells (BL21(DE3)plysS) harboring the pET-ψ plasmid were grown at 37° C. in LB media supplemented with 1% glucose, 10 μg/ml thiamin, 50 μg/ml thymine, 100 μg/ml ampicillin and 30 μg/ml chloramphenicol. Upon reaching an OD of 1.0, IPTG was added to 0.4 mM and after an additional 2 hours of growth at 37° C., the cells were harvested by centrifugation (20 g wet weight), resuspended in 20 ml of 50 mM Tris-HCl (pH 7.5) and 10% sucrose (Tris-sucrose) and frozen at −70° C. The cells lysed upon thawing (due to lysozyme formed by the plysS plasmid), and the following components were added on ice to pack the DNA and precipitate the cell debris: 69 ml Tris-sucrose, 1.2 ml unneutralized 2 M Tris base, 0.2 ml 1 M DTT, and 9 ml of heat lysis buffer (0.3 M spermidine, 1 M NaCl, 50 mM Tris-HCl (pH 7.5), 10% sucrose). After 30 minutes incubation on ice, the suspension was centrifuged in a GSA rotor at 10,000 rpm for 1 hour at 4° C. The cell debris pellet was resuspended in 50 ml buffer B using a dounce homogenizer (B pestle), then sonicated until the viscosity was greatly reduced (approximately 2 minutes total in 15 second intervals) and centrifuged in two tubes at 18,000 rpm in a SS34 rotor for 30 minutes at 4° C. The pellet was resuspended in 50 ml buffer B containing 1 M NaCl using the dounce homogenizer, then pelleted again. This was repeated, and followed again by homogenizing the pellet once again in 50 ml buffer B and pelleted as was done initially. The following procedures were at 4° C. using only one-fourth of the pellet (equivalent to 1 liter of the cell culture). The assay for ψ is described above, and column fractions were analyzed in 15% SDS polyacrylamide gels to directly visualized the ψ protein and aid the exclusion of contaminants during the pooling of column fractions. The pellet was solubilized in 25 ml buffer A containing freshly deionized 6 M urea. The solubilized pellet fraction (fraction I, 85 mg, 22 ml) was passed over a 10 ml column of hydroxyapatite and equilibrated in buffer A plus 6 M urea. The ψ quantitatively flowed through the hydroxyapatite column giving substantial purification. The protein which flowed through the hydroxyapatite column was immediately loaded onto a 10 ml column of DEAE sephacel, equilibrated in buffer A containing 6 M freshly deionized urea, and eluted with a 100 ml gradient of 0–0.5 M NaCl in buffer A containing 6 M freshly deionized urea over a period of 4 hours. Fractions of 1.25 ml were collected and analyzed for ψ as described. Fractions were pooled and dialyzed overnight against 2 liters of buffer A containing 3 M freshly deionized urea and then loaded onto a 10 ml column of hexylamine sepharose. The hexylamine column was eluted with a 200 ml gradient of 0 M–0.5 M NaCl in buffer B containing 3 M freshly deionized urea over a period of 4 hours. Eighty fractions were collected (2.5 ml each), and were analyzed for ψ, then fractions containing ψ were pooled (fraction IV, 21.6 mg) and urea was removed by extensive dialysis against 25 mM Tris-HCl (pH 7.5), 0.1 M NaCl, 0.5 mM EDTA (3 changes of 2 liters each). Protein concentration was determined using BSA as a standard, except at the last step in which a more accurate assessment of concentration was performed by absorbance using the value $\epsilon_{280}$ equal 24,040 $M^{-1}cm^{-1}$ calculated from the sequence of holD. After the absorbance measurement, DTT was added back to 5 mM and the ψ was aliquoted and stored at −70° C.

| Fraction | | total protein (mg) | total units[1] | specific activity (units/mg) | fold purification | % yield |
|---|---|---|---|---|---|---|
| I | Solubilized pellet | 85.0 | $104.7 \times 10^7$ | $12.0 \times 10^6$ | 1.0 | 100 |
| II | Hydroxylapatite | 42.5 | $95.9 \times 10^7$ | $22.6 \times 10^6$ | 1.8 | 92 |
| III | DEAE Sepharose | 30.6 | $89.7 \times 10^7$ | $29.3 \times 10^6$ | 2.4 | 86 |
| IV | Hexlyamine Sepharose | 21.6 | $63.9 \times 10^7$ | $29.6 \times 10^6$ | 2.4 | 61 |

[1]One unit is defined as pmol of nucleotide incorporated in one minute over and above the pmol incorporated in the assay in the absence of added ψ

The pure γ protein comigrated with the γ subunit of polIII' (holoenzyme lacking only β) in a 15% SOS-polyacrylamide gel. Analysis of the N-terminal sequence of the pure cloned ψ matched that of the holD sequence and the sequence of the natural ψ from within the γχψ complex indicating that the purified protein encoded by the gene had been cloned.

The pure ψ appeared fully soluble in the absence of urea. However, a 2 mg/ml solution of ψ which appeared clear, and could not be sedimented in a table top centrifuge, still behaved as an aggregate in a gel filtration column. Therefore, even though ψ appeared soluble it wag still an aggregate. The aggregated ψ had only weak activity in the replication assay and was inefficient in binding to other proteins in physical studies. Therefore before using ψ in assays or in physical binding experiments, urea was added to a concentration of 4 M to disaggregate ψ. Once disaggregated, the urea could be quickly removed by gel filtration and ψ behaved well during filtration in the absence of urea in the column buffer. However, upon standing a full day at high concentration (>1 mg/ml) in the absence of urea, it would aggregate again. ψ would work in urea provided the preparation was sufficiently concentrated 2 mg/ml) such that it could be diluted at least 8-fold (to 0.5 M urea) for protein-protein interaction studies, 300-fold for ATPase assays, and 30,000-fold for replication assays. In 0.5 M urea, the ψ bound to γ and τ, and also to the χ subunit. ψ treated in this manner was also functional in stoichiometric amounts with other proteins in replication and ATPase assays.

In a previous study, a γχψ complex was purified by resolving the δ and δ' subunits out of the γ complex leaving only a complex of γχψ. Compared to γ, this γχψ complex was approximately 3-fold more active in reconstituting the processive polymerase with δ, β, and αε at elevated salt concentration. The simplest explanation for this result is that at elevated salt, γχψδ is more active than γδ in assembling the β ring around primed DNA.

The present invention indicates that a mixture of the γ, δ and δ' subunits formed a stabile (gel filterable) γδδ' complex when the αε complex and β subunit were incubated with the γδδ' complex (with or without χ and/or ψ) in a reaction containing SSB "coated" M13mp18 ssDNA primed with a synthetic DNA oligonucleotide and in the presence of 40 mM added NaCl, and the reaction was incubated at 37° C. for 5 minutes to allow the accessory proteins time to assemble the preinitiation complex clamp and for the αε to bind the preinitiation complex (the preinitiation complex is known to consist of a β dimer ring clamped onto the DNA). Replication of the circular DNA was then initiated upon addition of the remaining dNTPs and was quenched after 20 seconds, sufficient time for the rapid and processive holoenzyme to complete the circle.

The results indicated that as ψ is titrated into the assay the replication activity increased approximately 3.5-fold and plateaued at approximately 1 mol ψ (as monomer) per mol γδδ' complex. ψ (without χ) stimulates γδδ' and χ does not stimulate the reaction, but the presence of both χ and ψ yields the most synthesis as though χ does exert an influence on the assay but only when ψ is also present.

Previously γ was observed to contain a low level of DNA dependent ATPase activity (0.1 mol ATP hydrolyzed/mol γ/minute) compared to the ATPase of the γ complex (6.8 mol ATP/mol γ complex/minute). The Aγχψ complex resolved out of the γ complex appeared to contain approximately 3–4 fold more DNA dependent ATPase activity than γ suggesting that χ and/or ψ stimulated the ATPase activity of γ, or that there was an ATPase activity inherent within χ and/or ψ. Now that the holC and holD genes have made available pure χ and ψ in quantity, they have been studied studied them for ATPase activity and for their effect on the DNA dependent ATPase activity of γ.

As part of these studies of ATPase activity, all possible combinations of χ, ψ and ψ have been tested. These assays were performed in the presence of M13mp18 ssDNA, one of the best DNA effectors in the previous study of the γ complex ATPase activity. The results showed that ψ alone, χ alone, and a mixture of χ and ψ had no detectable ATPase activity and therefore neither ψ nor χ would appear to have an intrinsic ATPase activity, although on the basis of negative evidence we can not rule out the possibility of a cryptic ATPase; the γ subunit has a weak ATPase activity. The χ subunit has no effect on the ATPase activity of γ. However, addition of ψ to γ stimulated the ATPase activity of γ approximately 3-fold. Titration of ψ into the ATPase assay showed ψ saturated the ATPase assay at approximately 2 mol ψ (as monomer) to 1 mol γ (as dimer). Addition of the χ subunit to the γψ mixture resulted in a further 30% increase in ATPase activity.

In the presence of SSB which "coats" the ssDNA, the ATPase activity of γ, γψ and γχψ were all greatly reduced (50-fold). However, of the remaining activity, the γχψ complex was 4-fold more active than γψ showing that χ significantly stimulates the γψ ATPase which the DNA is "coated" with SSB.

The ATPase assay of ψ and χ was extended to the DNA dependent ATPase activity of the τ subunit. The τ and γ subunits are encoded by the same gene and, as a result, τ contains the γ sequence plus approximately another 24 kDa of protein which is responsible for both the ability of τ to bind DNA and to bind the polymerase subunit, α. In addition, τ has a much greater DNA dependent ATPase activity than γ, approximately 6–10 mol ATP hydrolyzed/mol τ/minute for a 60-fold greater activity of τ relative to γ.

Neither ψ, χ, or a mixture of χ and ψ had a significant influence on the ATPase activity of τ. "Coating" the ssDNA with SSB reduced the ATPase activity of τ 20-fold, and now the χ and ψ subunits stimulated the τ ATPase 10-fold to bring its activity back to about half of its value in the absence of SSB. In this case, with SSB present, the ψ stimulated τ approximately 3-fold, and χ, which had no effect on τ without ψ, stimulated the γψ ATPase another 3-fold.

To gain a better understanding of the ψ molecule the present invention studied the hydrodynamic properties of ψ in gel filtration and glycerol gradient sedimentation to determine whether ψ is a monomer or a dimer (or larger). The Stokes radius of ψ was 19 Å upon comparing its position of elution from a gel filtration column with that of protein standard of know Stokes radius. The ψ eluted in the same position as myoglobin (17.5 kDa) indicating ψ is a 15 kDa monomer rather than a dimer of 30 kDa. The γ protein sedimented with an S value of 1.95 relative to several protein standards, and was slightly slower than myoglobin which is consistent with ψ as a monomer. If a protein has an asymmetric shape, its migration will not reflect its true weight in either of these techniques. However the effect of asymmetric shape has opposite effects in these techniques and can be eliminated by the fact that the shape factor cancels when the S value and Stokes radius are both combined in one mass equation. This calculation results in a native molecular mass for ψ of 15.76 kDa, close to the 15 kDa monomeric mass of ψ calculated from its gene sequence. Hence ψ behaves as a monomer under these conditions. The frictional coefficient of ψ calculated from its Stokes radius and native mass is 1.13, slightly greater than 1.0 which indicates some asymmetry in the shape of ψ.

Although the initial use of 4 M urea would have monomerized ψ if it were a native dimer, the ψ preparation was diluted such that the concentration of urea was 0.5 M before it was applied to either the gel filtration column or the glycerol gradient, and the buffer used in the column and in the gradient contained no urea. Of course, one should still be concerned that 0.5 M urea is high enough to disaggregate a dimer of ψ and that the dimer hasn't time to reassociate during filtration and sedimentation. Yet under these very conditions it was found that ψ forms a protein-protein complex with γ, with τ and also with χ. Therefore it seems likely that if ψ were naturally a dimer, that the dimer could have reformed under these same conditions under which ψ can bind all these other subunits. Further, a monomeric nature of ψ is not unusual as most subunits of the holoenzyme are monomers when isolated (α, ε, θ, χ, δ, δ' (only γ, χ and β are dimers).

A complex of γχψ can be purified from cells indicating that ψ or χ (or both) must directly interact with γ.

Gel filtration of a mixture of γ with a 4-fold molar excess of ψ showed that ψ coeluted with the γ subunit followed later by the elution of the rest of the excess ψ. Hence, the γ subunit does in fact bind directly to γ.

The fifth subunit according to the present invention, χ, began with the N-terminal analysis of χ which provided a sequence a portion of which, was found to have been related, in part, to the sequence of the xerB gene [see EMBO 8(5): 1623 (1989)]. Although not included in the 1692 bp sequence in the publication, a fuller more complete sequence (from 1 to 2035) of the xerB gene was provided to GenBank. In this submission, the "front-end" portion of the χ gene according to the present invention was presented. However, in neither the publication nor in GenBank was the "front-end" portion as coding for a protein. Based upon the molecular weight of χ as determined in a SDS-PAG gel analysis, the "front-end" portion reported in GenBank predicts approximately 70% of the expected length of χ.

A subsequent literature study located a gene named valS which was located downstream of the xerB gene. It appeared (and was confirmed during the research leading to the present invention) that the χ, in its entirety, must be located between the xerB and valS genes.

Edman degradation amino acid sequencing was performed on an Applied Biosystems 470A gas phase microsequencing apparatus. The γχψ complex of the holoenzyme was purified, and 10 μg was electrophoresed in a 15% polyacrylamide gel [see Nature 227:680 (1970)] followed by transfer to an immobilon membrane PVDF (Millipore) for N-terminal sequence analysis as with the previous subunits according to the present invention. Internal peptide sequences were obtained by electrophoresis of 10 μg of the γχψ complex in 15% polyacrylamide gel, followed by transfer to nitrocellulose membrane, digestion by trypsin in situ, and analysis by gas phase microsequencing.

The γ or holC gene, according to the present invention, is located at 96.5 minutes on the *E. coli* chromosome and encodes a 147 amino acid protein of 16.6 kDa.

The recombinant λ phage 5C4 from the overlapping λ library of Kohara [see Cell 50:495 (1987)] was used in determining the DNA Sequence of the χ gene. The DNA fragment containing the χ gene was identified and cloned into pUC18 using conventional techniques. The DNA sequence for both strands of the χ gene were performed on the dublex plasmid by the dideoxy chain termination method of Sanger using the Sequenase kit; sequencing reactions were analyzed on 6% polyacrylamide, 50% (w/v) urea gels.

The sequence of the primers (5'→3') used for PCR amplification of the χ gene during the cloning of the χ gene are as follows:

30-mer primer:

CCCCA<u>CATAT</u> GAAAAACGCG ACGTTCTACC 30;

28-mer primer:

ACCC<u>GGATCC</u> AAACTGCCGG TGACATTC 28

The 30-mer hybridizes over the initiation codon of χ, and a two nucleotide mismatch results in a NdeI restriction site (underlined) at the ATG initiation codon upon amplification of the gene. The 28-mer anneals within the valS gene downstream of the c gene; a BamHI restriction site (underlined) is embedded within the six nucleotides which do not hybridize to valS.

Using these codons, subsequent studies isolated the c gene sequence which is, according to the present invention:

| | | | | | | | | | | | | | |
|---|---|---|---|---|---|---|---|---|---|---|---|---|---|
| ATG | AAA | AAC | GCG | ACG | TTC | TAC | CTT | CTG | GAC | AAT | GAC | ACC | 39 |
| ACC | GTC | GAT | GGC | TTA | AGC | GCC | GTT | GAG | CAC | CTG | GTG | TGT | 78 |
| GAA | ATT | GCC | GCA | GAA | CGT | TGG | CGC | AGC | GGT | AAG | CGC | GTG | 117 |

```
CTC ATC GCC TGT GAA GAT GAA AAG CAG GCT TAC GCC CTG      156

GAT GAA GCC CTG TGG GCG CGT CCG GCA GAA AGC TTT GTT      195

CCG CAT AAT TTA GCG GGA GAA GGA CCG CGC GGC GGT GTA      234

CCG GTG GAG ATC GCC TGG CCG CAA AAG CGT AGC AGC AGC      273

CGG CGC GAT ATA TTG ATT AGT CTG CGA ACA AGC TTT GCA      312

GAT TTT GCC ACC GCT TTT ACA GAA GTG GTA GAC TTC GTT      351

CCT CAT GAA GAT TCT CTG AAA CAA CTG GCG CGC GAA CGC      390

TAT AAA GCC TAC CGC GTG GCT GGT TTC AAC CTG AAT ACG      429

GCA ACT TGG AAA                                          441
```

The upstream portion of the holC gene is:

```
TAACGGCGAA GAGTAATTGC GTCAGGCAAG GCTGTTATTG CCGGATGCGG     50

CGTGAACGCC TTATCCGACC TACACAGCAC TGAACTCGTA GGCCTGATAA    100

GACACAACAG CGTCGCATCA GGCGCTGCGG TGTATACCTG ATGCGTATTT    150

AAATCCACCA CAAGAAGCCC CATTT                              175
```

The downstream sequence begins with the stop codon:

```
TAA TGGAAAA GACATATAAC CCACAAGATA TCGAACAGCC              40

GCTTTACGAG CACTGGGAAA AAAGCCAGGA AAGTTTCTGC               80

ATCATGATCC CGCCGCCGAA                                    100
```

The underlined nucleotide sequences indicate the potential Shine-Dalgarno sequence (AAGAAG) of holC and the nearest possible promoter signals (TTGCCG and TATCCG) are highlighted in the first underlined region. The stop codon of the upstream XerB gene (TAA) and the start codon of the downstream ValS gene (ATG) are each double underlined.

This translated into the correct peptide which is:

```
Met Lys Asp Ala Thr Phe Tyr Leu Leu Asp Asn Asp Thr Thr Val
                  5                  10                  15

Asp Gly Leu Ser Ala Val Glu Gln Leu Val Cys Glu Ile Ala Ala
                 20                  25                  30

Glu Arg Trp Arg Ser Gly Lys Arg Val Leu Ile Ala Cys Glu Asp
                 35                  40                  45

Glu Lys Gln Ala Tyr Arg Leu Asp Glu Ala Leu Trp Ala Arg Pro
                 50                  55                  60

Ala Glu Ser Phe Val Pro His Asn Leu Ala Gly Glu Gly Pro Arg
                 65                  70                  75

Gly Gly Ala Pro Val Glu Ile Ala Trp Pro Gln Lys Arg Ser Ser
                 80                  85                  90

Ser Arg Arg Asp Ile Leu Ile Ser Leu Arg Thr Ser Phe Ala Asp
                 95                 100                 105

Phe Ala Thr Ala Phe Thr Glu Val Val Asp Phe Val Pro Tyr Glu
                110                 115                 120

Asp Ser Leu Lys Gln Leu Ala Arg Glu Arg Tyr Lys Ala Tyr Arg
                125                 130                 135

Val Ala Gly Phe Asn Leu Asn Thr Ala Thr Trp Lys
                140                 145     147
```

EXAMPLE IV

Molecular Cloning, Cell Growth and Purification

PCR reactions were performed with both Vent polymerase (Biolabs) and Taq polymerase. In a 100 μl volume, the PCR reaction was conducted in a reaction buffer containing 10 mM Tris-HCl (pH 8.3), 50 mM KCl, 1.5 mM $MgCl_2$, and 0.01% (w/v) gelatin, 1.0 μM of each primer, and 200 μM each dNTP (Pharmacia-LKB), on 1 ng E. coli genomic DNA (prepared from K12 strain C600) with 2.5 u polymerase. PCR amplification was performed in a DNA Thermal cycler model 9801 using the following cycle: melting temperature 94° C. for 1 min, annealing temperature 60° C. for 2 min, and extension temperature 72° C. for 2 min. After 30 cycles, the amplified DNA was purified by phenol extraction in 2% SDS followed by sequential digestion of 10 μg DNA with 10 u NdeI, followed by 10 u BamHI. The 600 bp DNA fragment was purified from a 0.8% agarose gel by electroelution, and ligated into pET3c previously digested with both NdeI and BamHI restriction enzymes. The resulting plasmids (pETχ-1, pETχ-2 and pETχ-3) were ligated into E. coli strain BL21(DE3)pLysS.

The freshly transformed BL21(DE3)pLysSpETχ cells were grown in LB media containing 100 μg/ml ampicillin and 30 μg/ml chloramphenicol at 37° C. Upon growth to an $OD_{600}$ of 0.7, isopropyl B-D-galactopyranoside (IPTG) was added to a final concentration of 0.4 mM. Incubation was continued for 3 hr at 37° C. before harvesting the cells.

Seven mg of homogeneous χ protein was purified from a 4-liter induced culture in which nearly 30% overproduced χ protein was in soluble form. The 4-liter culture was grown in an $OD_{600}$ of 0.7 before addition of IPTG to 0.4 mM. After a further 3 hr incubation at 37° C., the cells (25 g) were harvested, resuspended in 25 ml ice-cold 50 mM tris/10% sucrose, and lysed by 25 mg lysozyme on ice for 45 min and a subsequent incubation at 37° C. for 5 min in 5 mM Tris, 1% sucrose, 30 mM spermidine, and 100 mM NaCl. The cell lysate was clarified by centrifugation at 12,000 rpm for 1 hr at 4° C. All subsequent column chromatography procedures were at 4° C. All the columns were equilibrated in buffer A (20 mM tris (pH 7.5), 0.5 mM EDTA, 5 mM DTT, and 20% glycerol). The χ protein was followed through the purification process by SDS-PAGE gel analysis. Total protein was estimated [see Anal. Biochem 72:248,(1976)] using bovine serum albumin as a standard. The soluble lysate (120 ml, 520 mg protein) was dialyzed against 4 liter buffer A for 16 hours before being loaded onto a 60 ml heparin-agarose column. The fractions containing χ, which eluted off the sepharose fast flow column. The Q sepharose fast flow column was eluted with a 650-ml linear gradient of 0 M to 0.5 M NaCl in buffer A. The fractions containing χ, eluted at approximately 0.16 M salt in a volume of 45 ml (60 mg protein), were pooled, dialyzed overnight against 4 liter buffer A, and loaded onto a 1 ml N-6 ATP-agarose column. The γ complex (γδδ'χψ) binds to the column tightly due to the strong ATP binding capacity of γ, while χ protein by itself flows through. This column was included to eliminate any γ complex from the χ preparation.

The flow-through of the ATP-agarose column was loaded onto an 8 ml hexylamine column and χ was eluted with an 80 ml linear gradient of 0 to 0.5 M NaCl in buffer A. The χ protein eluted at approximately 0.25 M salt. Fractions containing the peptide (81 ml, 36 mg protein) were pooled and dialyzed against buffer A. The χ protein was loaded onto an 8 ml FPLC Mono Q column, and eluted with a 80 ml linear gradient of 0 to 0.5 M NaCl in buffer A. The fractions containing χ (28 ml 8.5 mg protein) eluted sharply at 0.16 M salt. The χ protein was pooled and dialyzed overnight against 4 liters of buffer A, then aliquoted and stored at −70° C.

The concentration of purified χ protein was determined from its absorbance at 280 nm. The molar extinction coefficient at 280 nm ($\epsilon_{280}$) of a protein in its native state can be calculated from its gene sequence to within +/−5% by using the equation $\epsilon_{280} = Trp_m(5690 \text{ M}^{-1}\text{cm}^{-1}) + Tyr_n(1280 \text{ M}^{-1}\text{cm}^{-1})$ [see Analytical Biochemistry 182:319 (1989)] wherein m and n are the numbers of tryptophan and tyrosine residues, respectively, in the peptide. The molar extinction coefficients of tryptophan and tyrosine are known [see Biochemistry 6:1948 (1967)]. For χ protein where m equals 4 and n equals 5, $\epsilon_{280} = 29,160 \text{ M}^{-1}\text{cm}^{-1}$. The χ protein was dialyzed against buffer A containing no DTT prior to absorbance measurement. SDS-PAG was in 15% polyacrylamide 0.1% SDS gel in Tris/glycine/SDS buffer [see Nature 227:680 (1970)]. Proteins were visualized by Coomassie Brilliant Blue Stain.

The γχψ complex was purified from 1.3 kg of E. coli. The χ subunit was resolved from the γ and ψ subunits upon electorphoresis in a 15% SDS polyacrylamide gel followed by transfer of χ onto PVDF membrane for N-terminal sequence analysis (210 pmol), and onto nitrocellulose membrane for tryptic analysis (300 pmol). Proteins were visualized by Ponceau S stain. The amino terminus of c was determined to be:

```
NH2-Met Lys Asn Ala Thr Phe Tyr Leu Leu Asp Asn Asp Thr Thr Val
              5                   10                  15

Asp Gly Leu Ser Ala Val Glu Gln Leu Val Xxx Glu Ile Ala
                      20                  25
``` column during wash with buffer A, were pooled (360 ml, 365 mg protein), and loaded directly onto a FPLC 26/10 Q wherein Xxx is an unidentified residue. Tryptic digestion and analysis of four internal peptides were determined to be:

```
χ-1:
NH2-Val Leu Ile Ala Xxx Glu Asp Glu Lys
                  5

χ-2:
NH2-Leu Asp Glu Ala Leu Trp Ala Ala Pro Ala Glu Ser Phe Val Pro
                  5                   10                  15
```

-continued

```
His Asn Leu Ala Gly Glu
                      20

χ-3:
NH₂-Gly Gly Ala Pro Val Glu Ile Ala Trp Pro
              5                          10

χ-4:
NH₂-Gly Phe Asn Leu Asn Thr Ala Thr
              5
```

The 3.4 kb BamHI fragment containing holC was excised from λ 5C4 and ligated into the BamHI site of pUC-χ. Both strands of the holC gene were sequenced on the duplex plasmid by the chain termination method of Sanger and synthetic 17-mer DNA oligonucleotides. Sequencing reactions were analyzed on 6% (w/v) acrylamide, 50% (w/v) urea gels and were performed with both dGTP and DITP.

The sequences of the primers used to amplify the holC gene were:
upstream 30-mer:
  CCCACATAT GAAAAACGCG ACGTTCTACC 30
Downstream 28-mer:
  ACCCGGATCC AAACTGCCGG TGACGTTC 28

The upstream 30-mer hybridizes over the initiation codon of holC, and a two-nucleotide mismatch results in a NdeI restriction site (underlined above) at the ATG initiation codon upon amplification of the gene. The downstream 28-mer sequence within the valS gene downstream of holC. A BamHI restriction site (underlined) is embedded in the sequence resulting in three nucleotides which are not complementary to valS. Amplification reactions contained 1.0 μM of each primer, 200 μM of each dNTP, 1 ng E. coli genomic DNA (from strain C600), and 2.5 units of Taq I DNA polymerase in a final volume of 100 μl 10 mM Tris-HCl (pH 8.3), 50 mM KCl, 1.5 mM MgCl₂, and 0.01% (w/v) gelatin. Amplification was performed in a thermal cycler using the following cycle: 94° C., 1 minute; 60° C., 2 minutes, and 72° C., 2 minutes. After 30 cycles, the amplified 604 bp DNA was purified by phenol extraction in 2% SDS followed by sequential digestion of 10 μg DNA in 10 units of NdeI and then 10 units of BamHI according to manufacturer's specifications. The NdeI-BamHI fragment was electroeluted from a 0.8% agarose gel and ligated into gel purified pET3c previously digested with both NdeI and BamHI. The resulting plasmid, pET-χ was sequenced which confirmed that no errors had been introduced during amplification, and it was then transformed into strain BL21 (DE3)plysS.

The γ subunit was purified from an overproducing strain, and the δ, δ' and ψ subunits were purified from their respective overproducing strains as described above. A mixture of 48 g γ (0.51 nmol as dimer), 144 μg δ (3.7 nmol as monomer), 144 μg δ' (3.9 nmol as monomer), and 192 μg ψ (12.7 nmol as monomer) was incubated at 15° C. for 1 hour and then loaded onto a 1 ml HR 5/5 Mono Q column. The concentration of γ was determined using BSA as a standard. Concentrations of δ, δ' and ψ were determined from their absorbance at 280 nm using the molar extinction coefficients, 46,137 $M^{-1}cm^{-1}$, 60,136 $M^{-1}cm^{-1}$, and 24040 $M^{-1}cm^{-1}$, respectively. The column was eluted with a 32 ml gradient of 0 M–0.4 M NaCl in 20 mM Tris-HCl (pH 7.5), 0.5 mM EDTA, 2 mM DTT, and 20% glycerol (buffer A) whereupon the γδδ'ψ complex resolved from uncomplexed subunits by eluting later than all the rest. Eighty fractions were collected and analyzed by a Coomassie Blue stained 15% SDS polyacrylamide gel. Fractions containing the γδδ'ψ complex, were pooled, the protein concentration was determined using BSA as a standard, and then the γδδ'ψ complex was aliquoted and stored at −70° C. Molarity of γδδ' was calculated from the protein concentration assuming the 185 kDa mass calculated from gene sequences assuming a stoichiometry of $γ_2δ_1δ'_1ψ_1$ as expected from the tentative stoichiometry of subunits in the γ complex.

The reconstitution assay contained 72 ng M13mp18 ssDNA, (0.03 pmol as circles) uniquely primed with a DNA 30-mer, 980 ng SSB (13.6 pmol as tetramer), 10 ng β (0.13 pmol as dimer), 55 ng αε complex (0.35 pmol) in a final volume (after addition of proteins) of 25 μl 20 mM Tris-HCl (pH 7.5), 0.1 mM EDTA, 8 mM MgCl₂, 5 mM DTT, 4% glycerol, 40 μg/ml BSA, 0.5 mM ATP, 40 mM NaCl, 60 μM each dCTP, dGTP, dATP, and 20 μM [α-$^{32}$P]. Pure χ protein or column pool containing χ (1–12 ng) was preincubated on ice for 30 minutes with 37 ng γδδ'ψ complex (0.2 pmol) in 20 μl of 20 mM Tris-HCl (pH 7.5), 2 mM DTT, 0.5 mM EDTA, 20% glycerol, and 50 μg/ml BSA before dilution with the same buffer such that 0.14 ng (0.76 fmol) of the γδδ'ψ complex was added to the assay in a 1–2 μl volume. The assay was then shifted to 37° C. for 5 minutes. DNA synthesis was quenched by spotting directly onto DE81 filter paper and quantitated. The αε complex, β and SSB proteins used in the reconstitution assay were purified and their concentrations determined using BSA as a standard except for 6 which was determined by absorbance using an ε280 value of 17,900 $M^{-1}cm^{-1}$.

Gel filtration analysis was performed using the Pharmacia HR 10/30 fast protein liquid chromatography columns; Superdex 75 and Superose 12. Proteins were incubated together for 1 hour at 15° C. in a final volume of 200 μl buffer B (25 mM Tris-HCl (pH 7.5), 1 mM EDTA, 10% glycerol, and 100 mM NaCl). The ψ protein was first brought to 4 M in urea to disaggregate it, and when present with other proteins the final concentration of urea in buffer B was 0.5 M. The entire sample was injected, the column was developed with buffer B, and after collecting the first 6 ml, fractions of 170 μl were collected. The χ protein was located in column fractions by analysis in 15% SDS-polyacrylamide gels. Densitometry of Coomassie Blue-stained gels was performed using a laser densitometer (Ultrascan XL).

Individual samples of χ (46 ng, 2.8 nmol as monomer) and of ψ (45 ng, 3 nmol as monomer), and a mixture of χ (218 ng, 13 nmol as monomer) and ψ (45 ng, 3 nmol as monomer) were incubated 30 minutes at 4° C. in 200 μl buffer B with 5% glycerol (samples containing ψ contained a final concentration of 0.5 M urea in the 200 μl as explained above). Samples were layered onto 12.3 ml gradients of 10%–30% glycerol in 25 mM Tris-HCl (pH 7.5), 0.1 M NaCl and 1 mM EDTA. Protein standards in 200 μl of buffer B with 5% glycerol were layered onto another gradient and the gradients were centrifuged at 270,000×g for 44 hours at 4° C. Fractions were collected and analyzed.

The polymerase chain reaction was used to precisely clone the holC gene into the T7 based pET expression system [see Methods in Enzymology 185:60 (1990)]. Primers upstream and downstream of holC were synthesized to amplify a 604 bp fragment containing the holC gene from E. coli genomic DNA. The upstream primer hybridized over the start codon of holC and included two mismatched nucleotides in order to create an NdeI restriction site at the initiating ATG. The primer downstream of holC included three mismatched nucleotides to create a BamHI restriction site. The amplified 604 bp fragment was digested with NdeI and BamHI and cloned into the NdeI-BamHI site of the T7 based expression vector pET3c to yield pET-χ. In the pET-χ plasmid, the holC gene is under the control of a strong T7 RNA polymerase promoter and an efficient Shine-Dalgarno sequence in favorable context for translation initiation. DNA sequencing of the pET-χ plasmid showed its sequence was identical to that of pUC-χ, and therefore no errors were incurred during amplification.

The pET-χ expression plasmid was introduced into strain BL21(DE)plyS which is a lysogen carrying the T7 RNA polymerase gene under the control of the IPTG-inducible lac UV5 promoter. Upon induction with IPTG and continued growth for 3 hours, the χ protein was expressed to a level of 27% total cell protein. Upon cell lysis, only about 30% of the χ protein was in the soluble fraction, the rest being found in the cell debris. Induction at lower temperature (20° C.) or for shorter times did not appear to increase the proportion of χ in the soluble fraction.

Four liters of induced cells were lysed and 38 mg of pure χ was obtained in 38% overall yield upon fractionation with ammonium sulfate precipitation, followed by column chromatography using Q sepharose and heparin agarose. The χ protein was well behaved throughout the purification and showed no tendency to aggregate. The N-terminal sequence analysis of the pure cloned χ matched that of the holC gene indicating that the protein had been successfully cloned and purified. The expressed c protein also comigrated with the authentic χ subunit contained within polIII'.

In summary, as a result of the present invention, the location and sequence of χ was determined. The χ subunit (400 pmol) was separated from γ and χ subunits of the γχψ complex by SDS denaturation and resolution on a 15% polyacrylamide gel, and 100 pmol transferred to a PVDF immobilon membrane for amino terminal sequence analysis; the remainder was transferred to nitrocellulose for sequence analysis of internal peptides following trypsin digestion. After transfer, the protein was visualized by Ponceau S stain and excised from the gel. The sequence of the N-terminal amino acids and four internal peptides were determined as described above, and these sequences were used to search the GenBank database. One single exact match was found at about 96.5 minutes on the E. coli chromosome between the xerB and valS genes.

The recombinant Kohara λ clone 5C4, contains the DNA fragment encompassing the xerB and partial valS genes, and the χ gene was subcloned by ligation of the BamHI fragment of λ 5C4 into pUC18. Sequence analysis was performed directly on the plasmid. As shown above, the open reading frame of the χ gene was 441 nucleotides long. Its initiation codon is 160 nucleotides downstream of the stop codon of the xerB gene, while its termination codon, TAA, has one base overlapping with the start codon of the valS gene. Since the xerB and χ genes were transcribed in the same direction, and that no promoter consensus sequences were found for the χ gene alone, suggests that these two genes are in the same operon.

When PCR was applied to clone the χ gene into the T7 based expression system, PCR primers based upon the known sequences of the xerB and valS genes were made to amplify the fragment between the two genes. As described, E. coli genomic DNA was used as the PCR template, and a fragment of approximately 600 base pairs was amplified. The PCR fragment, after being digested with NdeI and BamHI, was cloned into the NdeI-BamHI site of the expression vector pET3c in similar manner to what was done with the preceding gene sequences. Thus, the putative χ gene was put under the control of a strong T7 RNA polymerase promoter gene as well as the efficient translation initiation signal, and transcription termination sequence downstream of the BamHI site. Direct DNA sequencing of the plasmids formed showed that they were all identical to the sequence of the χ clone.

The resulting plasmids were transformed into E. coli BL21(DE)pLysS that contained a lysogen carrying the T7 RNA polymerase gene under the control of the IPTG-inducible lac UV5 promoter [see Methods in Enzymology, 185:60 (1990)]. Transformants were selected by ampicillin and chloramphenicol resistance, and subsequently subjected to IPTG induction as described above. A protein of about 17 kDa was overproduced in all three PCR clones. The γ complex was run in parallel with the three clones on SDS-PAG gel, and when the overproduced and the χ subunit were at similar amounts, they showed the same gel mobility. This observation supported the identity of the overproduced protein as the χ subunit.

In addition to the specific sequences provided above for the individual genes according to the present invention, the present invention also extends to mutations, deletions and additions to these sequences provided such changes do not substantially affect the present properties of the listed sequences.

As described, the naturally occurring holoenzyme consists of 10 protein subunits and is capable of extending DNA faster than polymerase I, and producing a product many times larger then the polymerase I enzyme. Thus, these unique properties of the 5, preferably 6, active subunits of the present invention are likely to find wide application in, for example, long chain PCR—using the active sequence according to the present invention PCR can be performed over several tens of kb; PCR performed at room temperature—the active sequence according to the present invention is uniquely adapted to be a polymerase of choice for PCR at room temperature due to its high fidelity; extension of site mutated primers without catalyzing strand displacement; and for sequencing operations wherein other polymerases find difficulty. Other uses will become more apparent to those skilled in the art as the science of molecular genetics continues to progress.

The sequence listing for the nucleic acid sequences and peptide sequences which are contained in the present description is as follows:

Thus, while I have illustrated and described the preferred embodiment of my invention, it is to be understood that this invention is capable of variation and modifications and I therefore do not wish to be limited to the precise terms set forth, but desire to avail myself of such changes and alterations which may be made for adapting the invention to various usages and conditions. Accordingly, such changes and alterations are properly intended to be within the full range of equivalents, and therefore within the purview of the following claims.

Having thus described my invention and the manner and a process of making and using it in such full, clear, concise and exact terms so as to enable any person skilled in the art to which it pertains, or with which it is most nearly connected, to make and use the same.

I claim:

1. An isolated DNA molecule encoding a protein δ' subunit of polymerase III holoenzyme, wherein a polymerase III holoenzyme comprising the subunit is capable of stimulating DNA synthesis, wherein the DNA molecule comprises a nucleic acid sequence which hybridizes to a nucleotide sequence corresponding to SEQ ID NO. 13 when hybridization is performed in 2×SSC, 0.2% SDS at 53° C.

2. The isolated DNA molecule according to claim 1, wherein the subunit has a molecular weight of 36.9 kDa.

3. The isolated DNA molecule according to claim 1, wherein the protein has an amino acid sequence corresponding to SEQ. ID. No. 10.

4. The isolated DNA molecule according to claim 1, wherein the DNA molecule has a nucleotide sequence corresponding to SEQ. ID. No. 13.

5. An expression system comprising a DNA molecule, according to claim 1 in a vector heterologous to the DNA molecule.

6. A host cell transformed with a heterologous DNA molecule according to claim 1.

7. An isolated protein δ' subunit of polymerase III holoenzyme, wherein a polymerase III holoenzyme comprising the subunit is capable of stimulating DNA synthesis, wherein the protein subunit is encoded by a DNA molecule comprising a nucleic acid sequence which hybridizes to a nucleotide sequence corresponding to SEQ ID NO. 13, when hybridization is performed in 2×SSC, 0.2% SDS at 53° C.

8. The isolated protein subunit according to claim 7, wherein the protein has a molecular weight of 36.9 kDa.

9. The isolated protein subunit according to claim 7, wherein the isolated protein subunit comprises an amino acid sequence of SEQ. ID. No. 10.

10. An isolated protein δ subunit of polymerase III holoenzyme, wherein the subunit is capable of stimulating DNA synthesis by the polymerase III holoenzyme wherein the protein subunit is encoded by a DNA molecule comprising a nucleic acid sequence which hybridizes to a nucleotide sequence corresponding to SEQ. ID. NO. 6 when hybridization is performed in 2×SSC, 0.2% SDS at 53° C.

11. The isolated protein subunit of polymerase III holoenzyme according to claim 10, wherein the isolated protein subunit comprises an amino acid sequence of SEQ. ID. No. 9.

12. The isolated protein subunit according to claim 10, wherein the protein subunit enhances the DNA stimulated ATPase activity of a second protein subunit.

13. An isolated DNA molecule encoding a protein δ subunit of polymerase III holoenzyme, wherein the subunit is capable of stimulating DNA synthesis by the polymerase III holoenzyme wherein the DNA molecule comprises a nucleic acid sequence which hybridizes to a nucleotide sequence corresponding to SEQ. ID. NO. 6 when hybridization is performed in 2×SSC, 0.2% SDS at 53° C.

14. The isolated DNA molecule according to claim 13, wherein the isolated DNA molecule comprises a nucleotide sequence of SEQ. ID. No. 6.

15. The isolated DNA molecule according to claim 13, wherein the protein has an amino acid sequence corresponding to SEQ. ID. No. 9.

16. An expression system comprising a DNA molecule, according to claim 13 in a vector heterologous to the DNA molecule.

17. A host cell transformed with a heterologous DNA molecule according to claim 13.

18. An isolated DNA molecule consisting of SEQ ID NO. 11 or SEQ ID NO. 12.

19. An isolated protein consisting of the amino acid sequence encoded by SEQ ID NO. 11 or SEQ ID NO. 12.

* * * * *

SEQUENCE LISTING

<160> NUMBER OF SEQ ID NOS: 60

<210> SEQ ID NO 1
<211> LENGTH: 28
<212> TYPE: PRT
<213> ORGANISM: Escherichia coli

<400> SEQUENCE: 1

Met Leu Arg Leu Tyr Pro Glu Gln Leu Arg Ala Gln Leu Asn Glu Gly
1               5                   10                  15

Leu Arg Ala Ala Tyr Leu Leu Leu Gly Asn Asp Pro
            20                  25

<210> SEQ ID NO 2
<211> LENGTH: 21
<212> TYPE: PRT
<213> ORGANISM: Escherichia coli

<400> SEQUENCE: 2

Ala Ala Tyr Leu Leu Leu Gly Asn Asp Pro Leu Leu Leu Gln Glu Ser
1               5                   10                  15

Gln Asp Ala Val Arg
            20

<210> SEQ ID NO 3
<211> LENGTH: 14
<212> TYPE: PRT
<213> ORGANISM: Escherichia coli

<400> SEQUENCE: 3

Ala Gln Glu Asn Ala Ala Trp Phe Thr Ala Leu Ala Asn Arg
1               5                   10

<210> SEQ ID NO 4
<211> LENGTH: 24
<212> TYPE: PRT
<213> ORGANISM: Escherichia coli

<400> SEQUENCE: 4

Val Glu Gln Ala Val Asn Asp Ala Ala His Phe Thr Pro Phe His Trp
1               5                   10                  15

Val Asp Ala Leu Leu Met Gly Lys
            20

<210> SEQ ID NO 5
<211> LENGTH: 33
<212> TYPE: DNA
<213> ORGANISM: Escherichia coli

<400> SEQUENCE: 5
gtacaaccga atcatatgtt acccagcgag ctc                                 33

<210> SEQ ID NO 6
<211> LENGTH: 1032
<212> TYPE: DNA
<213> ORGANISM: Escherichia coli

<400> SEQUENCE: 6
atgattcggt tgtacccgga acaactccgc gcgcagctca atgaagggct gcgcgcggcg    60
tatcttttac ttggtaacga tcctctgtta ttgcaggaaa gccaggacgc tgttcgtcag   120

```
gtagctgcgg cacaaggatt cgaagaacac cacactttt ccattgatcc caacactgac    180
tggaatgcga tcttttcgtt atgccaggct atgagtctgt tgccagtcg acaaacgcta    240 ttgctgttgt taccagaaaa cggaccgaat gcggcgatca atgagcaact tctcacactc    300
accggacttc tgcatgacga cctgctgttg atcgtccgcg gtaataaatt aagcaaagcg    360
caagaaaatg ccgcctggtt tactgcgctt gcgaatcgca gcgtgcaggt gacctgtcag    420
acaccggagc aggctcagct tccccgctgg gttgctgcgc gcaaaaca gctcaactta     480 gaactggatg acgcggcaaa tcaggtgctc tgctactgtt atgaaggtaa cctgctggcg    540
ctggctcagg cactggagcg tttatcgctg ctctggccag acggcaaatt gacattaccg    600
cgcgttgaac aggcggtgaa tgatgccgcg catttcaccc cttttcattg ggttgatgct    660
ttgttgatgg gaaaaagtaa gcgcgcattg catattcttc agcaactgcg tctggaaggc    720
agcgaaccgg ttattttgtt gcgcacatta acgtgaac tgttgttact ggttaacctg      780
aaacgccagt ctgcccatac gccactgcgt gcgttgtttg ataagcatcg ggtatggcag    840
aaccgccggg gcatgatggg cgaggcgtta atcgcttaa gtcagacgca gttacgtcag     900
gccgtgcaac tcctgacacg aacggaactc accctcaaac aagattacgg tcagtcagtg    960
tgggcagagc tggaagggtt atctcttctg ttgtgccata acccctggc ggacgtattt    1020 atcgacggtt ga                                                       1032

<210> SEQ ID NO 7
<211> LENGTH: 127
<212> TYPE: DNA
<213> ORGANISM: Escherichia coli

<400> SEQUENCE: 7
ccgaacagct gattcgtaag ctgccaagca tccgtgctgc ggatattcgt tccgacgaag     60
aacagacgtc gaccacaacg gatactccgg caacgcctgc acgcgtctcc accacgctgg    120
gtaactg                                                              127

<210> SEQ ID NO 8
<211> LENGTH: 104
<212> TYPE: DNA
<213> ORGANISM: Escherichia coli

<400> SEQUENCE: 8
tgaatgaaat ctttacaggc tctgtttggc ggcacctttg atccggtgca ctatggtcat     60
ctaaaacccg ttggaagcgt ggccgaagtt ttgattggtc tgac                     104

<210> SEQ ID NO 9
<211> LENGTH: 343
<212> TYPE: PRT
<213> ORGANISM: Escherichia coli

<400> SEQUENCE: 9
```

Met Ile Arg Leu Tyr Pro Glu Gln Leu Arg Ala Gln Leu Asn Glu Gly
 1               5                  10                  15

Leu Arg Ala Ala Tyr Leu Leu Leu Gly Asn Asp Pro Leu Leu Leu Gln
                20                  25                  30

Glu Ser Gln Asp Ala Val Arg Gln Val Ala Ala Gln Gly Phe Glu
        35                  40                  45

Glu His His Thr Phe Ser Ile Asp Pro Asn Thr Asp Trp Asn Ala Ile
    50                  55                  60

Phe Ser Leu Cys Gln Ala Met Ser Leu Phe Ala Ser Arg Gln Thr Leu

```
                65                  70                  75                  80
Leu Leu Leu Leu Pro Glu Asn Gly Pro Asn Ala Ala Ile Asn Glu Gln
                    85                  90                  95

Leu Leu Thr Leu Thr Gly Leu Leu His Asp Asp Leu Leu Leu Ile Val
                    100                 105                 110

Arg Gly Asn Lys Leu Ser Lys Ala Gln Glu Asn Ala Ala Trp Phe Thr
                    115                 120                 125

Ala Leu Ala Asn Arg Ser Val Gln Val Thr Cys Gln Thr Pro Glu Gln
            130                 135                 140

Ala Gln Leu Pro Arg Trp Val Ala Arg Ala Lys Gln Leu Asn Leu
145                 150                 155                 160

Glu Leu Asp Asp Ala Ala Asn Gln Val Leu Cys Tyr Cys Tyr Glu Gly
                    165                 170                 175

Asn Leu Asn Leu Ala Gln Ala Leu Glu Arg Leu Ser Leu Leu Trp
                180                 185                 190

Pro Asp Gly Lys Leu Thr Leu Pro Arg Val Glu Gln Ala Val Asn Asp
                    195                 200                 205

Ala Ala His Phe Thr Pro Phe His Trp Val Asp Ala Leu Leu Met Gly
            210                 215                 220

Lys Ser Lys Arg Ala Leu His Ile Leu Gln Gln Leu Arg Leu Gly Gly
225                 230                 235                 240

Ser Glu Pro Val Ile Leu Leu Arg Thr Leu Gln Arg Glu Leu Leu Leu
                    245                 250                 255

Leu Val Asn Leu Lys Arg Gln Ser Ala His Thr Pro Leu Arg Ala Leu
                260                 265                 270

Phe Asp Lys His Arg Val Trp Gln Asn Arg Arg Gly Met Met Gly Glu
                275                 280                 285

Ala Leu Asn Arg Leu Ser Gln Thr Gln Leu Arg Gln Ala Val Gln Leu
            290                 295                 300

Leu Thr Arg Thr Glu Leu Thr Leu Lys Gln Asp Tyr Gly Gln Ser Val
305                 310                 315                 320

Trp Ala Glu Leu Glu Gly Leu Ser Leu Leu Cys His Lys Pro Leu
                325                 330                 335

Ala Asp Val Phe Ile Asp Gly
                340

<210> SEQ ID NO 10
<211> LENGTH: 334
<212> TYPE: PRT
<213> ORGANISM: Escherichia coli

<400> SEQUENCE: 10

Met Arg Trp Tyr Pro Trp Leu Arg Pro Asp Phe Glu Lys Leu Val Ala
1               5                   10                  15

Ser Tyr Gln Ala Gly Arg Gly His His Ala Leu Leu Ile Gln Ala Leu
                20                  25                  30

Pro Gly Met Gly Asp Asp Ala Leu Ile Tyr Ala Leu Ser Arg Tyr Leu
            35                  40                  45

Leu Cys Gln Gln Pro Gln Gly His Lys Ser Cys Gly His Cys Arg Gly
        50                  55                  60

Cys Gln Leu Met Gln Ala Gly Thr His Pro Asp Tyr Tyr Thr Leu Ala
65                  70                  75                  80

Pro Glu Lys Gly Lys Asn Thr Leu Gly Val Asp Ala Val Arg Glu Val
                    85                  90                  95
```

```
Thr Glu Lys Leu Asn Glu His Ala Arg Leu Gly Gly Ala Lys Val Val
            100                 105                 110

Trp Val Thr Asp Ala Ala Leu Leu Thr Asp Ala Ala Ala Asn Ala Leu
        115                 120                 125

Leu Lys Thr Leu Glu Glu Pro Pro Ala Glu Thr Trp Phe Phe Leu Ala
    130                 135                 140

Thr Arg Glu Pro Glu Arg Leu Leu Ala Thr Leu Arg Ser Arg Cys Arg
145                 150                 155                 160

Leu His Tyr Leu Ala Pro Pro Glu Gln Tyr Ala Val Thr Trp Leu
                165                 170                 175

Ser Arg Glu Val Thr Met Ser Gln Asp Ala Leu Leu Ala Ala Leu Arg
            180                 185                 190

Leu Ser Ala Gly Ser Pro Gly Ala Ala Leu Ala Leu Phe Gln Gly Asp
        195                 200                 205

Asn Trp Gln Ala Arg Glu Thr Leu Cys Gln Ala Leu Ala Tyr Ser Val
    210                 215                 220

Pro Ser Gly Asp Trp Tyr Ser Leu Leu Ala Ala Leu Asn His Glu Gln
225                 230                 235                 240

Ala Pro Ala Arg Leu His Trp Leu Ala Thr Leu Leu Met Asp Ala Leu
                245                 250                 255

Lys Arg His His Gly Ala Ala Gln Val Thr Asn Val Asp Val Pro Gly
            260                 265                 270

Leu Val Ala Glu Leu Ala Asn His Leu Ser Pro Ser Arg Leu Gln Ala
        275                 280                 285

Ile Leu Gly Asp Val Cys His Ile Arg Glu Gln Leu Met Ser Val Thr
    290                 295                 300

Gly Ile Asn Arg Glu Leu Leu Ile Thr Asp Leu Leu Leu Arg Ile Glu
305                 310                 315                 320

His Tyr Leu Gln Pro Gly Val Val Leu Pro Val Pro His Leu
                325                 330

<210> SEQ ID NO 11
<211> LENGTH: 57
<212> TYPE: DNA
<213> ORGANISM: Escherichia coli

<400> SEQUENCE: 11
actctggaag aaccgccggc tgaaacttgg ttttttctgg ctactcgtga accggaa         57

<210> SEQ ID NO 12
<211> LENGTH: 54
<212> TYPE: DNA
<213> ORGANISM: Escherichia coli

<400> SEQUENCE: 12
gctggttctc cgggtgctgc tctggctctg tttcagggtg atgactggca ggct            54

<210> SEQ ID NO 13
<211> LENGTH: 1002
<212> TYPE: DNA
<213> ORGANISM: Escherichia coli

<400> SEQUENCE: 13
atgagatggt atccatggtt acgacctgat ttcgaaaaac tggtagccag ctatcaggcc      60
ggaagaggtc accatgcgct actcattcag gcgttaccgg gcatgggcga tgatgcttta     120
atctacgccc tgagccgtta tttactctgc aacaaccgc agggccacaa aagttgcggt     180
```

```
cactgtcgtg gatgtcagtt gatgcaggct ggcacgcatc ccgattacta caccctggct      240
cccgaaaaag gaaaaaatac gctgggcgtt gatgcggtac gtgaggtcac cgaaaagctg      300
aatgagcacg cacgcttagg tggtgcgaaa gtcgtttggg taaccgatgc tgccttacta      360
accgacgccg cggctaacgc attgctgaaa acgcttgaag agccaccagc agaaacttgg      420
tttttcctgg ctacccgcga gcctgaacgt ttactggcaa cattacgtag tcgttgtcgg      480
ttacattacc ttgcgccgcc gccggaacag tacgccgtga cctggctttc acgcgaagtg      540
acaatgtcac aggatgcatt acttgccgca ttgcgcttaa gcgccggttc gcctggcgcg      600
gcactggcgt tgtttcaggg agataactgg caggctcgtg aaacattgtg tcaggcgttg      660
gcatatagcg tgccatcggg cgattggtat tcgctgctag cggcccttaa tcatgaacaa      720
gtcccggcgc gtttacactg gctggcaacg ttgctgatgg atgcgctaaa acgccatcat      780
ggtgctgcgc aggtgaccaa tgttgatgtg ccgggcctgg tcgccgaact ggcaaaccat      840
ctttctccct cgcgcctgca ggctatactg ggggatgttt gccacattcg tgaacagtta      900
atgtctgtta caggcatcaa ccgcgagctt ctcatcaccg atcttttact gcgtattgag      960
cattacctgc aaccgggcgt tgtgctaccg gttcctcatc tt                       1002

<210> SEQ ID NO 14
<211> LENGTH: 157
<212> TYPE: DNA
<213> ORGANISM: Escherichia coli

<400> SEQUENCE: 14
aagaatcttt cgatttcttt aatcgcaccc gcgcccgcta tctggaactg gcagcacaag       60
ataaaagcat tcataccatt gatgccaccc agccgctgga ggccgtgatg gatgcaatcc      120
gcactaccgt gacccactgg gtgaaggagt tggacgc                              157

<210> SEQ ID NO 15
<211> LENGTH: 143
<212> TYPE: DNA
<213> ORGANISM: Escherichia coli

<400> SEQUENCE: 15
ttagagagac atcatgtttt tagtggactc acactgccat ctcgatggtc tggattatga       60
atctttgcat aaggacgtgg atgacgttct ggcgaaagcc gccgcacgcg atgtgaaatt      120
ttgtctggca gtcgccacaa cat                                             143

<210> SEQ ID NO 16
<211> LENGTH: 16
<212> TYPE: PRT
<213> ORGANISM: Escherichia coli

<400> SEQUENCE: 16

Met Arg Trp Tyr Pro Pro Leu Arg Pro Asp Phe Glu Lys Leu Val Ala
 1               5                  10                  15

<210> SEQ ID NO 17
<211> LENGTH: 11
<212> TYPE: PRT
<213> ORGANISM: Escherichia coli

<400> SEQUENCE: 17

Glu Val Thr Glu Lys Leu Asn Glu His Ala Arg
 1               5                  10
```

```
<210> SEQ ID NO 18
<211> LENGTH: 20
<212> TYPE: PRT
<213> ORGANISM: Escherichia coli

<400> SEQUENCE: 18

Val Val Trp Val Thr Asp Ala Ala Leu Leu Thr Asp Ala Ala Ala Asn
 1               5                  10                  15

Ala Leu Leu Lys
            20

<210> SEQ ID NO 19
<211> LENGTH: 25
<212> TYPE: PRT
<213> ORGANISM: Escherichia coli

<400> SEQUENCE: 19

Thr Leu Glu Glu Pro Pro Ala Glu Thr Trp Phe Phe Leu Ala Thr Arg
 1               5                  10                  15

Glu Pro Glu Arg Leu Leu Ala Thr Leu
            20                  25

<210> SEQ ID NO 20
<211> LENGTH: 18
<212> TYPE: PRT
<213> ORGANISM: Escherichia coli

<400> SEQUENCE: 20

Leu His Tyr Leu Ala Pro Pro Glu Gln Tyr Ala Val Thr Trp Leu
 1               5                  10                  15

Ser Arg

<210> SEQ ID NO 21
<211> LENGTH: 21
<212> TYPE: PRT
<213> ORGANISM: Escherichia coli

<400> SEQUENCE: 21

Leu Ser Ala Gly Ser Pro Gly Ala Ala Leu Ala Leu Phe Gln Gly Asp
 1               5                  10                  15

Asn Trp Gln Ala Arg
            20

<210> SEQ ID NO 22
<211> LENGTH: 5
<212> TYPE: PRT
<213> ORGANISM: Escherichia coli

<400> SEQUENCE: 22

Leu Gly Gly Ala Lys
 1               5

<210> SEQ ID NO 23
<211> LENGTH: 58
<212> TYPE: PRT
<213> ORGANISM: Escherichia coli

<400> SEQUENCE: 23

Ala Cys Thr Cys Thr Gly Gly Ala Ala Gly Ala Ala Cys Cys Gly Cys
 1               5                  10                  15

Cys Gly Gly Cys Thr Thr Gly Ala Ala Ala Cys Thr Thr Gly Gly Thr
            20                  25                  30
```

-continued

```
Thr Thr Thr Thr Thr Cys Thr Gly Gly Cys Thr Ala Cys Thr Cys Gly
        35                  40                  45
Thr Gly Ala Ala Cys Cys Gly Gly Ala Ala
    50                  55
```

<210> SEQ ID NO 24
<211> LENGTH: 54
<212> TYPE: PRT
<213> ORGANISM: Escherichia coli

<400> SEQUENCE: 24

```
Gly Cys Thr Gly Gly Thr Thr Cys Thr Cys Cys Gly Gly Gly Thr Gly
1               5                   10                  15
Cys Thr Gly Cys Thr Cys Thr Gly Gly Cys Thr Cys Thr Gly Thr Thr
            20                  25                  30
Thr Cys Ala Gly Gly Gly Thr Gly Ala Thr Ala Ala Cys Thr Gly Gly
        35                  40                  45
Cys Ala Gly Gly Cys Thr
    50
```

<210> SEQ ID NO 25
<211> LENGTH: 33
<212> TYPE: PRT
<213> ORGANISM: Escherichia coli

<400> SEQUENCE: 25

```
Gly Gly Thr Gly Ala Ala Gly Gly Ala Gly Thr Thr Gly Gly Ala Cys
1               5                   10                  15
Ala Thr Ala Thr Gly Ala Gly Ala Thr Gly Gly Thr Ala Thr Cys Cys
            20                  25                  30
Ala
```

<210> SEQ ID NO 26
<211> LENGTH: 40
<212> TYPE: PRT
<213> ORGANISM: Escherichia coli

<400> SEQUENCE: 26

```
Met Leu Lys Asn Leu Ala Lys Leu Asp Gln Thr Glu Met Asp Lys Val
1               5                   10                  15
Asn Val Asp Leu Ala Ala Ala Gly Val Ala Phe Lys Glu Arg Tyr Asn
            20                  25                  30
Met Pro Val Ile Ala Glu Ala Val
        35                  40
```

<210> SEQ ID NO 27
<211> LENGTH: 57
<212> TYPE: DNA
<213> ORGANISM: Escherichia coli

<400> SEQUENCE: 27
atgctgaaaa acctggctaa actggatcag actgaaatgg ataaagttaa cgttgat         57

<210> SEQ ID NO 28
<211> LENGTH: 57
<212> TYPE: DNA
<213> ORGANISM: Escherichia coli

<400> SEQUENCE: 28
ctggctgctg ctggtgttgc ttttaaggaa cgttataaca tgccggttat tgctgaa         57

-continued

<210> SEQ ID NO 29
<211> LENGTH: 228
<212> TYPE: DNA
<213> ORGANISM: Escherichia coli

<400> SEQUENCE: 29

```
atgctgaaga atctggctaa actggatcaa acagaaatgg ataaagtgaa tgtcgatttg      60
gcggcggccg gggtggcatt taaagaacgc tacaatatgc cggtgatcgc tgaagcggtt     120
gaacgtgaac agcctgaaca tttgcgcagc tggtttcgcg agcggcttat tgcccaccgt     180
ttggcttcgg tcaatctgtc acgtttacct tacgagccca aacttaaa                  228
```

<210> SEQ ID NO 30
<211> LENGTH: 172
<212> TYPE: DNA
<213> ORGANISM: Escherichia coli

<400> SEQUENCE: 30

```
aggcgtagcg aagggagcgt gcagttgaag ccatattatc tattccttt tgtaataact       60
tttttacaga cgataacctt gtctaatgtc tgagtcgagg atcatcaatt ccggcttgcc     120
atcctggctc actcttagta acttttgccc gcgaatgatg aggagattaa ga             172
```

<210> SEQ ID NO 31
<211> LENGTH: 107
<212> TYPE: DNA
<213> ORGANISM: Escherichia coli

<400> SEQUENCE: 31

```
taaaacttat acagagttac actttcttac ataacgcctg ctaaattatg agtattttct      60
aaaccgcact cataatttgc agtcattttg aaaggaagt cattatg                    107
```

<210> SEQ ID NO 32
<211> LENGTH: 76
<212> TYPE: PRT
<213> ORGANISM: Escherichia coli

<400> SEQUENCE: 32

```
Met Leu Lys Asn Leu Ala Lys Leu Asp Gln Thr Glu Met Asp Lys Val
  1               5                  10                  15
Asn Val Asp Leu Ala Ala Ala Gly Val Ala Phe Lys Glu Arg Tyr Asn
             20                  25                  30
Met Pro Val Ile Ala Glu Ala Val Glu Arg Glu Gln Pro Glu His Leu
         35                  40                  45
Arg Ser Trp Phe Arg Glu Arg Leu Ile Ala His Arg Leu Ala Ser Val
     50                  55                  60
Asn Leu Ser Arg Leu Pro Tyr Glu Pro Lys Leu Lys
 65                  70                  75
```

<210> SEQ ID NO 33
<211> LENGTH: 40
<212> TYPE: PRT
<213> ORGANISM: Escherichia coli

<400> SEQUENCE: 33

```
Met Leu Lys Asn Leu Ala Lys Leu Asp Gln Thr Glu Met Asp Lys Val
  1               5                  10                  15
Asn Val Asp Leu Ala Ala Ala Gly Val Ala Phe Lys Glu Ala Tyr Asn
             20                  25                  30
```

```
Met Pro Val Ile Ala Glu Ala Val
        35                  40
```

<210> SEQ ID NO 34
<211> LENGTH: 57
<212> TYPE: DNA
<213> ORGANISM: Escherichia coli

<400> SEQUENCE: 34
atgctgaaaa acctggctaa actggatcag actgaaatgg ataaagttaa cgttgat         57

<210> SEQ ID NO 35
<211> LENGTH: 57
<212> TYPE: DNA
<213> ORGANISM: Escherichia coli

<400> SEQUENCE: 35
ctggctgctg ctggtgttgc ttttaaagaa cgttataaca tgccggttat tgctgaa         57

<210> SEQ ID NO 36
<211> LENGTH: 33
<212> TYPE: DNA
<213> ORGANISM: Escherichia coli

<400> SEQUENCE: 36
atgatgagga gattacatat gctgaagaat ctg                                   33

<210> SEQ ID NO 37
<211> LENGTH: 51
<212> TYPE: DNA
<213> ORGANISM: Escherichia coli

<400> SEQUENCE: 37
gaggaattcg gcttttttgc cgaattcctc ggcccctagg agatctcagc t               51

<210> SEQ ID NO 38
<211> LENGTH: 137
<212> TYPE: PRT
<213> ORGANISM: Escherichia coli

<400> SEQUENCE: 38

```
Met Thr Ser Arg Arg Asp Trp Gln Leu Gln Gln Leu Gly Ile Thr Gln
  1               5                  10                  15

Trp Ser Leu Arg Arg Pro Gly Ala Leu Gln Gly Glu Ile Ala Ile Ala
             20                  25                  30

Ile Pro Ala His Val Arg Leu Val Met Val Ala Asn Asp Leu Pro Ala
         35                  40                  45

Leu Thr Asp Pro Leu Val Ser Asp Val Leu Arg Ala Leu Thr Val Ser
     50                  55                  60

Pro Asp Gln Val Leu Gln Leu Thr Pro Glu Lys Ile Ala Met Leu Pro
 65                  70                  75                  80

Gln Gly Ser His Cys Asn Ser Trp Arg Leu Gly Thr Asp Glu Pro Leu
                 85                  90                  95

Ser Leu Glu Gly Ala Gln Val Ala Ser Pro Ala Leu Thr Asp Leu Arg
            100                 105                 110

Ala Asn Pro Thr Ala Arg Ala Ala Leu Trp Gln Gln Ile Cys Thr Tyr
        115                 120                 125

Glu His Asp Phe Phe Pro Gly Asn Asp
    130                 135
```

-continued

<210> SEQ ID NO 39
<211> LENGTH: 411
<212> TYPE: DNA
<213> ORGANISM: Escherichia coli

<400> SEQUENCE: 39

```
atgacatccc gacgagactg gcagttacag caactgggca ttacccagtg gtcgctgcgt    60
cgccctggcg cgttgcaggg cgagattgcc attgcgatcc cggcacacgt ccgtctggtg   120
atggtggcaa acgatcttcc cgccctgact gatcctttag tgagcgatgt tctgcgcgca   180
ttaaccgtca gccccgacca ggtgctgcaa ctgacgccaa aaaaaatcgc gatgctgccg   240
caaggcagtc actgcaacag ttggcggttg ggtactgacg aaccgctatc actggaaggc   300
gctcaggtgg catcaccggc gctcaccgat ttacgggcaa acccaacggc acgcgccgcg   360
ttatggcaac aaatttgcac atatgaacac gatttcttcc ctggaaacga c            411
```

<210> SEQ ID NO 40
<211> LENGTH: 77
<212> TYPE: DNA
<213> ORGANISM: Escherichia coli

<400> SEQUENCE: 40

```
ggcgattata gccatatgtt ggcgcggtat cgacgaattt gctatatttg cgcccctgac    60
aacaggagcg attcgct                                                   77
```

<210> SEQ ID NO 41
<211> LENGTH: 103
<212> TYPE: DNA
<213> ORGANISM: Escherichia coli

<400> SEQUENCE: 41

```
tgatttaccg gcagcttacc acattgaaca acgcgcccac gcctttccgt ggagtgaaaa    60
aacgtttgcc agcaaccagg gcgagcgtta tctcaacttt cag                     103
```

<210> SEQ ID NO 42
<211> LENGTH: 27
<212> TYPE: DNA
<213> ORGANISM: Escherichia coli

<400> SEQUENCE: 42

```
gattccatat gacatcccga cgagact                                        27
```

<210> SEQ ID NO 43
<211> LENGTH: 30
<212> TYPE: DNA
<213> ORGANISM: Escherichia coli

<400> SEQUENCE: 43

```
gactggatcc ctgcaggccg gtgaatgagt                                     30
```

<210> SEQ ID NO 44
<211> LENGTH: 17
<212> TYPE: PRT
<213> ORGANISM: Escherichia coli

<400> SEQUENCE: 44

Leu Gly Thr Asp Glu Pro Leu Ser Leu Glu Glu Ala Gln Val Ala Ser
 1               5                  10                  15
Pro

<210> SEQ ID NO 45
<211> LENGTH: 17
<212> TYPE: PRT
<213> ORGANISM: Escherichia coli

<400> SEQUENCE: 45

Ala Ala Leu Trp Gln Gln Ile Cys Thr Tyr Glu His Asp Phe Phe Pro
 1               5                  10                  15
Ala

<210> SEQ ID NO 46
<211> LENGTH: 32
<212> TYPE: DNA
<213> ORGANISM: Escherichia coli

<400> SEQUENCE: 46
caacaggagc gattccatat gacatcccga cg                                      32

<210> SEQ ID NO 47
<211> LENGTH: 31
<212> TYPE: DNA
<213> ORGANISM: Escherichia coli

<400> SEQUENCE: 47
gattcggatc cctgcaggcc ggtgaatgag t                                       31

<210> SEQ ID NO 48
<211> LENGTH: 30
<212> TYPE: DNA
<213> ORGANISM: Escherichia coli

<400> SEQUENCE: 48
ccccacatat gaaaaacgcg acgttctacc                                         30

<210> SEQ ID NO 49
<211> LENGTH: 28
<212> TYPE: DNA
<213> ORGANISM: Escherichia coli

<400> SEQUENCE: 49
acccggatcc aaactgccgg tgacattc                                           28

<210> SEQ ID NO 50
<211> LENGTH: 441
<212> TYPE: DNA
<213> ORGANISM: Escherichia coli

<400> SEQUENCE: 50
atgaaaaacg cgacgttcta ccttctggac aatgacacca ccgtcgatgg cttaagcgcc        60
gttgagcacc tggtgtgtga aattgccgca gaacgttggc gcagcggtaa gcgcgtgctc       120
atcgcctgtg aagatgaaaa gcaggcttac gccctggatg aagccctgtg ggcgcgtccg       180
gcagaaagct tgttccgca taatttagcg ggagaaggac cgcgcggcg tgtaccggtg         240 gagatcgcct ggccgcaaaa gcgtagcagc agccggcgcg atatattgat tagtctgcga       300
acaagctttg cagattttgc caccgctttt acagaagtgg tagacttcgt tcctcatgaa       360
gattctctga acaactggc gcgcgaacg tataaagcct accgcgtggc tggtttcaac         420
ctgaatacgg caacttggaa a                                                 441

<210> SEQ ID NO 51
<211> LENGTH: 175

<212> TYPE: DNA
<213> ORGANISM: Escherichia coli

<400> SEQUENCE: 51
taacggcgaa gagtaattgc gtcaggcaag gctgttattg ccggatgcgg cgtgaacgcc    60
ttatccgacc tacacagcac tgaactcgta ggcctgataa gacacaacag cgtcgcatca   120
ggcgctgcgg tgtatacctg atgcgtattt aaatccacca caagaagccc cattt        175

<210> SEQ ID NO 52
<211> LENGTH: 100
<212> TYPE: DNA
<213> ORGANISM: Escherichia coli

<400> SEQUENCE: 52
taatggaaaa gacatataac ccacaagata tcgaacagcc gctttacgag cactgggaaa    60
aaagccagga agtttctgc atcatgatcc cgccgccgaa                          100

<210> SEQ ID NO 53
<211> LENGTH: 147
<212> TYPE: PRT
<213> ORGANISM: Escherichia coli

<400> SEQUENCE: 53

Met Lys Asp Ala Thr Phe Tyr Leu Leu Asp Asn Asp Thr Thr Val Asp
 1               5                  10                  15

Gly Leu Ser Ala Val Glu Gln Leu Val Cys Glu Ile Ala Ala Glu Arg
                20                  25                  30

Trp Arg Ser Gly Lys Arg Val Leu Ile Ala Cys Glu Asp Glu Lys Gln
            35                  40                  45

Ala Tyr Arg Leu Asp Glu Ala Leu Trp Ala Arg Pro Ala Glu Ser Phe
        50                  55                  60

Val Pro His Asn Leu Ala Gly Glu Gly Pro Arg Gly Gly Ala Pro Val
 65                 70                  75                  80

Glu Ile Ala Trp Pro Gln Lys Arg Ser Ser Arg Arg Asp Ile Leu
                85                  90                  95

Ile Ser Leu Arg Thr Ser Phe Ala Asp Phe Ala Thr Ala Phe Thr Glu
               100                 105                 110

Val Val Asp Phe Val Pro Tyr Glu Asp Ser Leu Lys Gln Leu Ala Arg
           115                 120                 125

Glu Arg Tyr Lys Ala Tyr Arg Val Ala Gly Phe Asn Leu Asn Thr Ala
       130                 135                 140

Thr Trp Lys
145

<210> SEQ ID NO 54
<211> LENGTH: 29
<212> TYPE: PRT
<213> ORGANISM: Escherichia coli

<400> SEQUENCE: 54

Met Lys Asn Ala Thr Phe Tyr Leu Leu Asp Asn Asp Thr Thr Val Asp
 1               5                  10                  15

Gly Leu Ser Ala Val Glu Gln Leu Val Xaa Glu Ile Ala
                20                  25

<210> SEQ ID NO 55
<211> LENGTH: 9
<212> TYPE: PRT

-continued

```
<213> ORGANISM: Escherichia coli

<400> SEQUENCE: 55

Val Leu Ile Ala Xaa Glu Asp Glu Lys
 1               5

<210> SEQ ID NO 56
<211> LENGTH: 21
<212> TYPE: PRT
<213> ORGANISM: Escherichia coli

<400> SEQUENCE: 56

Leu Asp Glu Ala Leu Trp Ala Ala Pro Ala Glu Ser Phe Val Pro His
 1               5                  10                  15

Asn Leu Ala Gly Glu
            20

<210> SEQ ID NO 57
<211> LENGTH: 10
<212> TYPE: PRT
<213> ORGANISM: Escherichia coli

<400> SEQUENCE: 57

Gly Gly Ala Pro Val Glu Ile Ala Trp Pro
 1               5                  10

<210> SEQ ID NO 58
<211> LENGTH: 8
<212> TYPE: PRT
<213> ORGANISM: Escherichia coli

<400> SEQUENCE: 58

Gly Phe Asn Leu Asn Thr Ala Thr
 1               5

<210> SEQ ID NO 59
<211> LENGTH: 30
<212> TYPE: DNA
<213> ORGANISM: Escherichia coli

<400> SEQUENCE: 59
ccccacatat gaaaaacgcg acgttctacc                                    30

<210> SEQ ID NO 60
<211> LENGTH: 28
<212> TYPE: DNA
<213> ORGANISM: Escherichia coli

<400> SEQUENCE: 60
acccggatcc aaactgccgg tgacgttc                                      28
```